(12) United States Patent
Zhang et al.

(10) Patent No.: US 11,072,596 B2
(45) Date of Patent: Jul. 27, 2021

(54) POLY(ADP-RIBOSE) POLYMERASE INHIBITOR, PREPARATION METHOD AND USE

(71) Applicant: SELECTION BIOSCIENCE LLC, Shanghai (CN)

(72) Inventors: Fuyao Zhang, Shanghai (CN); Hongshun Yuan, Shanghai (CN); Xiaoming Shen, Shanghai (CN)

(73) Assignee: SELECTION BIOSCIENCE LLC, Shanghai (CN)

( * ) Notice: Subject to any disclaimer, the term of this patent is extended or adjusted under 35 U.S.C. 154(b) by 0 days.

(21) Appl. No.: 16/622,395

(22) PCT Filed: Jun. 14, 2018

(86) PCT No.: PCT/CN2018/091268
§ 371 (c)(1),
(2) Date: Dec. 13, 2019

(87) PCT Pub. No.: WO2018/228474
PCT Pub. Date: Dec. 20, 2018

(65) Prior Publication Data
US 2020/0207736 A1    Jul. 2, 2020

(30) Foreign Application Priority Data
Jun. 14, 2017 (CN) .......................... 201710454485.5

(51) Int. Cl.
| C07D 401/10 | (2006.01) |
| A61P 35/00 | (2006.01) |
| C07B 59/00 | (2006.01) |
| A61K 45/06 | (2006.01) |

(52) U.S. Cl.
CPC ............ *C07D 401/10* (2013.01); *A61P 35/00* (2018.01); *C07B 59/002* (2013.01); *A61K 45/06* (2013.01)

(58) Field of Classification Search
CPC ...... C07D 401/10; A61P 35/00; C07B 59/002
See application file for complete search history.

(56) References Cited

U.S. PATENT DOCUMENTS

| 2008/0167345 A1* | 7/2008 | Jones ...................... A61P 25/28 514/322 |
| 2017/0298069 A1* | 10/2017 | Brooijmans ......... C07D 519/00 |

FOREIGN PATENT DOCUMENTS

| CN | 1870991 A | 11/2006 |
| CN | 1890224 A | 1/2007 |
| CN | 101578279 A | 11/2009 |
| CN | 101932572 A | 12/2010 |
| CN | 110300587 A | 10/2019 |
| EP | 2336120 B1 | 7/2014 |
| PT | 2336120 E | 10/2014 |
| WO | 2005023246 A | 3/2005 |
| WO | 2005054210 A | 6/2005 |
| WO | 2008084261 A | 7/2008 |
| WO | 2009087381 A | 7/2009 |
| WO | WO-2012006958 A1 * | 1/2012 ............... A61P 9/00 |
| WO | 2014088983 A1 | 6/2014 |
| WO | 2015051766 A1 | 4/2015 |
| WO | 2018187187 A1 | 10/2018 |
| WO | WO-2018192445 A1 * | 10/2018 .............. A61P 35/00 |

OTHER PUBLICATIONS

Chinese Patent Office. Office Action dated Sep. 30, 2020 in Application 201710454485.5. English Translation. 7 Pages. (Year: 2020).*
Jones Philip et al., "Discovery of 2-{4-[(3S)-Piperidin-3-yl]phenyl}-2H-indazole-7-carboxamide (MK-4827): A novel oral poly(ADP-ribose)polymerase (PARP) inhibitor efficacious in BRCA-1 and -2 mutant tumors", Journal of Medicinal Chemistry, vol. 52, No. 22, p. 7170-7185.
International Search Report and Written Opinion of PCT/CN2018/091268 dated Aug. 30, 2018.
Extended European Search Report issued in the counterpart European application No. 18817795.0 dated Mar. 10, 2020.
Chinese First Office Action issued in Chinese Patent Application No. 201710454485.5 dated Sep. 30, 2020, 12 pages.
European First Office Action issued in European Patent Application No. 18817795.0 dated Dec. 22, 2020, 3 pages.

* cited by examiner

*Primary Examiner* — Daniel R Carcanague
(74) *Attorney, Agent, or Firm* — MH2 Technology Law Group, LLP

(57) ABSTRACT

Disclosed are a compound as shown in general formula I, a pharmaceutically acceptable salt, an isomer or a mixture thereof, and a solvate, a polymorph, a stable isotope derivative or a prodrug thereof. The compound of the present disclosure has comparatively strong PARP inhibitory activity and can be used for treating diseases associated with PARP, such as cancers and inflammatory diseases.

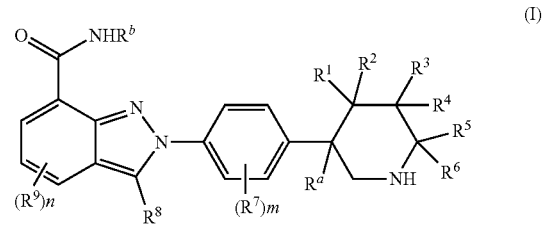

20 Claims, 1 Drawing Sheet

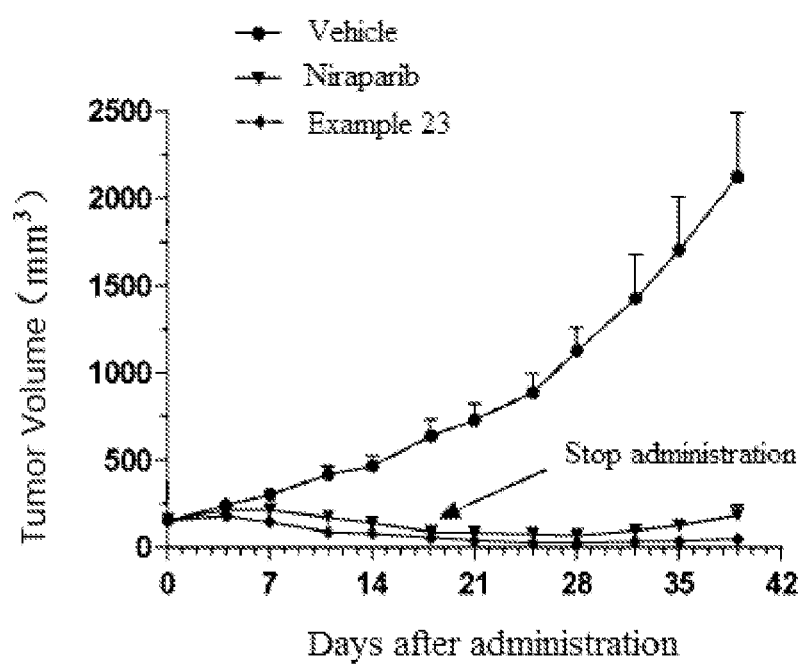

POLY(ADP-RIBOSE) POLYMERASE INHIBITOR, PREPARATION METHOD AND USE

CROSS-REFERENCE TO RELATED APPLICATIONS

This application is a national stage entry from International Application No. PCT/CN2018/091268, filed on Jun. 14, 2018, published as International Publication No. WO 2018/228474 A1 on Dec. 20, 2018, and claims priority under 35 U.S.C. § 119 from Chinese patent application No. 201710454485.5, filed on Jun. 14, 2017, the entire contents of all of which are incorporated herein by reference.

The present application claims the priority to Chinese patent application NO. 201710454485.5, filed on Jun. 14, 2017. The contents of which are incorporated herein by its entirety.

FIELD OF THE INVENTION

The present disclosure relates to a poly (ADP-ribose) polymerase inhibitor, a preparation method, and a use thereof.

BACKGROUND OF THE INVENTION

Poly (ADP-ribose) polymerase (PARP) is a class of ribozymes in eukaryotic cells involved in a variety of cellular processes, such as DNA damage repair, genomic stability, and programmed cells death. It was first reported in 1963, and the PARP family contains at least 18 subtypes with different structures and cellular functions, including PARP-1, PARP-2, PARP-4, Tankyrase-1 and 2, and other PARP-3 to 16. PARP is composed of four domains: a DNA-binding domain, a caspase-cleaved domain, an automodification domain, and a catalytic domain. Among them, PARP-1 was first discovered. Although PARP-1 and PARP-2 have similar structures, the process of DNA damage repair is mostly completed by PARP-1, so the research on PARP inhibitor drugs was mainly focused on PARP-1 inhibitors.

Many types of cancer cells are more dependent on PARP than conventional cells, which make PARP inhibitor drugs the most attractive targets in cancer therapy. PARP-1 inhibitors can be used as sensitizers to improve the efficacy of anticancer drugs. Chemotherapy or radiotherapy drugs inhibit or kill cells by destroying the DNA structure of tumor cells, while tumor cells can repair damaged DNA cells through PARP-1, thus generating drug resistance to chemotherapeutic drugs. Therefore, PARP-1 inhibitor drugs can be combined with chemotherapeutic drugs to deal with drug resistance, thus reducing drug dosage and improving the curative effect. In addition, studies have shown that using a PARP-1 inhibitor alone can kill DNA repair-defective cancer cells, especially BRCA-1/2 deleted or mutant cancer cells.

Based on years of research on PARP inhibitors, PARP-1 inhibitors have become one of the hotspots in cancer drug research and development, and the reliability and feasibility of this target have been confirmed. AstraZeneca's Olaparib, trade name Lynparza, was approved by EMA and FDA in 2014 for monotherapy after chemotherapy for advanced ovarian cancer associated with BRCA gene mutation. Subsequently, Pfizer's Rucaparib and Tesaro's Niraparib were approved by FDA for the treatment of patients after chemotherapy. Besides, other drugs in research, such as Talazoparib and Veliparib, are all in the clinical experimental stage.

These recent findings also confirm that PARP inhibitors have huge advantages in the treatment of BRCA gene deletion or mutation related cancers.

SUMMARY OF THE INVENTION

The present disclosure aims to provide a poly (ADP-ribose) polymerase inhibitor, a preparation method, and a use thereof. The compound of the present disclosure has strong PARP inhibitory activity and can be used for treating diseases related to PARP, such as cancers, inflammatory diseases and the like.

In a first aspect, the present disclosure provides a compound as shown in general formula I, a pharmaceutically acceptable salt thereof, an isomer thereof or a mixture of the isomers, a solvate thereof, a polymorph thereof, a stable isotope derivative thereof or a prodrug thereof;

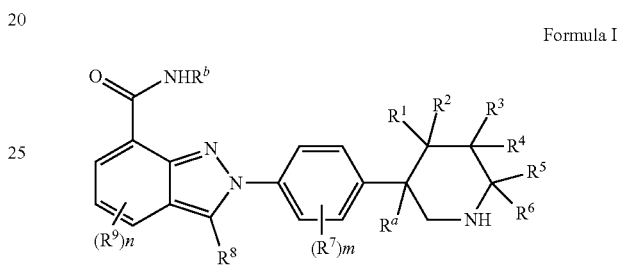

Formula I wherein, $R^a$ is selected from hydrogen, deuterium, fluorine, substituted or unsubstituted $C_{1-6}$ alkyl or substituted or unsubstituted cycloalkyl;

$R^b$ is selected from hydrogen, deuterium, substituted or unsubstituted $C_{1-6}$ alkyl or substituted or unsubstituted cycloalkyl;

$R^1$, $R^2$, $R^3$, $R^4$, $R^5$, $R^6$, $R^7$, $R^8$, and $R^9$ are each independently selected from hydrogen, deuterium or fluorine, and when $R^a$ is hydrogen, then at least one of $R^1$, $R^2$, $R^3$, $R^4$, $R^5$, $R^6$, $R^7$, $R^8$ and $R^9$ is deuterium or fluorine;

when $R^a$ is hydrogen, n is 1, and $R^9$ is fluorine at position 5, then $R^1$, $R^2$, $R^3$, $R^4$, $R^5$, $R^6$, and $R^8$ are not hydrogen at the same time;

when $R^a$ is hydrogen, m is not 0, and $R^7$ is fluorine, then $R^1$, $R^2$, $R^3$, $R^4$, $R^5$, $R^6$, and $R^8$ are not hydrogen at the same time;

m is the number of $R^7$ and is 0, 1, 2, 3, or 4;

n is the number of $R^9$ and is 0, 1, 2, or 3.

In a preferred embodiment of the present disclosure, $R^b$ is hydrogen or deuterium.

In a preferred embodiment of the present disclosure, the structure of the compound as shown in general formula I is as follows:

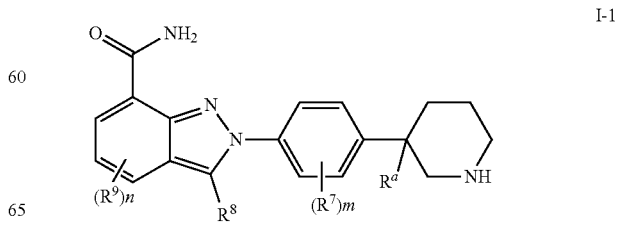

I-1 wherein $R^a$ is selected from deuterium, fluorine or substituted or unsubstituted $C_{1-6}$ alkyl; $R^7$, $R^8$, $R^9$, m and n are defined as above.

In a preferred embodiment of the present disclosure, the structure of the compound as shown in general formula I is as follows:

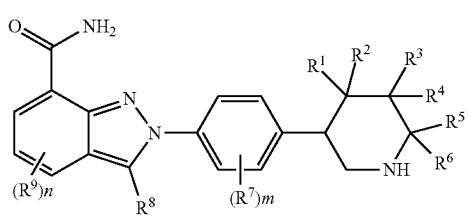

I-2 wherein at least one of $R^1$, $R^2$, $R^3$, $R^4$, and $R^6$ is deuterium or fluorine, and $R^7$, $R^8$, $R^9$, m and n are as defined above.

In a preferred embodiment of the present disclosure, the structure of the compound as shown in general formula I is as follows:

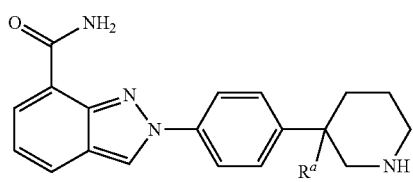

I-3 wherein, $R^a$ is selected from deuterium, fluorine or substituted or unsubstituted $C_{1-6}$ alkyl.

In some embodiments of the present disclosure, the structure of the compound as shown in general formula I is a compound as shown in general formula I-4:

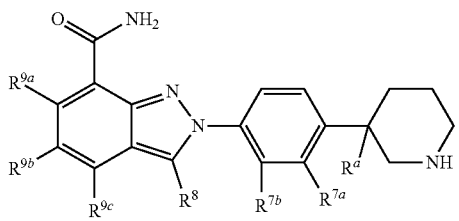

I-4 wherein $R^a$ is methyl, fluorine or deuterium;
$R^{7a}$, $R^{7b}$, $R^8$, $R^{9a}$, $R^{9b}$ and $R^{9c}$ are each independently hydrogen or fluorine.

In the compound as shown in general formula I-4, the $R^a$ can be fluorine or deuterium, and can also be fluorine.

In the compound as shown in general formula I-4, the $R^{7b}$ can be hydrogen.

In the compound as shown in general formula I-4, the $R^8$ can be hydrogen.

In the compound as shown in general formula I-4, the $R^{9a}$ can be hydrogen.

In the compound as shown in general formula I-4, the $R^{9c}$ can be hydrogen.

In some aspects of the present disclosure, in the compound as shown in general formula I-4, the $R^a$ is methyl, fluorine or deuterium, and the $R^{7a}$, $R^{7b}$, $R^8$, $R^{9b}$ and $R^{9c}$ are each independently hydrogen or fluorine, and there are at most only two fluorines.

In some aspects of the present disclosure, in the compound as shown in general formula I-4, the $R^a$ is methyl, fluorine or deuterium, and the $R^8$ is hydrogen; the $R^{7b}$, $R^{9a}$, and $R^{9c}$ are each independently hydrogen or fluorine, and there is at most only one fluorine; the $R^{7a}$ and $R^{9b}$ are each independently hydrogen or fluorine.

In some aspects of the present disclosure, in the compound as shown in general formula I-4, the $R^a$ is fluorine or deuterium, the $R^8$, $R^{9a}$ and $R^{9c}$ are hydrogen, the $R^{7b}$, $R^{7a}$ and $R^{9b}$ are each independently hydrogen or fluorine, and when the $R^{7b}$ is fluorine, then the $R^{9b}$ is fluorine.

In some aspects of the present disclosure, in the compound as shown in general formula I-4, the $R^a$ is fluorine or deuterium, the $R^{7b}$, $R^8$, $R^{9a}$ and $R^{9c}$ are hydrogen, and the $R^{7a}$ and $R^{9b}$ are each independently hydrogen or fluorine.

In some aspects of the present disclosure, in the compound as shown in general formula I-4, the $R^a$ is fluorine, the $R^{7b}$, $R^8$, $R^{9a}$ and $R^{9c}$ are hydrogen, and the $R^{7a}$ and $R^{9b}$ are each independently hydrogen or fluorine.

In a preferred embodiment of the present disclosure, the compound as shown in general formula I is selected from any of the following compounds:

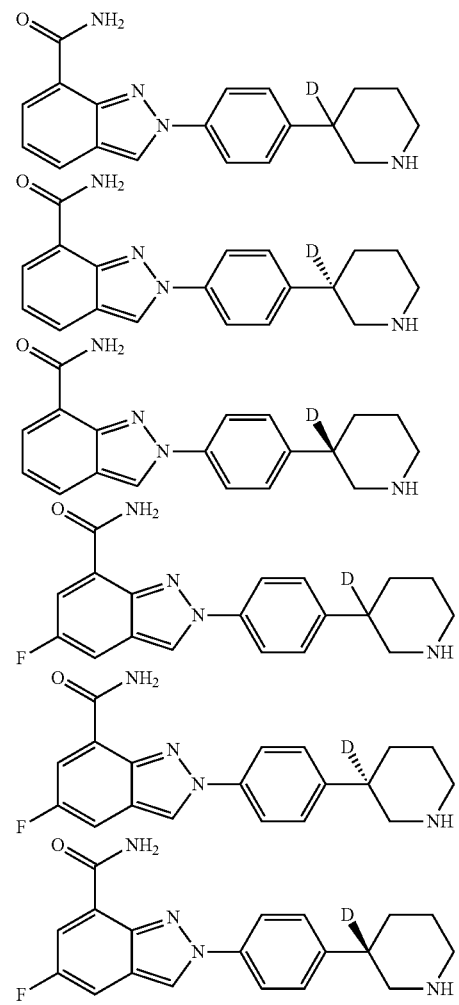

-continued
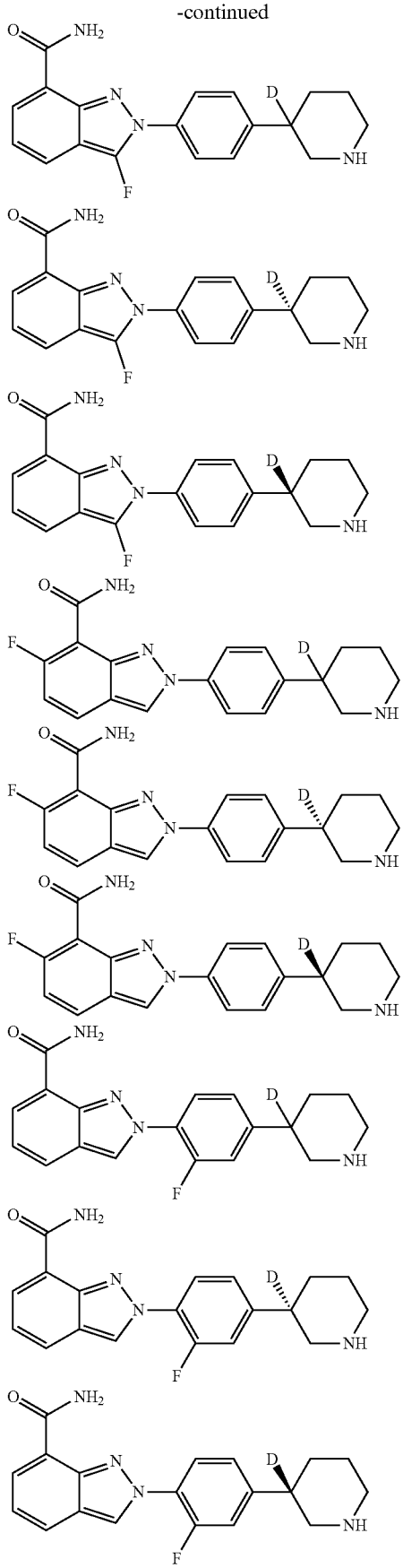
-continued
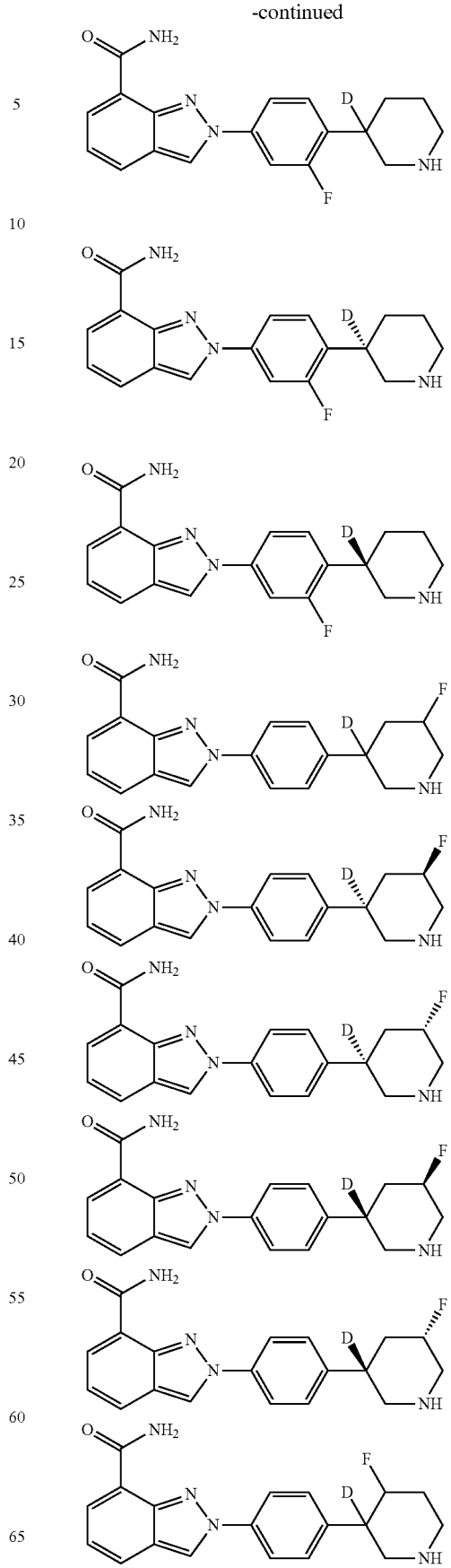

-continued
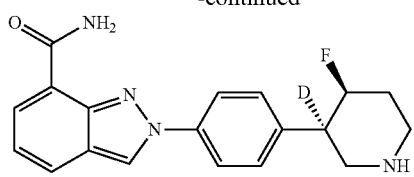
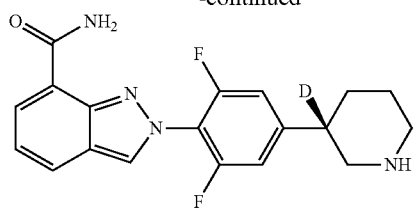

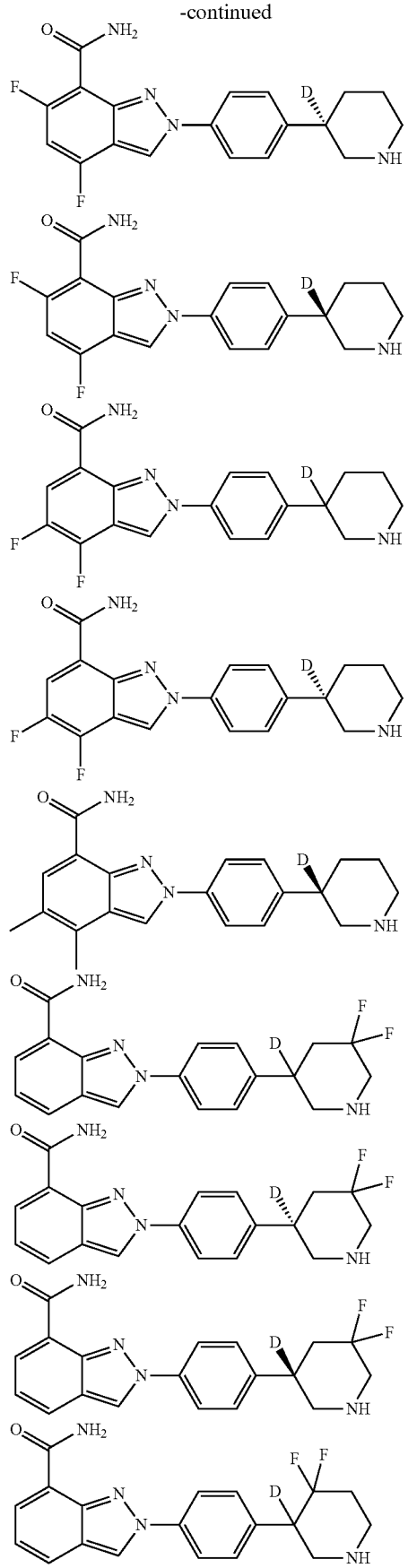
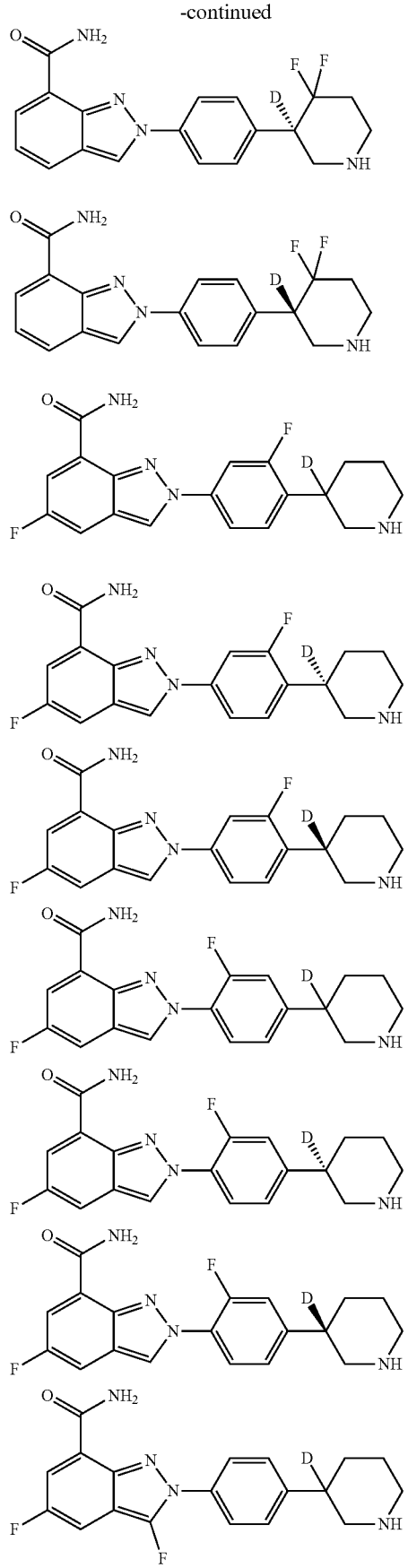

-continued
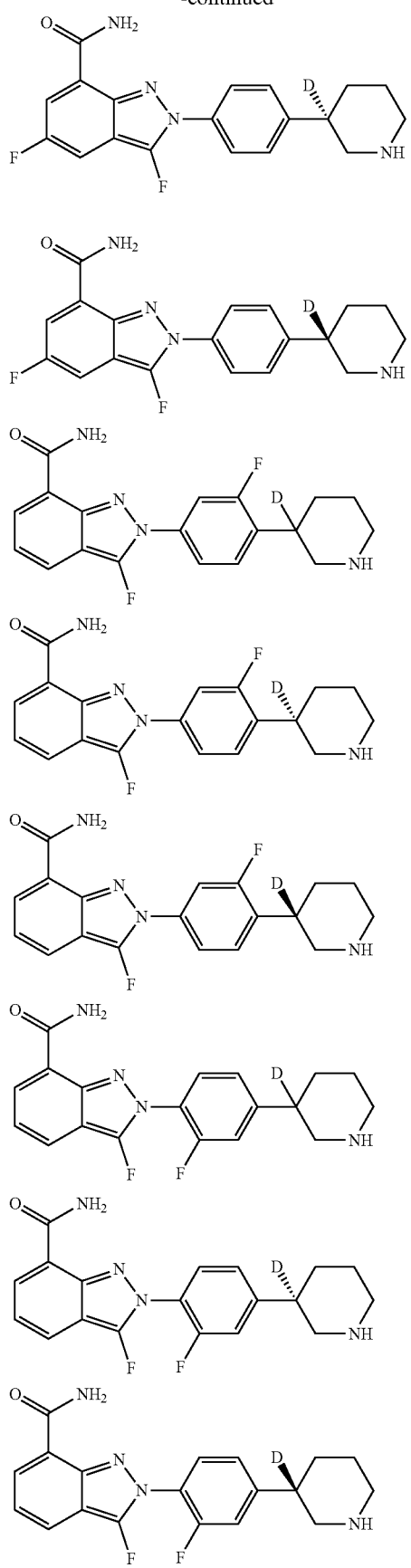
-continued
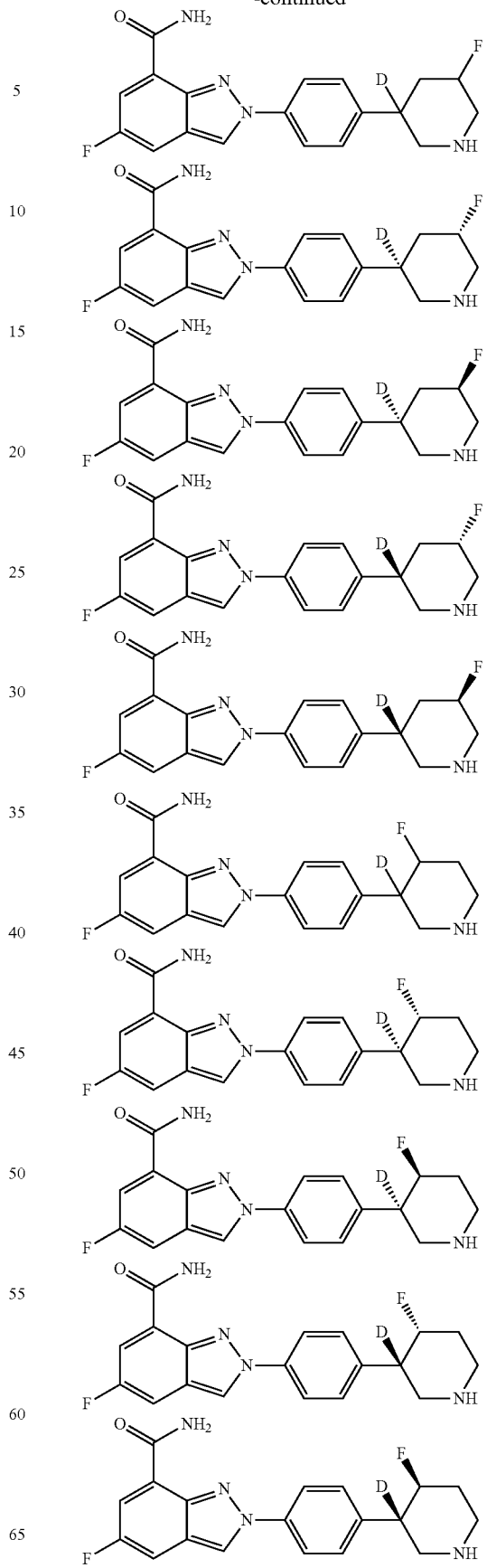

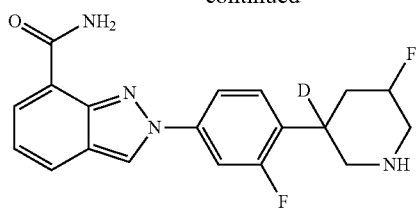
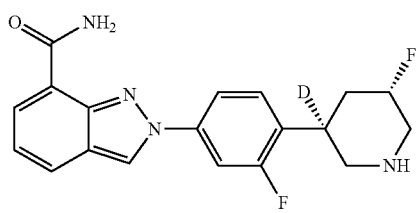
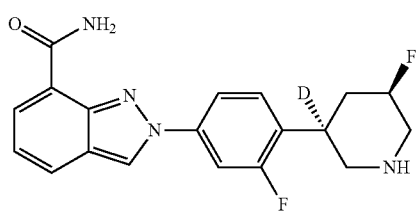
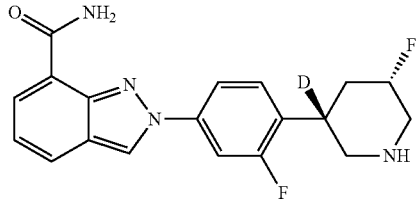
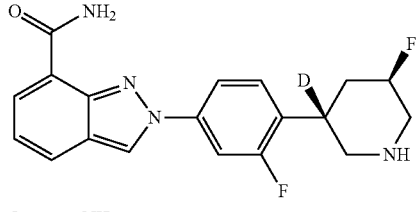
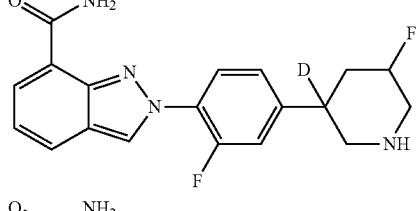
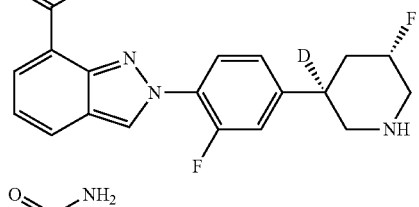
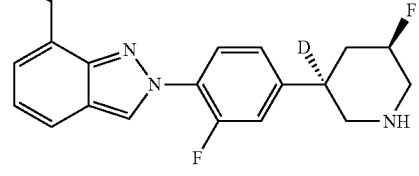
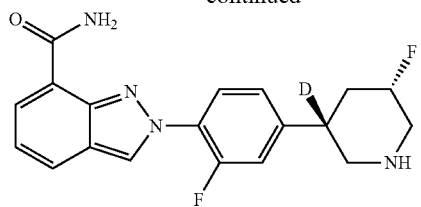
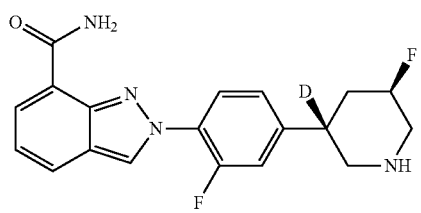
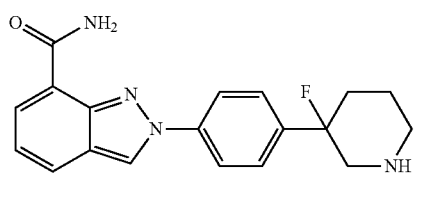
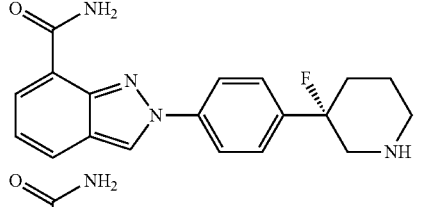
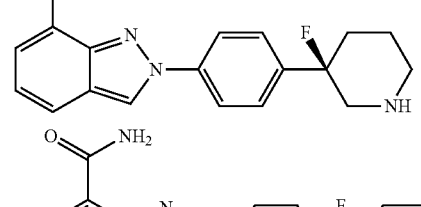
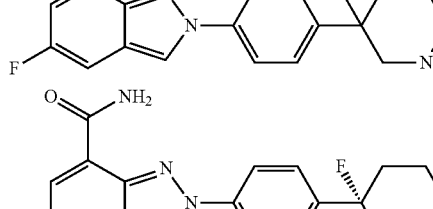
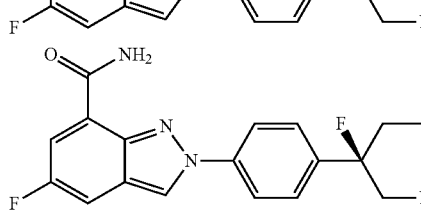
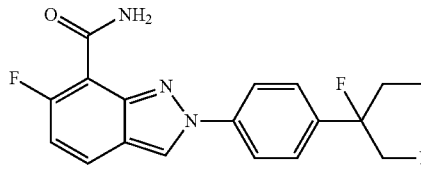

-continued
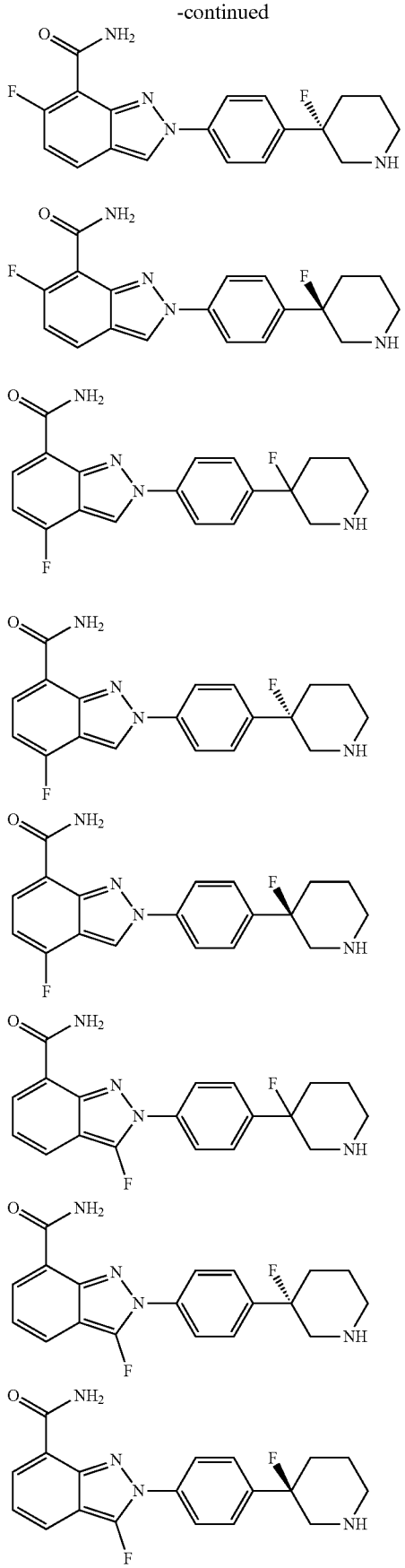
-continued
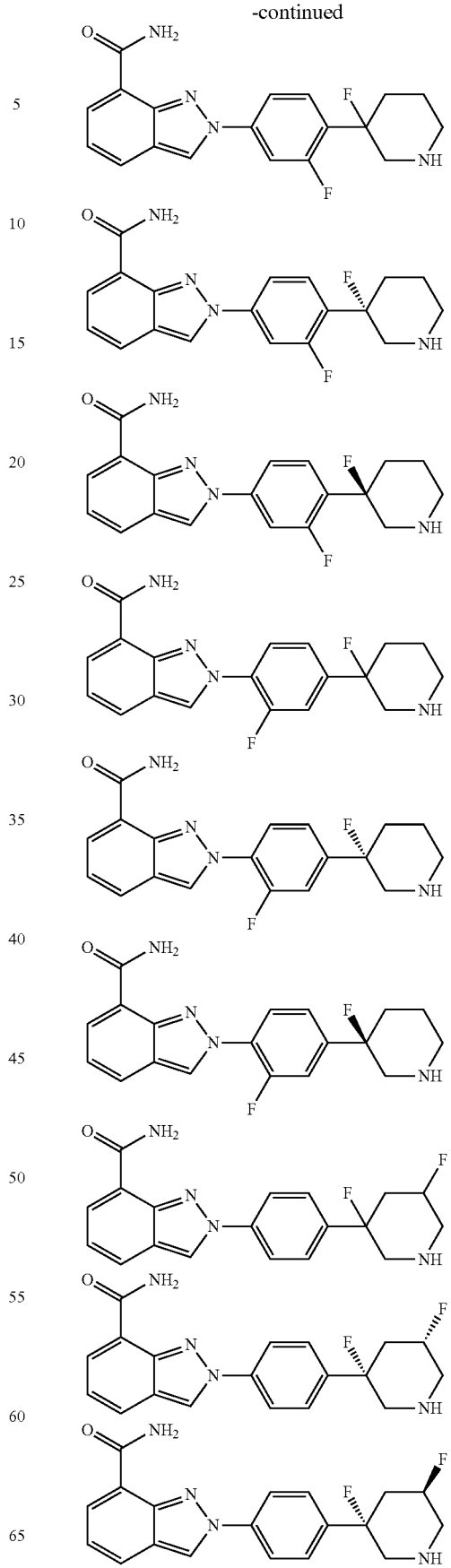

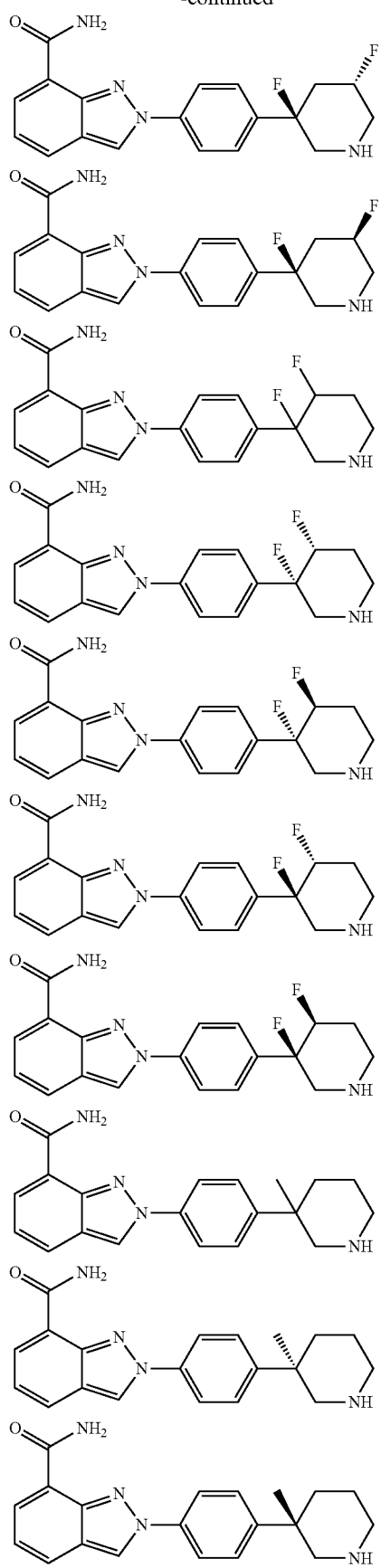
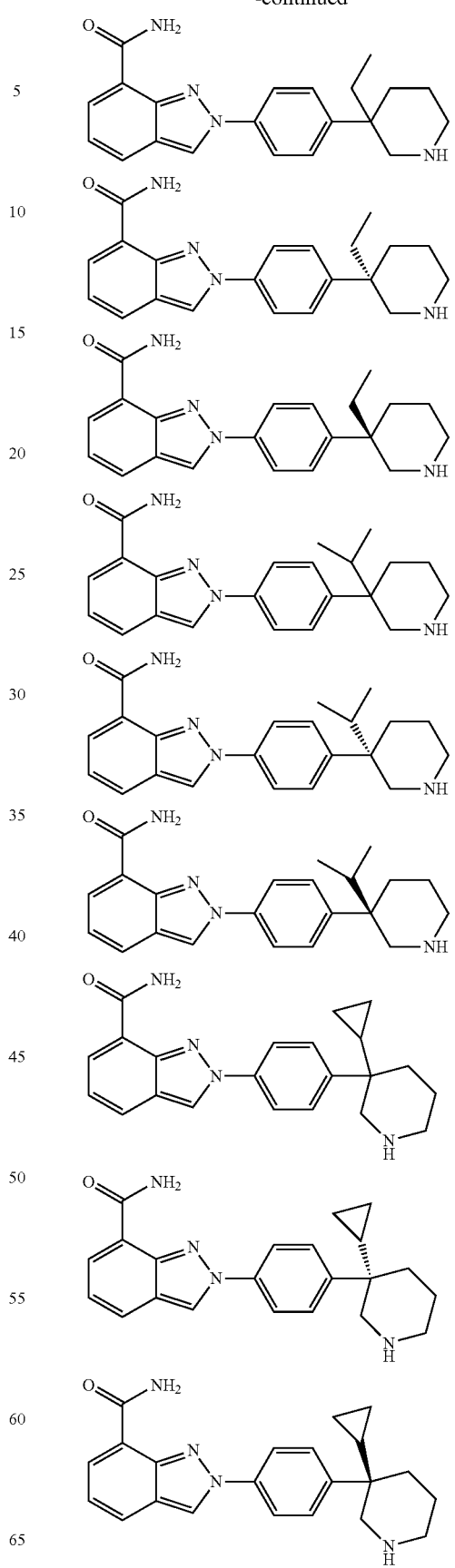

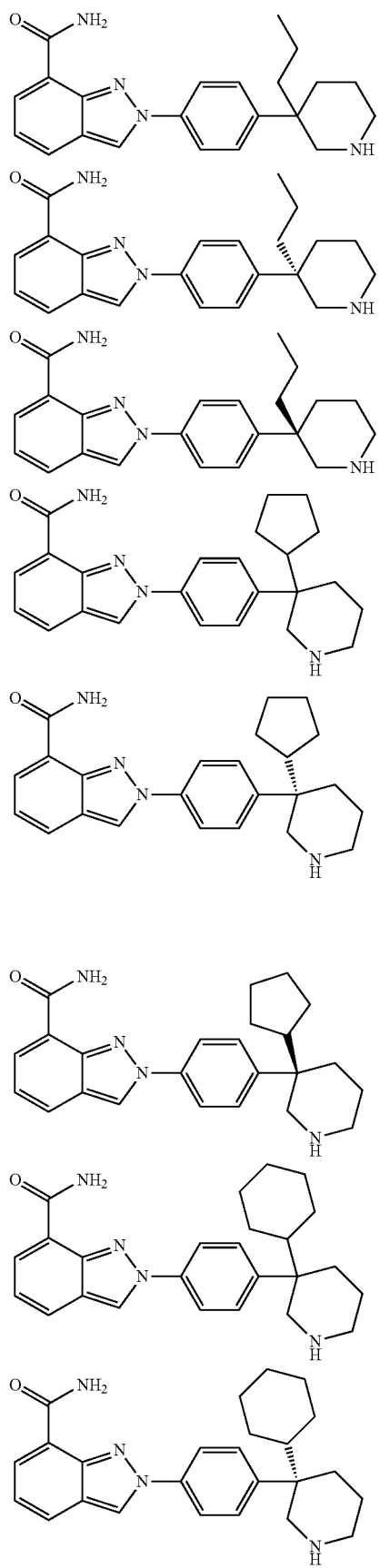
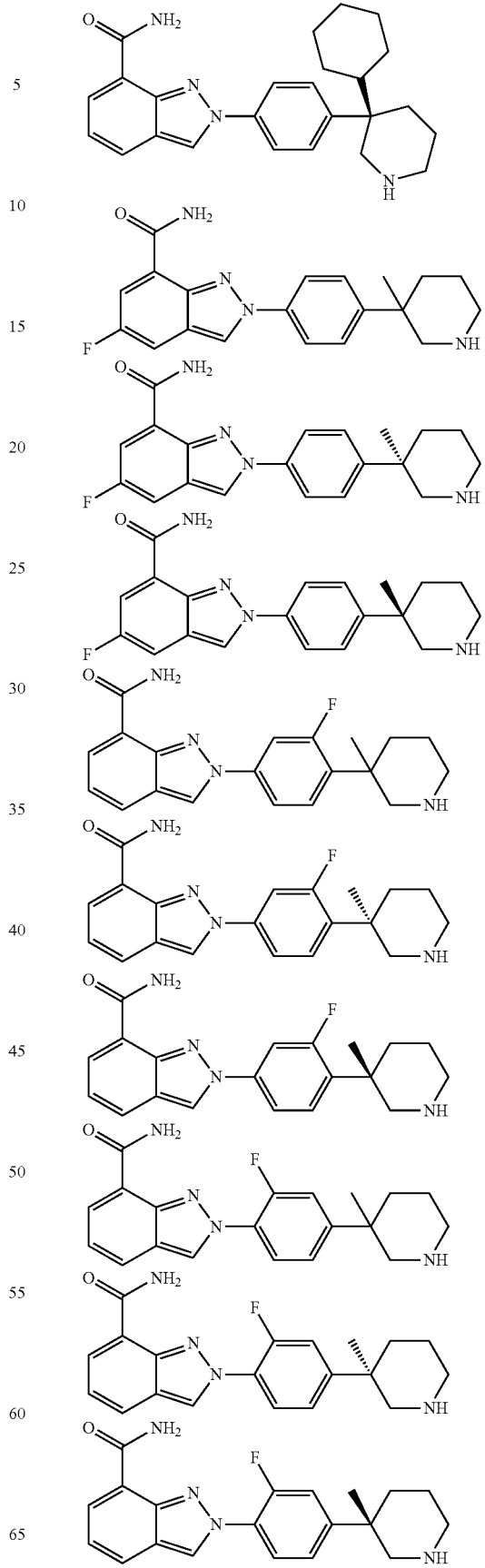

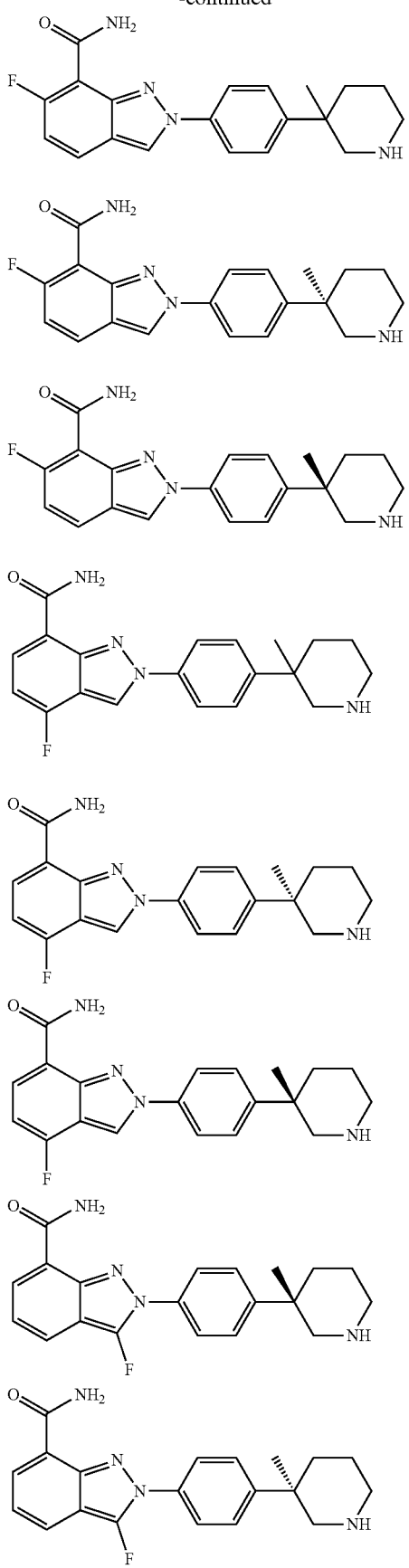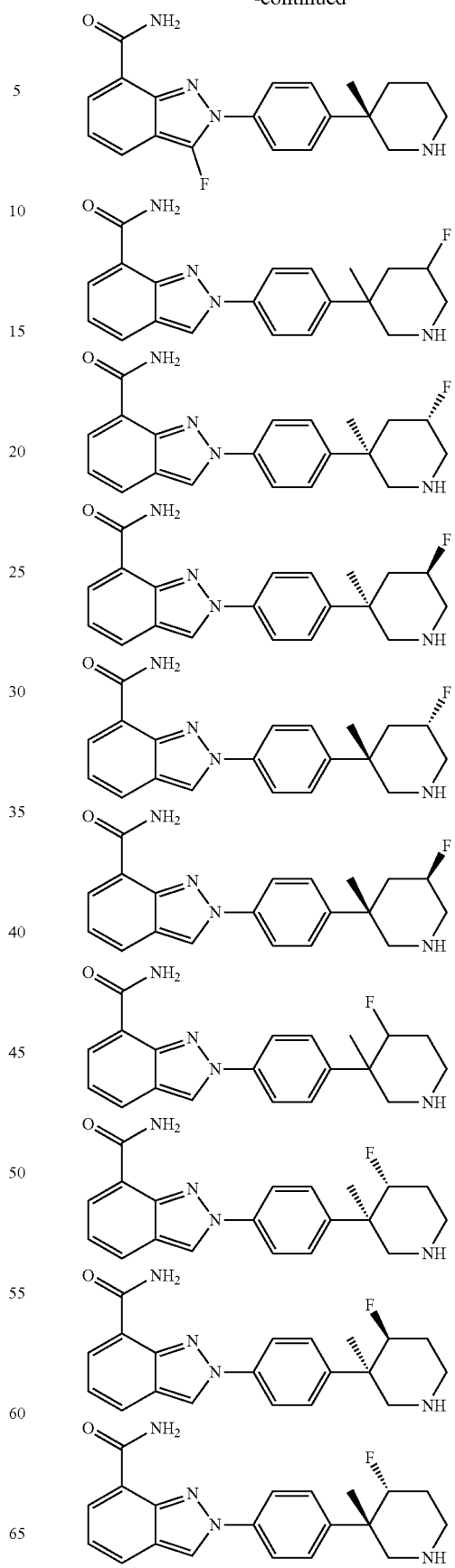

-continued
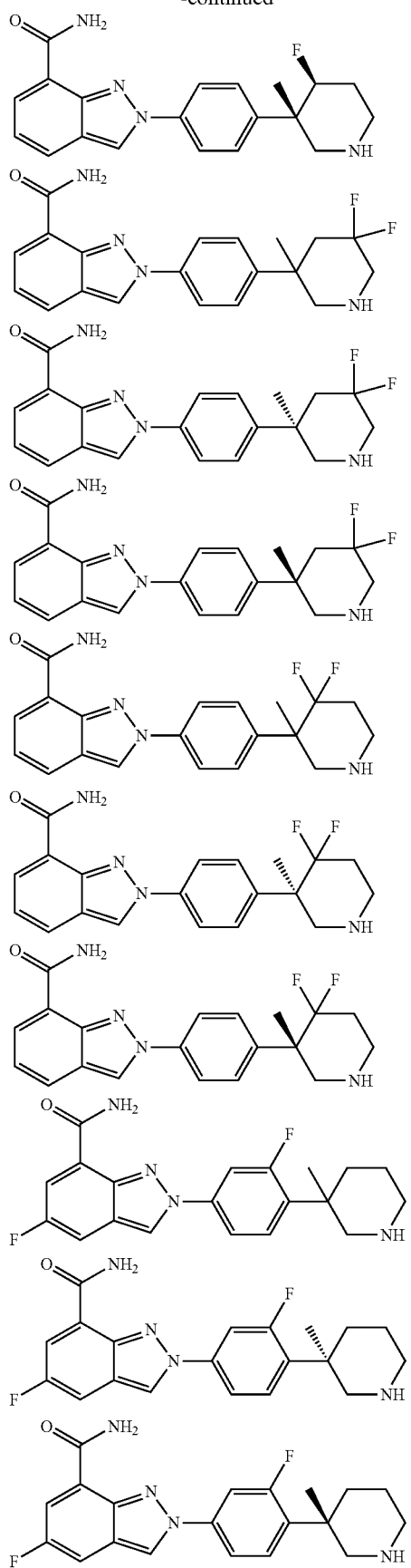
-continued
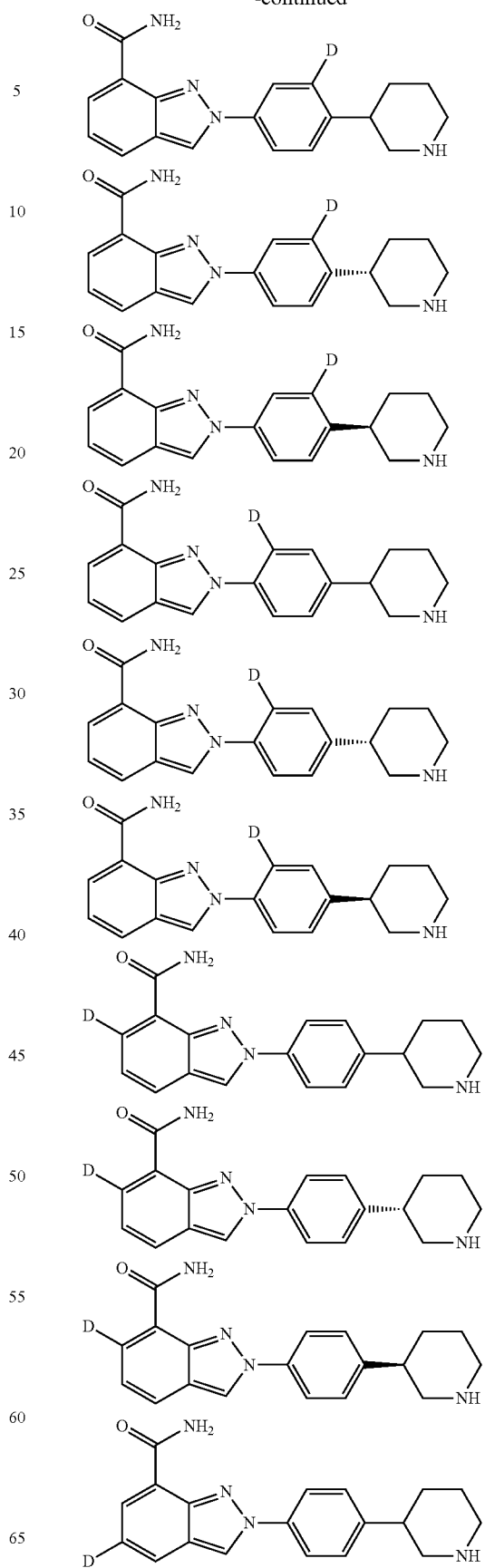

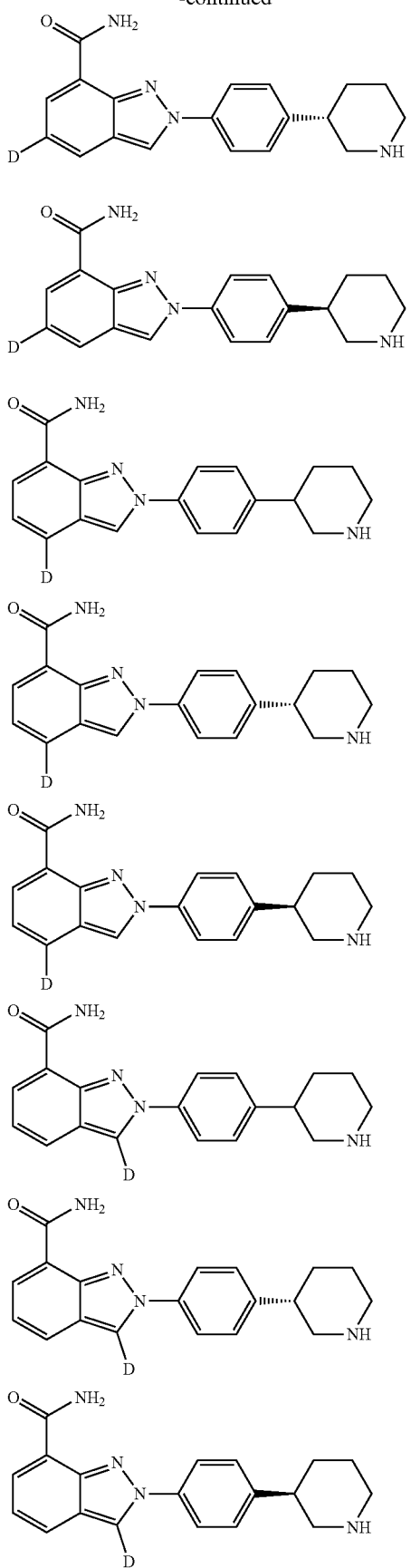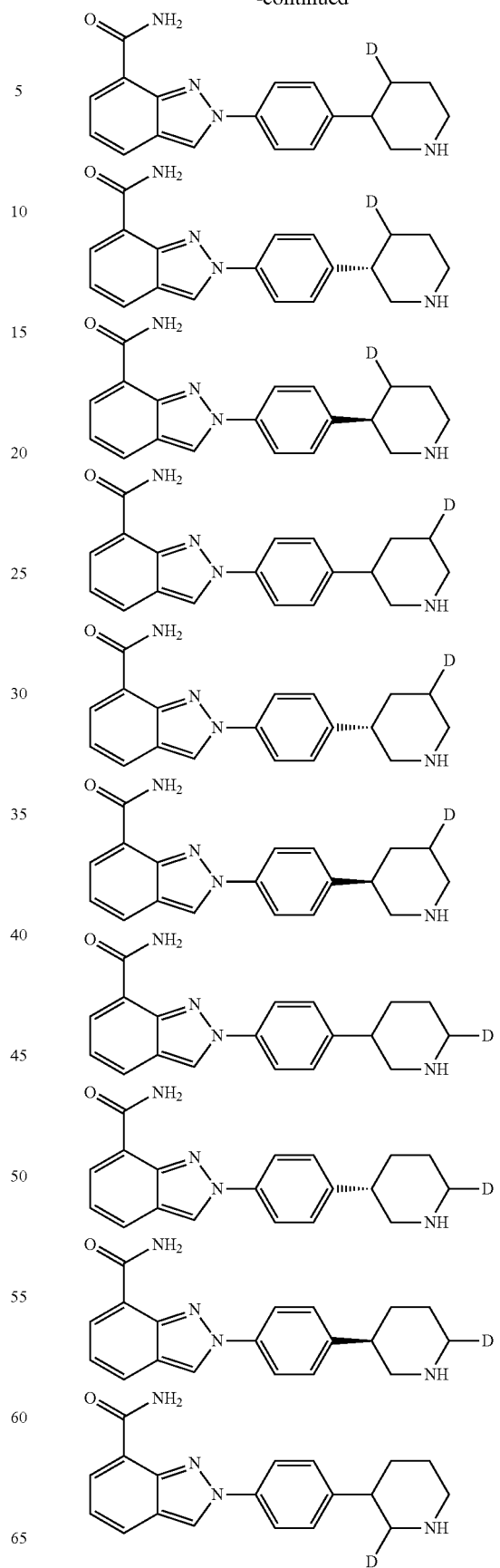

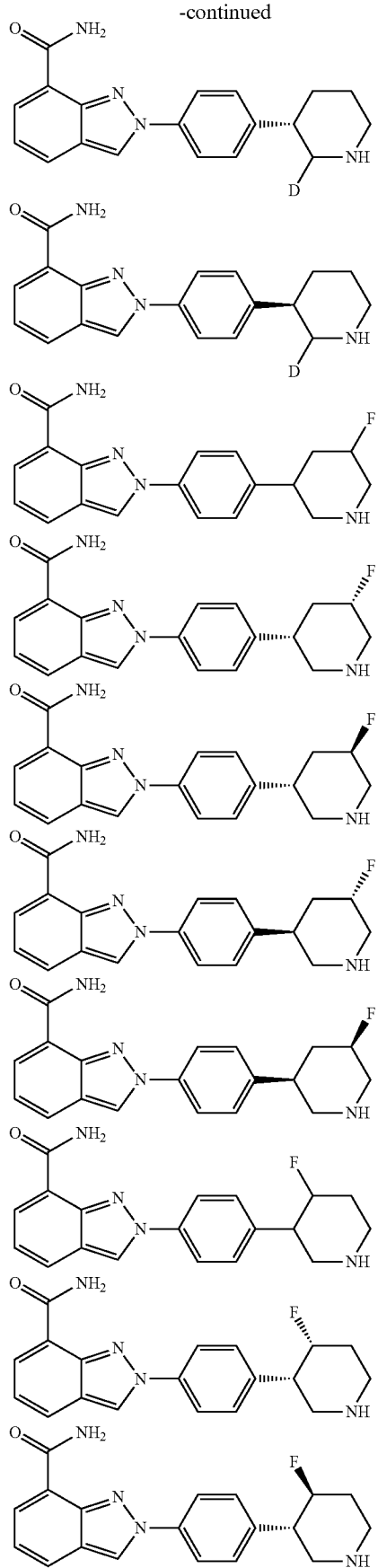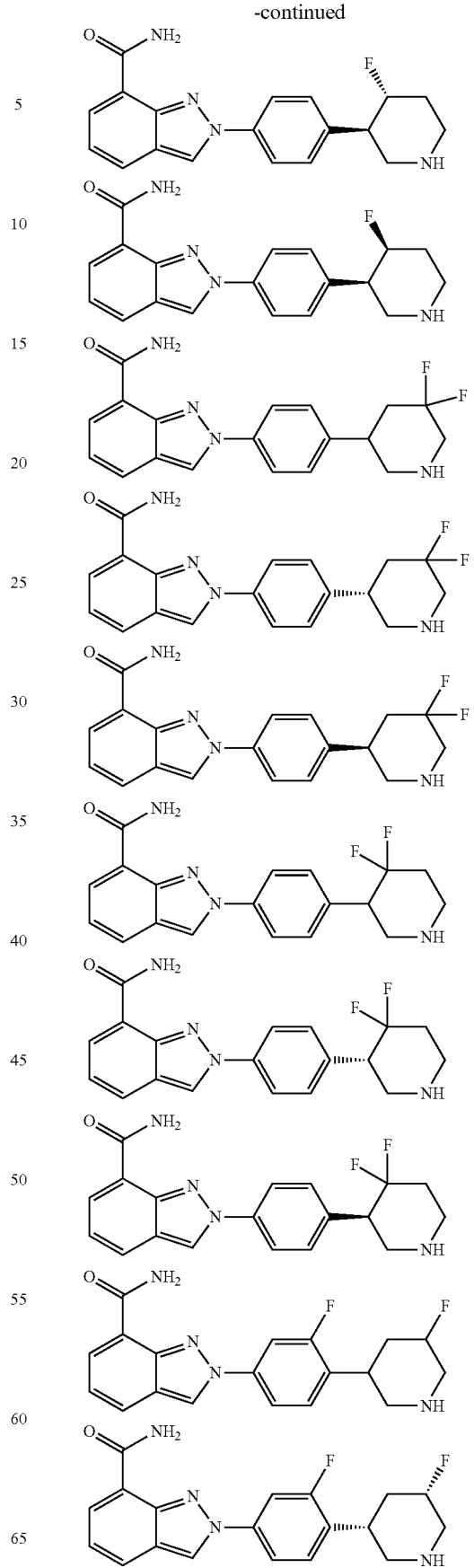

-continued
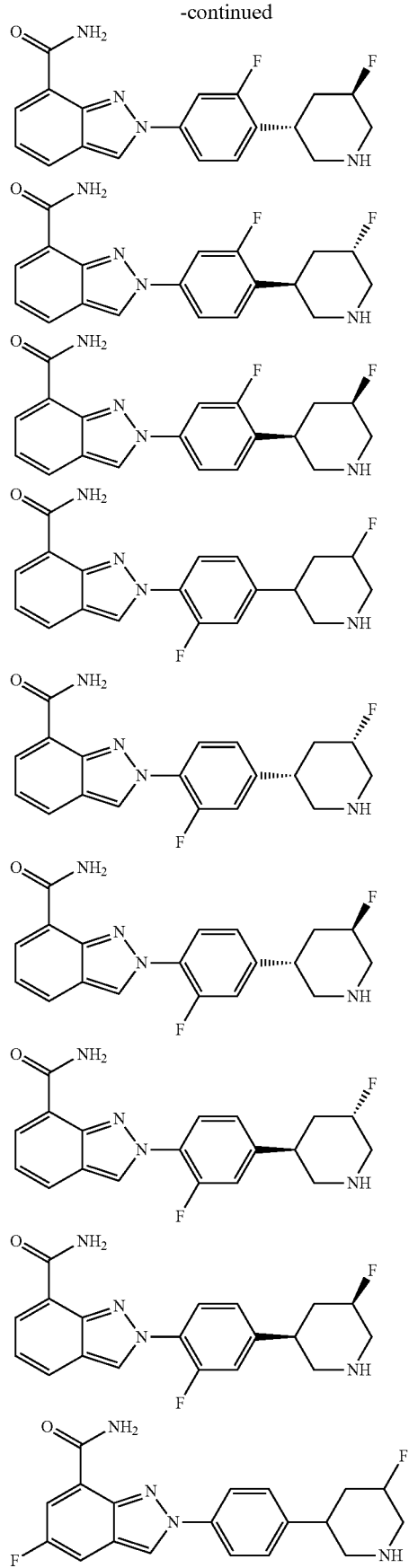
-continued
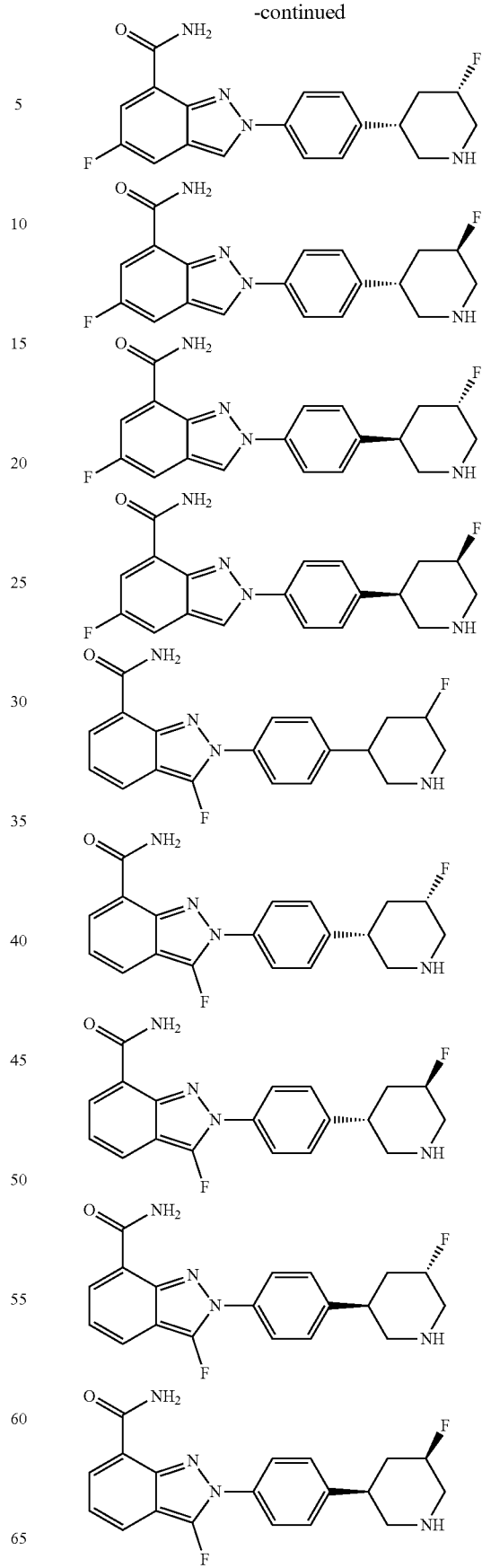

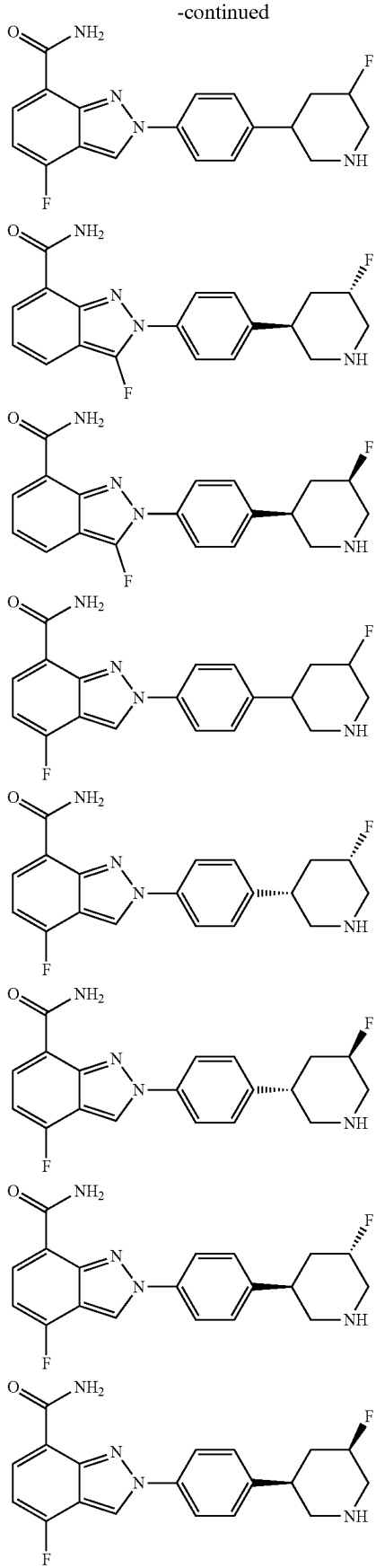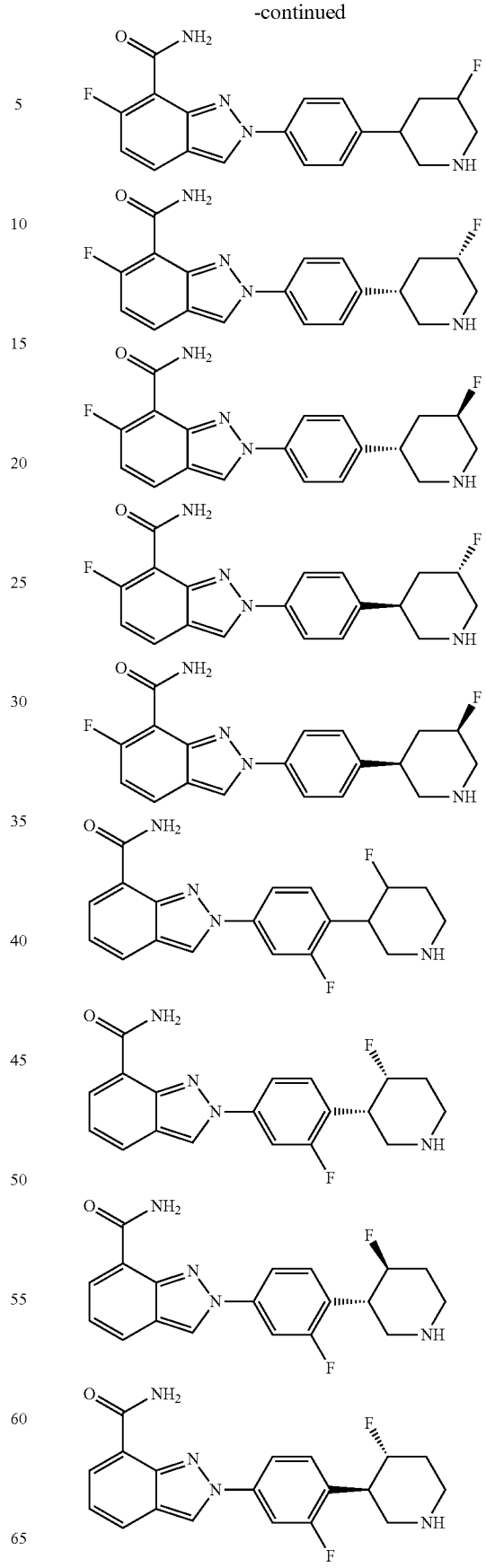

33
-continued
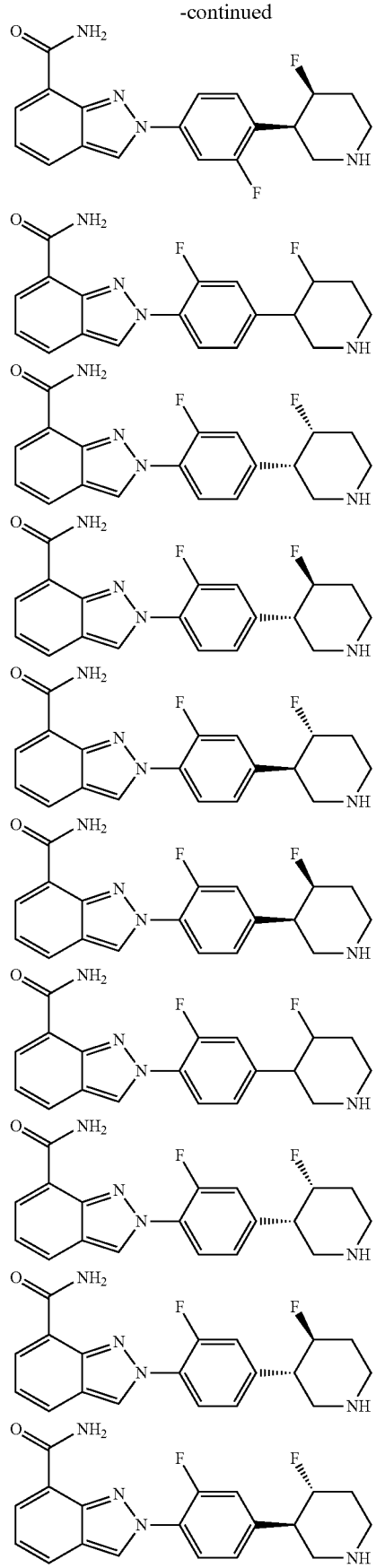
34
-continued
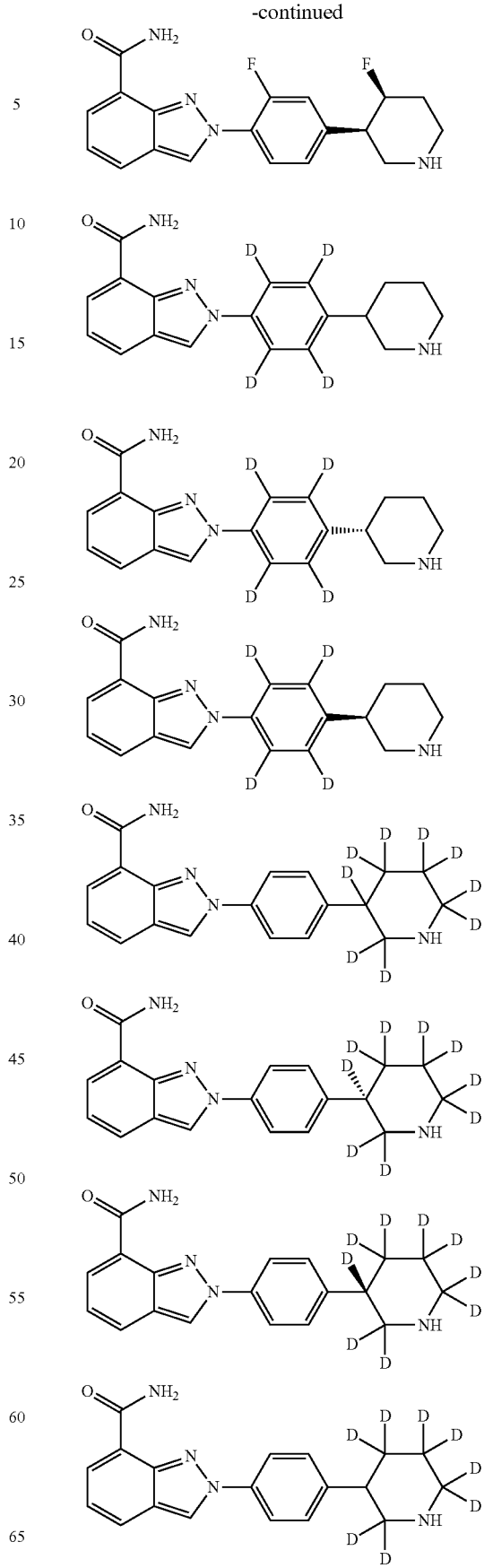

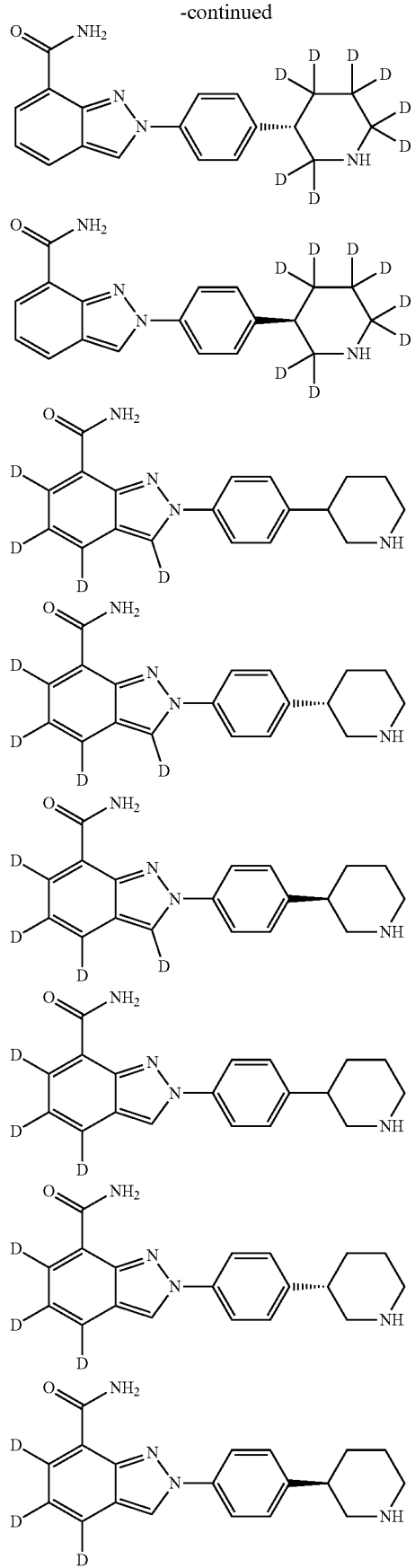
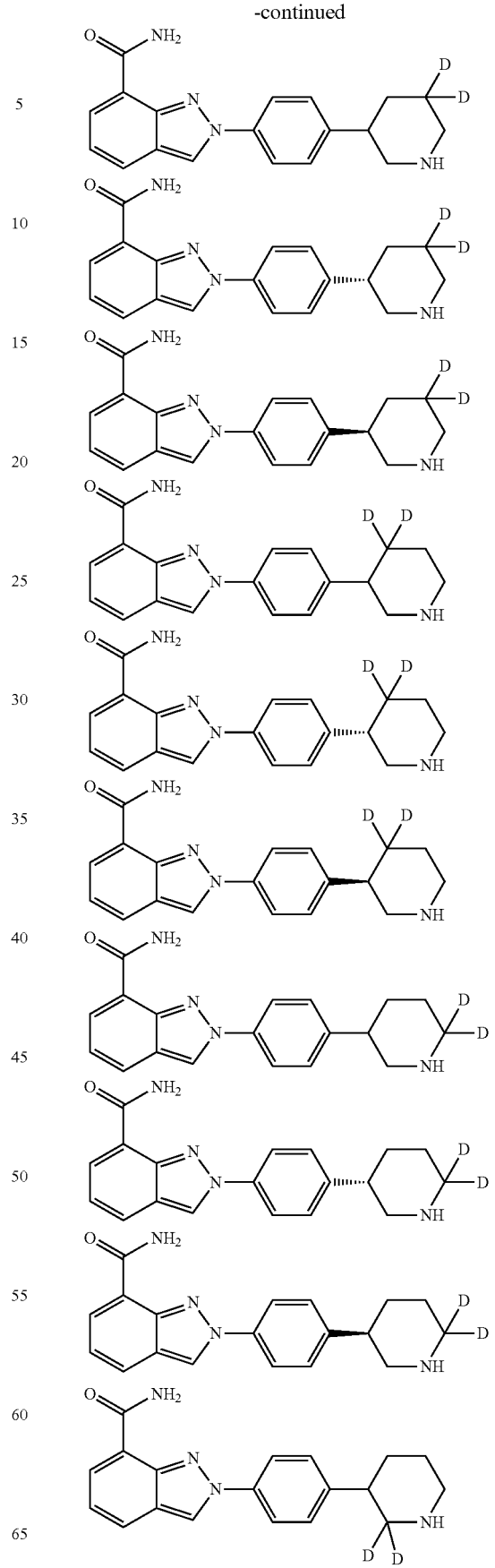

-continued

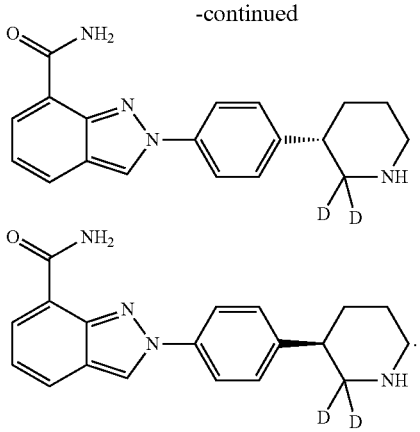

In some embodiments of the present disclosure, the compound as shown in general formula I can be obtained from compound 101 under the following chiral resolution conditions;

Compound 101

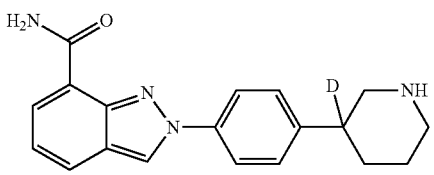

The chiral resolution conditions can include:
chiral column is Chrialpak AS-H 10 mm×250 mm, 5 μm;
column temperature is 40° C.;
mobile phase A is 0.1% DEA in hexane, and the percentage is the volume percentage;
mobile phase B is ethanol;
gradient is mobile phase A/mobile phase B=50/50, and the ratio is volume ratio;
flow rate is 6.0 mL/min;
detection wavelength is UV 210 nm;
the compound as shown in general formula (I) is respectively collected at RT of 10.7 minutes or 11.6 minutes.

In some aspects of the present disclosure, the compound as shown in general formula I can be a chiral compound in the compound 101 with a corresponding RT value of 5.8 minutes or 7.7 minutes under the following detection conditions;

Compound 101

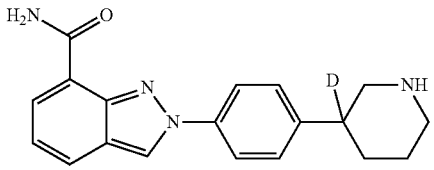

The detection conditions can include:
chiral column is chrialpak AS-H 4.6 mm×250 mm;
column temperature is 40° C.;
mobile phase A is 0.1% DEA in hexane, and the percentage is the volume percentage;
mobile phase B is ethanol;
gradient is mobile phase A/mobile phase B=50/50, and the ratio is the volume ratio,
flow rate is 1.0 mL/min;
detection wavelength is UV 210 nm.

In some embodiments of the present disclosure, the compound as shown in general formula I can be obtained from compound 102 under the following chiral resolution conditions.

Compound 102

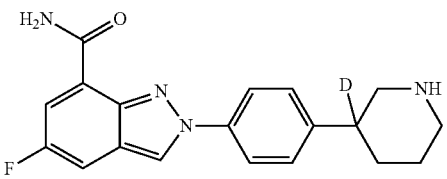

The chiral resolution conditions can include:
chiral column is Chrialpak AS-H 10 mm×250 mm, 5 μm;
column temperature is 40° C.;
mobile phase A is 0.1% DEA in hexane, and the percentage is the volume percentage;
mobile phase B is ethanol;
gradient is mobile phase A/mobile phase B=50/50, and the ratio is volume ratio;
flow rate is 6.0 mL/min;
detection wavelength is UV 210 nm;
the compound as shown in general formula (I) is respectively collected at RT of 12.2 minutes or 10.8 minutes.

In some embodiments of the present disclosure, the compound as shown in general formula I can be obtained from compound 103 under the following chiral resolution conditions.

Compound 103

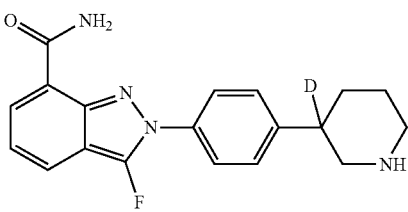

The chiral resolution conditions can include:
chiral column is Chrialpak AS-H 10 mm×250 mm, 5 μm;
column temperature is 40° C.;
mobile phase A is 0.1% DEA in hexane, and the percentage is the volume percentage;
mobile phase B is ethanol;
gradient is mobile phase A/mobile phase B=50/50, and the ratio is volume ratio;
flow rate is 6.0 mL/min;
detection wavelength is UV 210 nm;
the compound as shown in general formula (I) is respectively collected at RT of 15.2 minutes or 13.4 minutes.

In some embodiments of the present disclosure, the compound as shown in general formula I can be obtained from compound 104 under the following chiral resolution conditions.

Compound 104

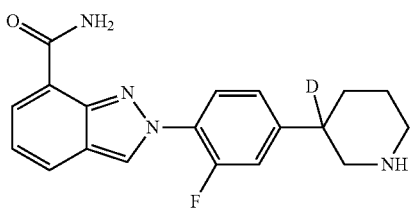

The chiral resolution conditions can include:
chiral column is Chrialpak AS-H 10 mm×250 mm, 5 µm;
column temperature is 40° C.;
mobile phase A is 0.1% DEA in hexane, and the percentage is the volume percentage;
mobile phase B is ethanol;
gradient is mobile phase A/mobile phase B=50/50, and the ratio is volume ratio;
flow rate is 6.0 mL/min;
detection wavelength is UV 210 nm;
the compound as shown in general formula (I) is respectively collected at RT of 12.3 minutes or 10.9 minutes.

In some embodiments of the present disclosure, the compound as shown in general formula I can be obtained from compound 105 under the following chiral resolution conditions.

Compound 105

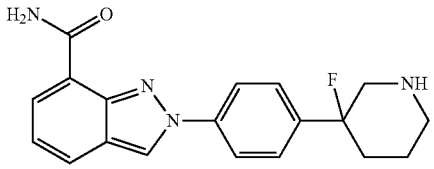

The chiral resolution conditions can include:
chiral column is CHIRALCEL OD-H 10 mm×250 mm, 5 µm;
column temperature is 40° C.;
mobile phase A is 0.1% DEA in hexane, and the percentage is the volume percentage;
mobile phase B is ethanol;
gradient is mobile phase A/mobile phase B=60/40, and the ratio is volume ratio;
flow rate is 3.0 mL/min;
detection wavelength is UV 210 nm;
the compound as shown in general formula (I) is respectively collected at RT of 20.5 minutes or 23.8 minutes.

In some aspects of the present disclosure, the compound as shown in general formula I can be a chiral compound in the compound 105 with a corresponding RT value of 15.02 minutes or 16.71 minutes under the following detection conditions;

Compound 105

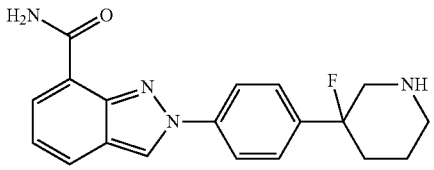

The detection conditions can include:
chiral column is CHIRALCEL OD-H 10 mm×250 mm, 5 µm;
column temperature is 40° C.;
mobile phase A is 0.1% DEA in hexane, and the percentage is the volume percentage;
mobile phase B is ethanol;
gradient is mobile phase A/mobile phase B=60/40, and the ratio is the volume ratio;
flow rate is 0.5 mL/min;
detection wavelength is UV 210 nm.

In some embodiments of the present disclosure, the compound as shown in general formula I can be obtained from compound 106 under the following chiral resolution conditions.

Compound 106

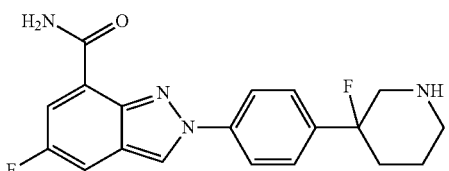

The resolution conditions can include:
chiral column is CHIRALCEL OD-H 10 mm×250 mm, 5 µm;
column temperature is 40° C.;
mobile phase A is 0.1% DEA in hexane, and the percentage is the volume percentage;
mobile phase B is ethanol;
gradient is mobile phase A/mobile phase B=60/40, and the ratio is volume ratio;
flow rate is 3.0 mL/min;
detection wavelength is UV 210 nm;
the compound as shown in general formula (I) is respectively collected at RT of 22.5 minutes or 24.5 minutes.

In some embodiments of the present disclosure, the compound as shown in general formula I can be obtained from compound 107 under the following chiral resolution conditions.

Compound 107

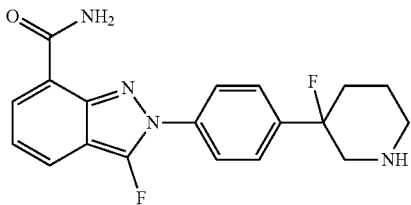

The chiral resolution conditions can include:
chiral column is CHIRALCEL OD-H 10 mm×250 mm, 5 µm;
column temperature is 40° C.;
mobile phase A is 0.1% DEA in hexane, and the percentage is the volume percentage;
mobile phase B is ethanol;
gradient is mobile phase A/mobile phase B=60/40, and the ratio is volume ratio;
flow rate is 3.0 mL/min;
detection wavelength is UV 210 nm;

the compound as shown in general formula (I) is respectively collected at RT of 24.3 minutes or 26.8 minutes.

In some embodiments of the present disclosure, the compound as shown in general formula I can be obtained from compound 108 under the following chiral resolution conditions.

Compound 108

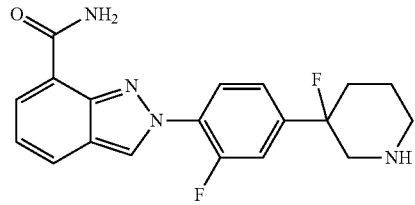

The chiral resolution conditions can include:
chiral column is CHIRALCEL OD-H 10 mm×250 mm, 5 µm;
column temperature is 40° C.;
mobile phase A is 0.1% DEA in hexane, and the percentage is the volume percentage;
mobile phase B is ethanol;
gradient is mobile phase A/mobile phase B=60/40, and the ratio is volume ratio;
flow rate is 3.0 mL/min;
detection wavelength is UV 210 nm;
the compound as shown in general formula (I) is respectively collected at RT of 21.3 minutes or 23.3 minutes.

In some embodiments of the present disclosure, the compound as shown in general formula I can be obtained from compound 109 under the following chiral resolution conditions.

Compound 109

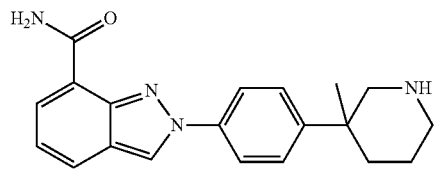

The chiral resolution conditions can include:
chiral column is Chrialpak AS-H 10 mm×250 mm, 5 µm;
column temperature is 40° C.;
mobile phase A is 0.1% DEA in hexane, and the percentage is the volume percentage;
mobile phase B is ethanol;
gradient is mobile phase A/mobile phase B=50/50, and the ratio is volume ratio;
flow rate is 6.0 mL/min;
detection wavelength is UV 210 nm;
the compound as shown in general formula (I) is respectively collected at RT of 13.6 minutes or 15.8 minutes.

In some aspects of the present disclosure, the compound as shown in general formula I can be a chiral compound in the compound 109 with a corresponding RT value of 8.9 minutes or 11.3 minutes under the following detection conditions;

Compound 109

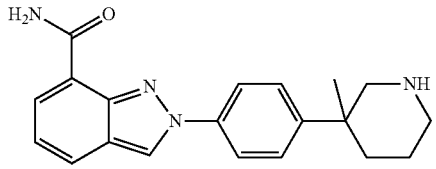

The detection conditions can include:
chiral column is Chrialpak AS-H 4.6 mm×250 mm, 5 µm;
column temperature is 40° C.;
mobile phase A is 0.1% DEA in hexane, and the percentage is the volume percentage;
mobile phase B is ethanol;
gradient is mobile phase A/mobile phase B=50/50, and the ratio is the volume ratio;
flow rate is 1.0 mL/min;
detection wavelength is UV 210 nm.

In some embodiments of the present disclosure, the compound as shown in general formula I can be obtained from compound 110 under the following chiral resolution conditions.

Compound 110

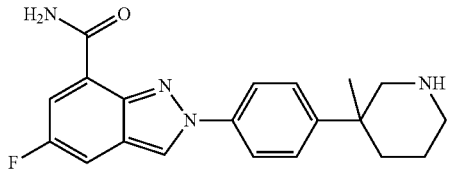

The chiral resolution conditions can include:
chiral column is Chrialpak AS-H 10 mm×250 mm, 5 µm;
column temperature is 40° C.;
mobile phase A is 0.1% DEA in hexane, and the percentage is the volume percentage;
mobile phase B is ethanol;
gradient is mobile phase A/mobile phase B=50/50, and the ratio is volume ratio;
flow rate is 6.0 mL/min;
detection wavelength is UV 210 nm;
the compound as shown in general formula (I) is respectively collected at RT of 16.7 minutes or 14.2 minutes.

In some embodiments of the present disclosure, the compound as shown in general formula I can be obtained from compound 111 under the following chiral resolution conditions.

Compound 111

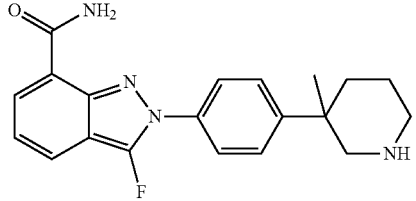

The chiral resolution conditions can include:
chiral column is Chrialpak AS-H 10 mm×250 mm, 5 μm;
column temperature is 40° C.;
mobile phase A is 0.1% DEA in hexane, and the percentage is the volume percentage;
mobile phase B is ethanol;
gradient is mobile phase A/mobile phase B=50/50, and the ratio is volume ratio;
flow rate is 6.0 mL/min;
detection wavelength is UV 210 nm;
the compound as shown in general formula (I) is respectively collected at RT of 18.7 minutes or 16.9 minutes.

In some embodiments of the present disclosure, the compound as shown in general formula I can be obtained from compound 112 under the following chiral resolution conditions.

Compound 112

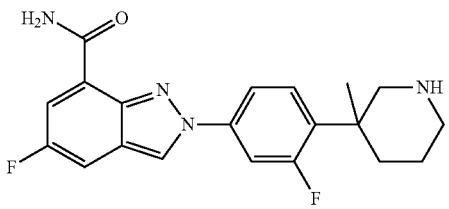

The chiral resolution conditions can include:
chiral column is Chrialpak AS-H 10 mm×250 mm, 5 μm;
column temperature is 40° C.;
mobile phase A is 0.1% DEA in hexane, and the percentage is the volume percentage;
mobile phase B is ethanol;
gradient is mobile phase A/mobile phase B=50/50, and the ratio is volume ratio;
flow rate is 6.0 mL/min;
detection wavelength is UV 210 nm;
the compound as shown in general formula (I) is respectively collected at RT of 15.8 minutes or 14.2 minutes.

Even if other chiral resolutions, purification methods, or detection methods are employed, they will fall into the protection scope of the present disclosure to obtain a single chiral compound at a corresponding retention time under the chiral separation or detection method described in the present disclosure.

In a second aspect, the disclosure also provides a process for preparing the compound as shown in general formula I, which comprises the following steps:

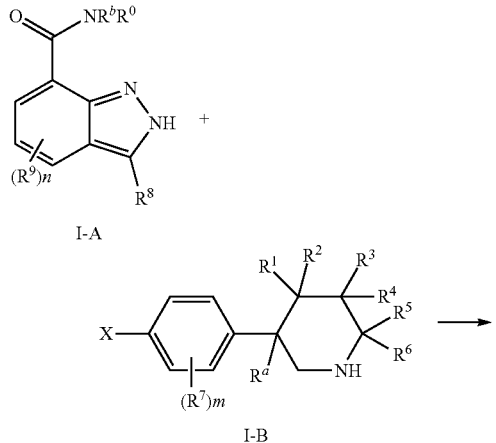

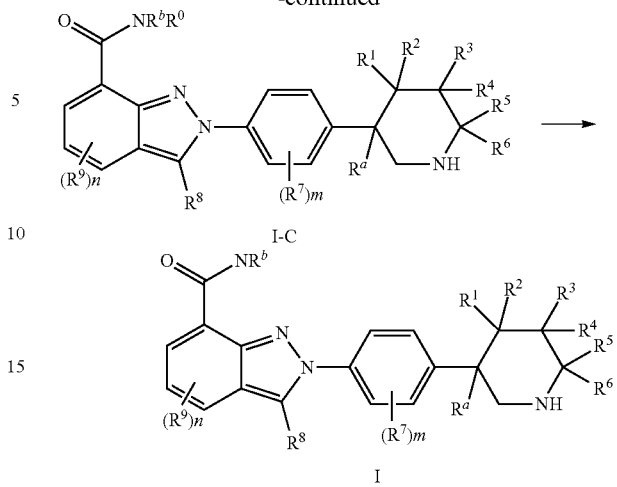

a1) coupling the compound of the formula I-A with the compound of the formula I-B under basic condition in presence of a metal catalyst to give the compound of general formula I-C;

b1) removing the protecting group of the compound of general formula I-C under acidic condition to give the compound as shown in general formula I;

wherein X is halogen, $R^0$ is an amino protecting group, and $R^a$, $R^b$, $R^1$, $R^2$, $R^3$, $R^4$, $R^5$, $R^6$, $R^7$, $R^8$, $R^9$, m and n are as defined above.

In the process of preparing the compound as shown in general formula I, X can be bromine.

In the process of preparing the compound as shown in general formula I, $R^0$ can be tert-butyl.

In the step a1, the reagent that provides the basic condition can be a common basic reagent for this type of reaction in the art, including organic bases and inorganic bases, and the organic bases can be selected from the group comprising of lithium hexamethyldisilazane, sodium hexamethyldisilazane, potassium hexamethyldisilazane, lithium diisopropylamide, n-butyllithium, sec-butyllithium, triethylamine, pyridine, 2,6-dimethylpyridine, N,N-diisopropylethylamine, potassium tert-butoxide, sodium tert-butoxide, lithium tert-butoxide, tetrabutyl ammonium fluoride and N-methylmorpholine. The inorganic bases can be selected from the group comprising of potassium carbonate, sodium carbonate, sodium bicarbonate, sodium hydroxide, potassium hydroxide, lithium hydroxide, cesium fluoride, cesium carbonate, lithium carbonate, potassium phosphate, sodium hydride and potassium hydride (e.g., potassium carbonate).

In the step a1, the metal catalyst can be a common catalyst for this type of reaction in the art, for example, selected from the group comprising of cuprous iodide, cuprous bromide, cuprous chloride, copper powder, cuprous oxide, copper(II) oxide, copper(II) bromide, copper(II) chloride, copper acetate, cuprous acetate, copper trifluoroacetate, copper trifluorosulfonate and ferric chloride (e.g., cuprous iodide).

In the step b1, the reagent that provides the acidic condition can be a common acidic reagent for this type of reaction in the art, including organic acids and inorganic acids, and the organic acid can be selected from the group comprising trifluoroacetic acid, methanesulfonic acid, trifluoromethanesulfonic acid, p-toluenesulfonic acid, benzenesulfonic acid, trichloroacetic acid, formic acid, acetic acid, and oxalic acid. The inorganic acid can be selected from the group comprising hydrochloric acid, sulfuric acid, sulfonic acid, phosphoric acid, and metaphosphoric acid (e.g., methanesulfonic acid).

In a third aspect, the present disclosure also provides a pharmaceutical composition comprising a therapeutically effective amount of the compound as shown in general formula I, the pharmaceutically acceptable salt thereof, the isomer thereof or the mixture form of the isomers, the solvate thereof, the polymorph thereof, the stable isotope derivative thereof or the prodrug thereof, and a pharmaceutically acceptable carrier, diluent or excipient.

The present disclosure also provides a use of the compound as shown in general formula I, the pharmaceutically acceptable salt thereof, the isomer thereof or the mixture form of the isomers, the solvate thereof, the polymorph thereof, the stable isotope derivative thereof or the prodrug thereof, or the pharmaceutical composition for manufacturing a medicament for preventing, relieving and/or treating diseases which can be alleviated by PARP inhibitors.

The present disclosure also provides a use of the compound as shown in general formula I, the pharmaceutically acceptable salt thereof, the isomer thereof or the mixture form of the isomers, the solvate thereof, the polymorph thereof, the stable isotope derivative thereof or the prodrug thereof, or the pharmaceutical composition for manufacturing PARP inhibitors.

The present disclosure also provides a use of the compound as shown in general formula I, the pharmaceutically acceptable salt thereof, the isomer thereof or the mixture form of the isomers, the solvate thereof, the polymorph thereof, the stable isotope derivative thereof or the prodrug thereof, or the pharmaceutical composition for manufacturing a medicament for preventing, relieving and/or treating cancers, inflammatory diseases, vascular diseases, stroke, renal failure, diabetes, Parkinson's disease, septic shock, neurotoxicity, ischemic shock or injury, transplant rejection, reperfusion injury, retinal injury, UV-induced skin damage, viral infection or multiple sclerosis.

The present disclosure also provides a use of the compound as shown in general formula I, the pharmaceutically acceptable salt thereof, the isomer thereof or the mixture form of the isomers, the solvate thereof, the polymorph thereof, the stable isotope derivative thereof or the prodrug thereof, or the pharmaceutical composition for manufacturing an auxiliary medicament for treating cancers or for manufacturing a medicament for strengthening radiotherapy and/or chemotherapy on cancers treatment.

The present disclosure also provides a use of the compound as shown in general formula I, the pharmaceutically acceptable salt thereof, the isomer thereof or the mixture form of the isomers, the solvate thereof, the polymorph thereof, the stable isotope derivative thereof or the prodrug thereof, or the pharmaceutical composition for manufacturing a medicament for treating cancers, wherein the cancers are selected from breast cancer, ovarian cancer, prostate cancer, melanoma, brain tumor (e.g., glioma), nasopharyngeal carcinoma, esophageal cancer, gastric cancer, liver cancer, pancreatic cancer, colorectal cancer (e.g., colon cancer, rectal cancer, etc.), lung cancer (e.g., small cell lung cancer, non-small cell lung cancer, squamous cell carcinoma, undifferentiated carcinoma, etc.), renal carcinoma, skin cancer, glioblastoma, neuroblastoma, sarcoma, liposarcoma, osteochondroma, osteocarcinoma, osteosarcoma, seminoma, testicular tumor, uterine tumor (e.g., cervical cancer, endometrial cancer, etc.), head and neck tumor (e.g., laryngeal cancer, pharyngeal cancer, tongue cancer, etc.), multiple myeloma, malignant lymphoma (e.g., reticulum cell sarcoma, hedgerow lymphosarcoma, Hodgkin's lymphoma, mantle cell lymphoma, etc.), polycythemia vera, leukemia (e.g., acute granulocytic leukemia, chronic granulocytic leukemia, acute lymphoblastic leukemia, chronic lymphoblastic leukemia, etc.), thyroid tumor, ureteral tumor, bladder tumor, gallbladder cancer, cholangiocarcinoma, chorionic epithelial cancer or pediatric tumor (e.g., neuroblastoma, embryonic testicular cancer, retinoblastoma, etc.).

The present disclosure also provides a use of the compound as shown in general formula I, the pharmaceutically acceptable salt thereof, the isomer thereof or the mixture form of the isomers, the solvate thereof, the polymorph thereof, the stable isotope derivative thereof or the prodrug thereof, or the pharmaceutical composition for manufacturing a medicament for treating cancers. The cancers can be selected from solid tumor, acute or chronic leukemia, lymphoma, central nervous system cancer, brain cancer, hematogenous cancer, peritoneal cancer, gastric cancer, lung cancer, cancer lacking homologous recombination-dependent DNA double-strand break repair activity, cancer with defective or mutant phenotype on BRCA-1 or BRCA2 (such as breast cancer, ovarian cancer, prostate cancer and pancreatic cancer).

The compound as shown in general formula I, the pharmaceutically acceptable salt thereof, the isomer thereof or the mixture form of the isomers, the solvate thereof, the polymorph thereof, the stable isotope derivative thereof or the prodrug thereof, or the pharmaceutical composition can be used in combination with one or more than one other anticancer agents. The anticancer agents are selected from alkylating agents, platinum drugs, topoisomerase inhibitors, metabolic antagonists, alkaloids, antibody drugs, hormone anticancer agents, proteasome inhibitors, HDAC inhibitors, CDK inhibitors, VEGFR or EGFR inhibitors, mTOR inhibitors, PI3K inhibitors, B-Raf inhibitors, PARP inhibitors, c-Met kinase inhibitors, ALK inhibitors, AKT inhibitors, ABL inhibitors, FLT3 inhibitors, PD-1 monoclonal antibodies and PD-L1 monoclonal antibodies.

The present disclosure also provides a use of the compound as shown in general formula I, the pharmaceutically acceptable salt thereof, the isomer thereof or the mixture form of the isomers, the solvate thereof, the polymorph thereof, the stable isotope derivative thereof or the prodrug thereof, or the pharmaceutical composition for manufacturing a medicament for treating cancers, wherein the medicament can be used in combination with one or more than one other anticancer agents. The anticancer agents are selected from alkylating agents (e.g., cyclophosphamide, chlormethine hydrochloride, dibromomannitol, carmustine, dacarbazine, melphalan, etc.), platinum complexes (e.g., cisplatin, carboplatin, cyclothioplatinum, nedaplatin, oxaliplatin, lobaplatin, etc.), metabolic antagonists (e.g., methotrexate, 5-fluorouracil, capecitabine, pemetrexed, etc.), alkaloids (e.g., docetaxel, paclitaxel, vinblastine, etc.), antibody drugs (e.g., trastuzumab, partrozumab, bevacizumab, etc.), hormonal anticancer agents (e.g., leuprorelin, dutasteride, dexamethasone, etc.), proteasome inhibitors (e.g., boraxzomib, ixazomib, lenalidomide, etc.), CDK inhibitors (e.g., palbociclib, ribociclib, etc.), VEGFR or EGFR inhibitors (e.g., alfatinib, imatinib, gefitinib, erlotinib, etc.), m-TOR inhibitors (e.g., everolimus, sirolimus, etc.), PI3K inhibitors (e.g., idelalisib, etc.), B-Raf inhibitors (e.g., sorafenib, verofeni, rivarofini, etc.), PARP inhibitors (e.g., olaparib, niraparib, etc.), c-Met kinase inhibitors (e.g., crizotinib, etc.), ALK inhibitors (e.g., ceritinib, alectinib, etc.), AKT inhibitors (e.g., perifosine, etc.), ABL inhibitors, FLT3 inhibitors, PD-1 monoclonal antibodies (e.g., Opdivo, Keytruda, etc.) and PD-L1 monoclonal antibodies (Atezolizumab).

Unless otherwise stated to the contrary, the terms used in the specification and claims have the following definitions.

The term "alkyl" refers to a saturated aliphatic hydrocarbon groups, including linear or branched groups of 1 to 20 carbon atoms, preferably 1 to 10 carbon atoms, more preferably 1 to 8 carbon atoms, and non-limiting examples include but are not limited to methyl, ethyl, n-propyl, n-butyl, isobutyl, tert-butyl, sec-butyl, n-pentyl, 2-methylbutyl, 3-methylbutyl, 1,1-dimethylpropyl, 1,2-dimethylpropyl, 2,2-dimethylpropyl, 1-ethylpropyl, n-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1-ethyl-2-methylpropyl, n-heptyl, 2-methylhexyl, 3-methylhexyl, 4-methylhexyl, 5-methylhexyl, 2,2-dimethylpentyl, 2,3-dimethylpentyl, 2,3-dimethylpentyl, 2,4-dimethylpentyl, 3,3-dimethylpentyl, 3,4-dimethylpentyl, 2-ethylpentyl, 3-ethylpentyl, octyl, nonyl, decyl, undecyl, dodecyl, and various isomers thereof, and the like. The alkyl can be substituted or unsubstituted and can be substituted at any available junction, and the substituent is preferably one or more than one groups, independently selected from alkyl, halogen, hydroxyl, mercapto, cyano, alkenyl, alkynyl, alkoxy, alkylthio, alkylamino, nitro, cycloalkyl, heterocycloalkyl, aryl, heteroaryl, cycloalkyloxy, heterocycloalkyloxy, cycloalkylthio, heterocycloalkylthio, oxo, amino, haloalkyl, hydroxyalkyl, carboxyl or carboxylate group, etc. When "alkyl" and its prefix are used herein, both linear and branched saturated carbon bonds are included.

The term "cycloalkyl" refers to a saturated or partially unsaturated monocyclic or polycyclic group comprising from 3 to 20 carbon atoms, preferably 3 to 12 carbon atoms, more preferably 3 to 10 carbon atoms, and most preferably 3 to 6 carbon atoms. Non-limiting examples of monocyclic cycloalkyl include, but are not limited to, cyclopropyl, cyclobutyl, cyclopentyl, cyclopentenyl, cyclohexyl, cyclohexenyl, cyclohexadiene, cycloheptyl, cyclooctyl, and the like. Non-limiting examples of polycyclic cycloalkyl include, but are not limited to, spirocycloalkyl, fused cycloalkyl and bridged cycloalkyl. Cycloalkyl can be substituted or unsubstituted, and the substituent is preferably one or more than one groups, independently selected from alkyl, halogen, hydroxyl, mercapto, cyano, alkenyl, alkynyl, alkoxy, alkylthio, alkylamino, nitro, cycloalkyl, heterocycloalkyl, aryl, heteroaryl, cycloalkoxy, heterocycloalkoxy, cycloalkoxy, cycloalkoxy, cycloalkoxy, cycloalkylthio, heterocycloalkylthio, oxo, amino, haloalkyl, hydroxyalkyl, carboxyl or carboxylate groups, and the like.

The term "halogen" refers to fluorine, chlorine, bromine or iodine, preferably bromine or iodine.

The term "substituted" means that one or more than one hydrogen or deuterium atoms in the group, preferably 1 to 5 hydrogen or deuterium atoms, are independently substituted by a corresponding number of substituents.

The term "pharmaceutically acceptable salt" refers to a salt that can retain the biological effectiveness of the free base without other toxic and side effects, and can be an acidic salt, a basic salt or an amphoteric salt. Non-limiting examples include, but are not limited to, acidic salts including hydrochloride, hydrobromide, sulfate, pyrosulfate, bisulfate, sulfite, bisulfite, phosphate, monohydrogen phosphate, dihydrogen phosphate, metaphosphate, pyrophosphate, nitrate, acetate, propionate, caprate, octanoate, formate, acrylate, isobutyrate, hexanoate, heptanoate, oxalate, malonate, succinate, suberate, benzoate, methyl benzoate, phthalate, maleate, methanesulfonate, p-toluenesulfonate, benzenesulfonate, (D, L)-tartrate, citrate, maleate, (D,L-)malate, fumarate, stearate, oleate, cinnamate, laurate, glutamate, aspartate, triflate, mandelate, ascorbate, salicylate, and the like. When the compound of the present disclosure contains acidic groups, pharmaceutically acceptable salts thereof can further include alkali metal salts (e.g., sodium salt or potassium salt), alkaline earth metal salts (e.g., calcium salt or magnesium salt), organic base salts (e.g., alkylaromatics, amino acids, etc.).

The term "solvate" refers to an aggregate (or associated complex) formed by one or more than one solvent molecules with a compound of the present disclosure. Solvents of the formed solvate include, but are not limited to, water, dimethyl sulfoxide, methanol, ethanol, isopropanol, acetic acid, and the like.

The term "polymorph" refers to different solid crystalline phases generated by the presence of two or more different molecular arrangements in the solid-state of the compound of the present disclosure, which may exist as a single crystal form or a mixture of polycrystal forms.

The term "stable isotope derivative" refers to an isotope substituted derivative obtained by substituting any hydrogen atom of the compound of the present disclosure with 1 to 5 deuterium atoms, or an isotope substituted derivative obtained by replacing any carbon atom of the compound of the present disclosure with 1 to 3 $C^{14}$ atoms, or an isotope derivative obtained by replacing any oxygen atom with 1 to 3 $O^{18}$ atoms of the compound of the present disclosure.

The term "prodrug" refers to a compound that can be converted to a bioactive compound of the present disclosure under physiological conditions (e.g., in vivo) or by solvent decomposition, and can be understood to be a pharmaceutically acceptable metabolic precursor. The prodrug can be inactive or less active substances than active parent compound but it can be rapidly converted in vivo to produce the parent compound of the present disclosure, which can improve their solubility in animals as well as metabolic characteristics. The prodrug includes, for example, amino protecting groups, carboxyl protecting groups, phospholipids, and the like.

The term "pharmaceutical composition" refers to a mixture of one or more than one compounds described herein or pharmaceutically acceptable salts or prodrugs thereof and other chemical components, as well as other components such as physiologically acceptable carriers and excipients. The purpose of the pharmaceutical composition is to promote the administration of the organism and to facilitate absorption of the active ingredient and exert biological activity.

The term "isomer" refers to a stereoisomer, including an enantiomer and a diastereomer, and cis/trans isomer is one of the diastereomers. The isomer of the present compound can be their enantiomers, diastereomers, and any mixture thereof, including the formation and presence of free or salt forms.

The abbreviations used here for protecting groups, amino acids and other compounds are the commonly used and recognized, unless otherwise specified, or refer to IUPAC-IUBC Commission on Biochemical Nomenclature (See *Biochem.* 1972, 11, 942-944).

Without violating the common knowledge in the art, the above-mentioned preferred conditions can be combined arbitrarily to obtain various preferred embodiments of the present disclosure.

The reagents and starting materials used in the present disclosure are commercially available.

The positive and progressive effect of the disclosure is that the compound of the present disclosure has vigorous PARP inhibitory activity and can be used for treating diseases related to PARP, such as cancers, inflammatory diseases, and the like.

BRIEF DESCRIPTION OF DRAWINGS

FIG. 1 shows the inhibitory effects on tumor volumes in MDA-MB-436 cancer cells of vehicle group, compound of example 23 and Niraparib.

EXAMPLES

The following examples further describe the present disclosure, but these examples should not limit the scope of the present disclosure.

In the embodiment of the disclosure, the experimental methods without specifying specific conditions are generally in accordance with conventional methods and conditions, or in accordance with the conditions recommended by the manufacturers of raw materials or commodities. The reagents without specific sources are conventional reagents purchased from the market.

All compounds of the present disclosure can be determined by nuclear magnetic resonance (NMR) or mass spectrometry (MS). The NMR shift (δ) is recorded in units of 10-6 (ppm). The NMR measuring instrument is Bruker AVANCE-400 spectrometer. The deuterated solvents are deuterated chloroform ($CDCl_3$), deuterated methanol (MeOD) or deuterated dimethyl sulfoxide (DMSO-$d_6$). The internal standard is tetramethylsilane (TMS).

Low-resolution mass spectrometry (MS) is determined by Agilent 6120 quadruple LCMS mass spectrometer.

The HPLC purity is determined by Agilent HPLC Agilent 1260/1220 chromatograph (Agilent Zorb Ax BonusRP 3.5μ m×4.6 mm×150 mm or Boston pHlex ODS 4.6 mm×150 mm×3 μm).

The compound of the present disclosure and the intermediate thereof can be isolated and purified by conventional preparative HPLC, silica gel plate, column chromatography, or using a rapid separator.

The thin-layer chromatography silica gel plate uses Yantai Huanghai, Yantai Xinnuo Chemical Industry HSGF254, or Qingdao GF254 silica gel plate. The silica gel plate used for thin-layer chromatography (TLC) is 2.5×5 cm, 0.2 mm-0.25 mm, and the thin-layer chromatography separation (Prep-TLC) used for purifying products is 1 mm or 0.4 mm-0.5 mm, 20×20 cm.

Column chromatography (silica gel column chromatography) is generally used in the sizes of 100-200 mesh or 200-300 mesh or 300-400 mesh.

The instrument used in the rapid separator is Agela Technologies MP200, and the column is generally Flash column silica-CS (12 g-330 g).

The instrument used for preparative HPLC (Prep-HPLC) is Gilson GX-281, and the column model is Welch Ultimate XB-C18 21.2 mm×250 mm×10 μm.

The chiral columns are CHIRALCEL OD-H, OJ-H or CHIRALPAK AD-H, AS-H 4.6 mm×250 mm×5 μm, and the preparation column types are CHIRALCEL OD-H, OJ-H or CHIRALPAK AD-H, AS-H 10 mm×250 mm×5 μm.

The known starting materials of the present disclosure can be synthesized by methods known in the art, or purchased from suppliers such as Sigma-Aldrich, ACROS, Alfa Aesar, TCI, J&K Scientific, energy-chemical, Accela ChemBio, Macklin, Siyanbio chemical companies and the like.

Anhydrous solvents such as anhydrous tetrahydrofuran, anhydrous dichloromethane or anhydrous N,N-dimethylacetamide are commercially available from the above chemical companies.

Unless otherwise specified in the examples, the reaction is generally carried out under nitrogen or argon atmosphere. The nitrogen or argon atmosphere refers to that the reaction flask is connected to a balloon of nitrogen or argon having a volume of about 1 L and subjected to three pumping displacements.

In the examples, unless otherwise specified, the reaction temperature is room temperature, and the temperature is 15-25° C.

The reactions in the examples are generally monitored by LCMS or TLC, wherein the LCMS instrument is as described above. The developing solvent system used for TLC is generally: dichloromethane and methanol, petroleum ether and ethyl acetate, dichloromethane and ethyl acetate, petroleum ether and dichloromethane, ethyl acetate and methanol, etc. The volume ratio of the solvent is adjusted according to the polarity of the compound and a small amount (0.1%-10%) of base (e.g. triethylamine or 37% ammonia water, etc.) or acid (e.g. acetic acid, etc.) can also be added for adjustment.

The compounds can be purified by Prep-TLC, column chromatography or Agela preparation system. The eluted solvent system is generally dichloromethane and methanol, petroleum ether and ethyl acetate, dichloromethane and ethyl acetate, petroleum ether and dichloromethane, ethyl acetate and methanol, etc. The volume ratio of the solvent is adjusted according to the polarity of the compound. A small amount (0.1%-10%) of base (e.g. triethylamine or 37% ammonia water, etc.) or acid (e.g. acetic acid, etc.) can also be added for adjustment.

The following abbreviations are used throughout the present disclosure:
DMAc: N,N-dimethylacetamide
DMSO: dimethyl sulfoxide
MTBE: methyl tert-butyl ether
THF: tetrahydrofuran
PE: petroleum ether
EA: ethyl acetate
DAST: diethylaminosulfur trifluoride
$(Boc)_2O$: di-tert-butyl dicarbonate
$NaHCO_3$: sodium bicarbonate
NaOH: sodium hydroxide
NaH: sodium hydride
DEA: diethylamine
Hexane: n-hexane
RT: retention time
SFC: Supercritical Fluid Chromatography
Prep-TLC: preparative thin-layer chromatography
Prep-HPLC: preparative high-performance liquid chromatography.

Example 1

2-(4-(Piperidin-3-D-3-yl) phenyl)-2H-indazole-7-carboxamide

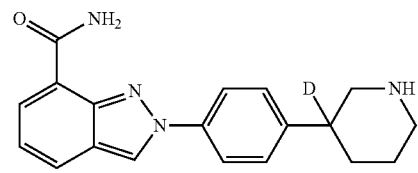

-continued

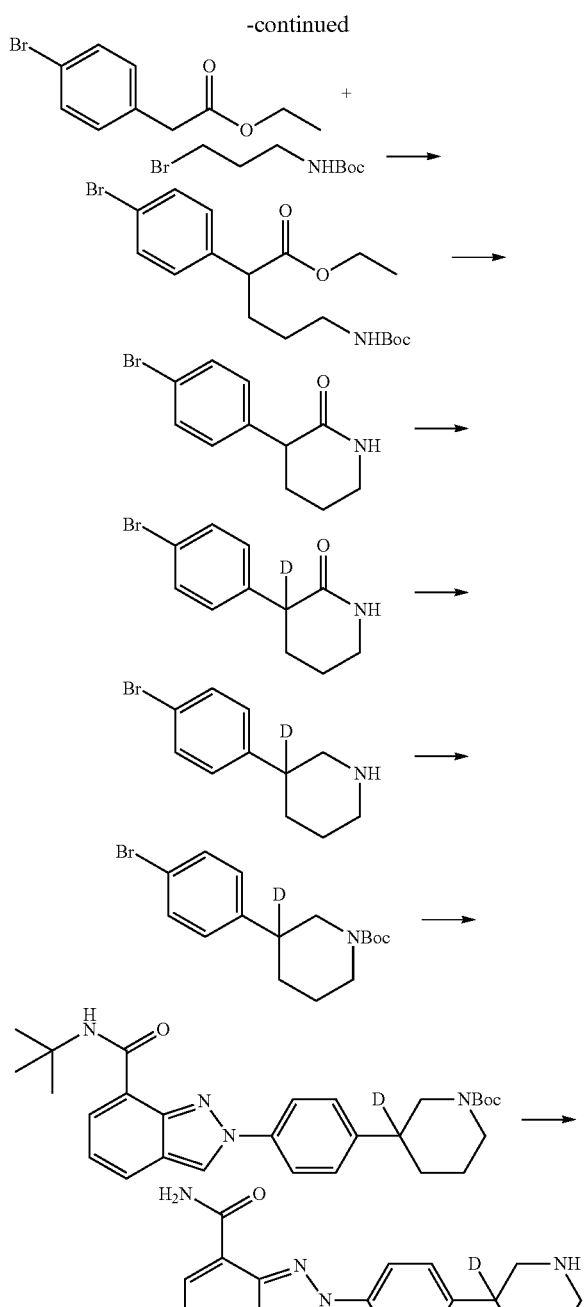

Step 1) ethyl 2-(4-bromophenyl)-5-((tert-butoxycarbonyl) amino) pentanoate

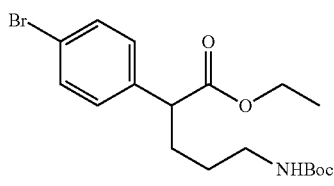

To a solution of ethyl 2-(4-bromophenyl) acetate (24.3 g, 0.1 mol) in DMSO (60 mL) was added NaH (60% dispersion in mineral oil, 4.3 g, 0.107 mol) in portions at room temperature. After completion of the addition, the solution was stirred for 20 minutes, and a solution of tert-butyl (3-bromopropyl)carbamate (21.4 g, 0.09 mol) in DMSO (60 mL) was added dropwise, and after the completion of the addition, the mixture was heated to 40-45° C. and reacted with stirring for 2 hours. TLC showed a new substance was formed, and a small amount of starting materials remained (TLC condition: EA:PE=1:10). Then the mixture was quenched with 100 mL of ammonium chloride solution, and extracted with ethyl acetate (300 mL+100 mL). The organic phase was concentrated to give a crude product (37.0 g), which was mixed with 100-200 mesh silica gel and purified by column chromatography (elution conditions: gradient elution from petroleum ether to ethyl acetate: petroleum ether=1:4) to give ethyl 2-(4-bromophenyl)-5-((tert-butoxycarbonyl)amino)pentanoate as oil (18.0 g, 45% yield).

MS (ESI), m/z, 300.0 [M-100]⁺.

¹H NMR (400 MHz, CDCl₃) δ (ppm) 7.48-7.43 (m, 2H), 7.22-7.17 (m, 2H), 4.52 (s, 1H), 4.13 (dd, J=13.6, 7.1 Hz, 2H), 3.52 (s, 1H), 3.13 (s, 2H), 2.07 (s, 1H), 1.87-1.73 (m, 1H), 1.47-1.37 (m, 4H), 1.22 (t, J=7.1 Hz, 3H).

Step 2) 3-(4-bromophenyl) piperidin-2-one

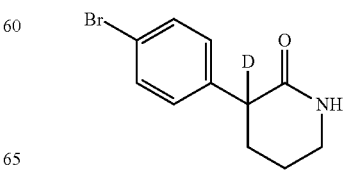

To a solution of ethyl 2-(4-bromophenyl)-5-((tert-butoxycarbonyl)amino)pentanoate (45.0 g, 0.11 mol) in 200 mL of ethanol was added a 2 M hydrochloric acid-ethanol solution (200 mL) dropwise. After completion of the addition, the reaction was reacted with stirring for 30 minutes. LC-MS showed that the raw materials disappeared, and the mixture was concentrated. The obtained residue was mixed with potassium carbonate (23.0 g, 0.15 mol), and heated to reflux in ethanol (500 mL) for 18 hours. LC-MS showed that the raw materials disappeared, and most of the ethanol was concentrated, the residue was mixed with 200 mL of water, the pH was adjusted to 1-2 with 6 N hydrochloric acid, the mixture was extracted with ethyl acetate (500 mL×2), dried and concentrated. The residue was slurried with petroleum ether and dried in vacuo to give 3-(4-bromophenyl) piperidin-2-one as white solid (23.7 g, 83% yield).

MS (ESI), m/z, 254.0 [M+H]⁺.

¹H NMR (400 MHz, MeOD) δ (ppm) 7.53-7.42 (m, 2H), 7.23-7.13 (m, 2H), 3.64 (dd, J=8.2, 6.2 Hz, 1H), 3.49-3.35 (m, 2H), 2.19 (tdd, J=8.7, 6.1, 2.6 Hz, 1H), 1.96-1.75 (m, 3H).

Step 3) 3-(4-bromophenyl) piperidin-3-D-2-one 3-(4-Bromophenyl) piperidine-2-one (7.6 g, 30 mmol) was mixed in deuterated methanol (100 g) and heated to 40-45° C. under nitrogen atmosphere. Then sodium methoxide (3.2 g, 60 mmol) was added into the above mixture, and the reaction was reacted at 40-45° C. for 16 hours. LCMS showed that the deuteration rate was 90%, and the reaction mixture was cooled to 20-25° C., quenched with 100 mL of ammonium chloride solution, extracted with ethyl acetate (100 mL×2), dried, concentrated to give a crude product, which was slurried with petroleum ether and filtered to obtain 7.0 g of 3-(4-bromophenyl)piperidine-3-D-2-one as white solid, with yield of 92%, deuteration rate of 92% by LCMS and deuteration rate of 94% by NMR.

MS (ESI), m/z, 255.0 [M+H]+.

1H NMR (400 MHz, MeOD) δ (ppm) 7.46 (d, J=8.4 Hz, 2H), 7.15 (d, J=8.4 Hz, 2H), 3.38 (dd, J=12.6, 7.0 Hz, 2H), 2.15 (d, J=3.6 Hz, 1H), 1.97-1.70 (m, 3H).

Step 4) 3-(4-bromophenyl) piperidine-D-3

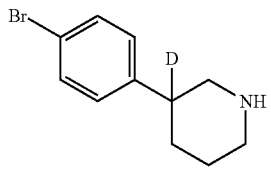 [SMILES: [2H]C1(c2ccc(Br)cc2)CCCNC1]

To a solution of 3-(4-bromophenyl)piperidin-3-D-2-one (7.0 g, 27.5 mmol) in tetrahydrofuran (140 mL) was added sodium borohydride (3.15 g, 82.9 mmol) in portions at 0-5° C., and reacted with stirring for 30 minutes. Then ethanol was added and reacted with stirring for 30 minutes, and boron trifluoride diethyl ether (11.7 g, 82.9 mmol) was added dropwise. After completion of the addition, the temperature was raised to 20-25° C. After stirring for 18 hours, LCMS showed that most of the raw materials disappeared. The reaction solution was quenched with 100 mL of water, and extracted with ethyl acetate (200 mL×2). The organic phase was concentrated. The residue was mixed with 30 mL of concentrated hydrochloric acid and 60 mL of methanol and reacted for 30 minutes at 40-45° C. The reaction mixture was diluted with water, the pH was neutralized to 8-9 with 2 N NaOH aqueous solution, extracted with ethyl acetate, dried, and concentrated to obtain a crude 3-(4-bromophenyl) piperidine-D-3 (6.0 g, 90% yield).

MS (ESI), m/z, 241.0 [M+H]+.

Step 5) tert-butyl 3-(4-bromophenyl) piperidine-3-D-1-carboxylate

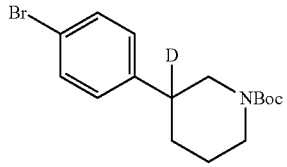 [SMILES: [2H]C1(c2ccc(Br)cc2)CCCN(C(=O)OC(C)(C)C)C1]

To a solution of 3-(4-bromophenyl) piperidine-3-D (1.1 g, 3.3 mmol) and 1 N NaOH (10 mL) in MTBE (20 mL) was added Boc2O (0.73 g, 3.3 mmol), and stirred for 1 hour after completion of the addition, followed by addition of 50 mL of MTBE. The organic phases were collected, dried and concentrated to obtain a crude tert-butyl 3-(4-bromophenyl) piperidine-3-D-1-carboxylate (1.22 g, 95% yield).

MS (ESI), m/z, 241.0 [M+H]+.

Step 6) tert-butyl 3-(4-(7-(tert-butylcarbamoyl)-2H-indazol-2-yl) phenyl)-piperidine-3-D-1-carboxylate

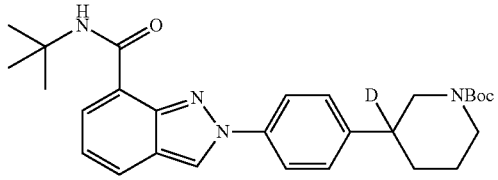 [SMILES: [2H]C1(c2ccc(-n3cc4cccc(C(=O)NC(C)(C)C)c4n3)cc2)CCCN(C(=O)OC(C)(C)C)C1]

The mixture of tert-butyl 3-(4-bromophenyl) piperidine-3-D-1-carboxylate (1.0 g, 3 mmol), N-tert-butyl-1H-indazole-7-carboxamide (0.65 g, 3 mmol), potassium carbonate (1.2 g, 9 mmol), cuprous bromide (0.1 g, 0.7 mmol) and 8-hydroxyquinoline (0.1 g, 0.68 mmol) in DMAc (30 mL) was heated to 110-120° C. and reacted with stirring for 18 hours under nitrogen atmosphere. LCMS showed that part of the raw materials remained, and the product was formed. The mixture was cooled to room temperature, quenched with 50 mL of water, and extracted with MTBE (200 mL×2). The organic phase was washed with citric acid aqueous solution, dried, and concentrated to obtain a crude tert-butyl 3-(4-(7-(tert-butylcarbamoyl)-2H-indazol-2-yl)phenyl)-piperidine-3-D-1-carboxylate as a foamy solid (1.6 g), which was used directly in the next step.

Step 7) 2-(4-(piperidin-3-D-3-yl) phenyl)-2H-indazole-7-carboxamide

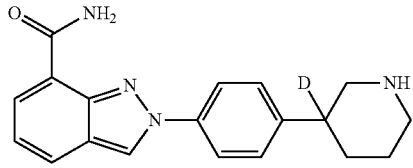 [SMILES: [2H]C1(c2ccc(-n3cc4cccc(C(N)=O)c4n3)cc2)CCCNC1]

To a mixture of tert-butyl 3-(4-(7-(tert-butylcarbamoyl)-2H-indazol-2-yl) phenyl)-piperidine-3-D-1-carboxylate in toluene (3 mL) was added methanesulfonic acid (6 mL) at room temperature. After completion of the addition, the mixture was heated to 40-45° C. and reacted with stirring for 30 minutes. LCMS showed that the raw materials disappeared and the product was formed. Then the mixture was diluted with water, and the pH was neutralized to 8-9 with 2 N NaOH solution, extracted with ethyl acetate (100 mL×2), dried and concentrated to obtain 1.1 g of a crude product, which was purified by HPLC to give 114 mg of 2-(4-(piperidin-3-d-3-yl) phenyl)-2H-indazole-7-carboxamide as the crude product. The crude product can be heated with 64 mg of p-toluenesulfonic acid in ethanol until dissolved completely, followed by concentration to remove ethanol. The residue was slurried with tetrahydrofuran, filtered and dried to obtain 110 mg of p-toluenesulfonate as the product.

MS (ESI), m/z, 322.2 [M+H]+.

1H NMR (400 MHz, MeOD) δ (ppm) 9.00 (s, 1H), 8.18 (dd, J=7.0, 0.8 Hz, 1H), 8.05 (t, J=9.1 Hz, 3H), 7.74 (d, J=8.2

Hz, 2H), 7.53 (d, J=8.6 Hz, 2H), 7.34-7.17 (m, 3H), 3.48 (d, J=12.3 Hz, 2H), 3.22-3.01 (m, 2H), 2.37 (s, 3H), 2.09 (d, J=10.1 Hz, 2H), 1.99-1.80 (m, 2H).

Examples 2 & 3

(R or S)-2-(4-(piperidin-3-D-3-yl) phenyl)-2H-indazole-7-carboxamide

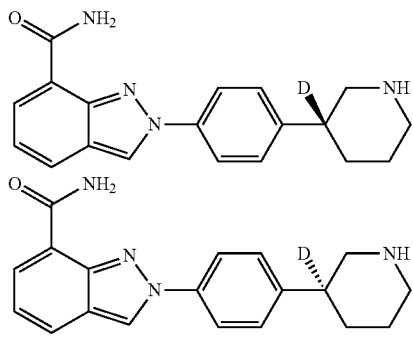

The racemic compound obtained in example 1 was separated by chiral column Chiralpak AS-H (10 mm×250 mm, 5 μm) at a column temperature of 40° C. Mobile phase A was 0.1% DEA in hexane (v/v), mobile phase B was ethanol, running time was 30 minutes, gradient mobile was phase A/mobile phase B (50/50, v/v), flow rate was 6.0 mL/min and detection wavelength was UV 210 nm. Two single-configuration compounds were separated and collected at RT of 10.7 minutes (compound of example 2) and 11.6 minutes (compound of example 3), respectively. The compounds were detected by chiral column Chrialpak AS-H (4.6 mm×250 mm) at a column temperature of 40° C. Mobile phase A was 0.1% DEA in hexane (v/v), mobile phase B was ethanol, running time was 20 minutes, gradient was mobile phase A/mobile phase B (50/50), flow rate was 1.0 mL/min, and detection wavelength was UV 210 nm. The first single configuration compound was example 2 (RT=5.8 min, 99% ee) and the second single configuration compound was example 3 (RT=7.7 min, 99% ee).

Examples 4-21

The compounds of examples 4-21 in the following table were prepared according to the synthesis methods of examples 1-3 using the corresponding starting materials.

| Example | Structure | Characterization data |
|---|---|---|
| Example 4 | 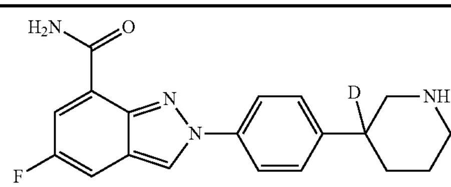 | MS-ESI, m/z: 340.1 [M + 1]$^+$ $^1$H NMR (400 MHz, MeOD) δ 9.0 (s, 1H), 8.15 (dd, J = 15.0, 3.0 Hz, 1H), 7.81-7.72 (m, 3H), 7.25 (d, J = 8.4, 2H), 3.50 (d, J = 12.3 Hz, 2H), 3.25-3.03 (m, 2H), 2.08 (d, J = 10.1 Hz, 2H), 1.97-1.79 (m, 2H). |
| Example 5 | 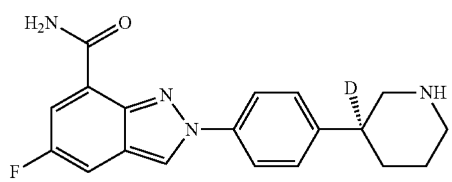 [SMILES: [2H][C@@]1(c2ccc(-n3cc4cc(F)cc(C(N)=O)c4n3)cc2)CCCNC1] | MS-ESI, m/z: 340.1 [M + 1]$^+$ The compound was separated with chiral column Chiralpak AS—H, and chiral resolution conditions were the same as in example 3. RT was 12.2 min. |
| Example 6 | 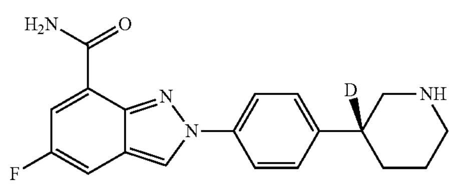 [SMILES: [2H][C@]1(c2ccc(-n3cc4cc(F)cc(C(N)=O)c4n3)cc2)CCCNC1] | MS-ESI, m/z: 340.1 [M + 1]$^+$ The compound was separated with chiral column Chiralpak AS—H, and chiral resolution conditions were the same as in example 2. RT was 10.8 min. |
| Example 7 | 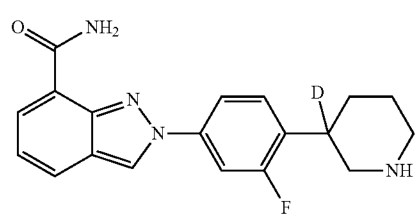 [SMILES: [2H]C1(c2ccc(-n3cc4cccc(C(N)=O)c4n3)cc2F)CCCNC1] | MS-ESI, m/z: 340.1 [M + 1]$^+$ |
| Example 8 | 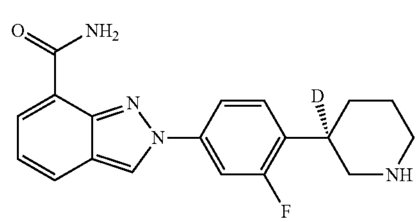 [SMILES: [2H][C@]1(c2ccc(-n3cc4cccc(C(N)=O)c4n3)cc2F)CCCNC1] | MS-ESI, m/z: 340.1 [M + 1]$^+$ |

| Example | Structure | Characterization data |
|---|---|---|
| Example 9 | 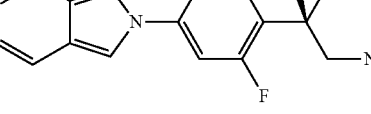 | MS-ESI, m/z: 340.1 [M + 1]+ |
| Example 10 | 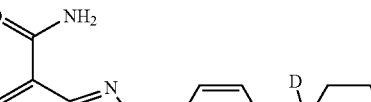 | MS-ESI, m/z: 340.1 [M + 1]+<br>1H NMR (400 MHz, MeOD) δ (ppm) 8.48 (dd, J = 7.0, 0.8 Hz, 1H), 8.15 (t, J = 9.1 Hz, 1H), 7.77 (d, J = 8.2 Hz, 1H), 7.75 (d, J = 8.8 Hz, 2H), 7.30 (d, J = 8.4, 2H), 3.48 (d, J = 12.3 Hz, 2H), 3.15-3.07 (m, 2H), 2.10 (d, J = 10.1 Hz, 2H), 2.01-1.91 (m, 2H). |
| Example 11 | 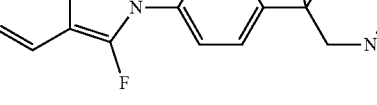 | MS-ESI, m/z: 340.1 [M + 1]+<br>The compound was separated with chiral column Chiralpak AS—H, and chiral resolution conditions were the same as in Example 3. RT was 15.2 min. |
| Example 12 | 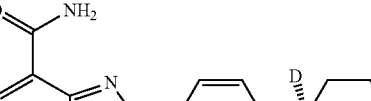 | MS-ESI, m/z: 340.1 [M + 1]+<br>The compound was separated with chiral column Chiralpak AS—H, and chiral resolution conditions were the same as in example 2. RT was 13.4 min. |
| Example 13 | 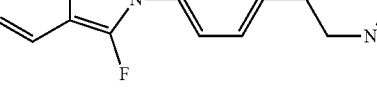 | MS-ESI, m/z: 340.1 [M + 1]+<br>1H NMR (400 MHz, MeOD) δ (ppm) 9.00 (s, 1H), 8.20 (dd, J = 7.0, 0.8 Hz, 1H), 8.05 (t, J = 9.1 Hz, 1H), 7.93 (dd, J = 7.0, 0.8 Hz, 1H), 7.49 (dd, J = 15.0, 3.0 Hz, 1H), 7.37 (dd, J = 16.0, 3.0 Hz, 2H), 3.47 (d, J = 12.3 Hz, 2H), 3.22-3.02 (m, 2H), 2.06 (d, J = 10.1 Hz, 2H), 1.96-1.80 (m, 2H). |
| Example 14 | 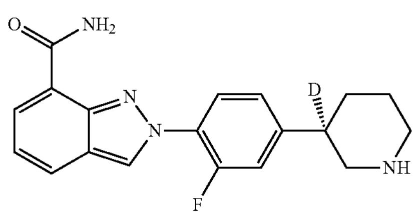 [SMILES: [2H][C@]1(c2ccc(-n3cc4cccc(C(N)=O)c4n3)c(F)c2)CCCNC1] | MS-ESI, m/z: 340.1 [M + 1]+<br>The compound was separated with chiral column Chiralpak AS—H, and chiral resolution conditions were the same as in example 3. RT was 12.3 min. |
| Example 15 | 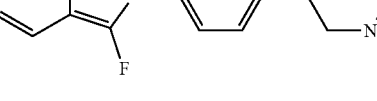 | MS-ESI, m/z: 340.1 [M + 1]+<br>The compound was separated with chiral column Chiralpak AS—H, and chiral resolution conditions were the same as in example 2. RT was 10.9 min. |

-continued

| Example | Structure | Characterization data |
|---|---|---|
| Example 16 | 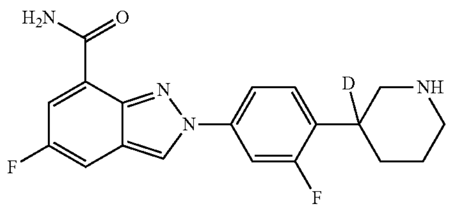 [SMILES: [2H]C1(c2ccc(-n3cc4cc(F)cc(C(N)=O)c4n3)cc2F)CCCNC1] | MS-ESI, m/z: 358.1 [M + 1]⁺ |
| Example 17 | 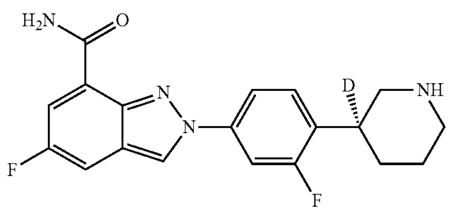 [SMILES: [2H][C@@]1(c2ccc(-n3cc4cc(F)cc(C(N)=O)c4n3)cc2F)CCCNC1] | MS-ESI, m/z: 358.1 [M + 1]⁺ |
| Example 18 | 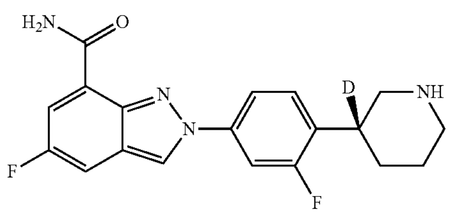 [SMILES: [2H][C@]1(c2ccc(-n3cc4cc(F)cc(C(N)=O)c4n3)cc2F)CCCNC1] | MS-ESI, m/z: 358.1 [M + 1]⁺ |
| Example 19 | 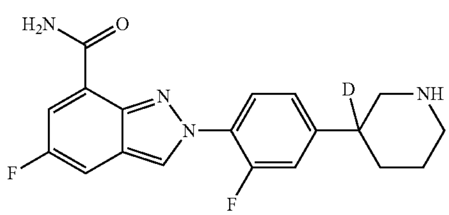 [SMILES: [2H]C1(c2ccc(-n3cc4cc(F)cc(C(N)=O)c4n3)c(F)c2)CCCNC1] | MS-ESI, m/z: 358.1 [M + 1]⁺ |
| Example 20 | 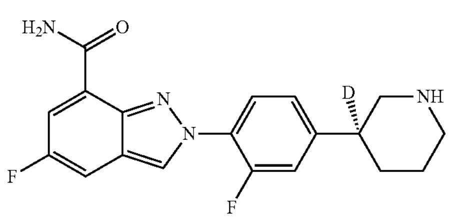 [SMILES: [2H][C@@]1(c2ccc(-n3cc4cc(F)cc(C(N)=O)c4n3)c(F)c2)CCCNC1] | MS-ESI, m/z: 358.1 [M + 1]⁺ |
| Example 21 | 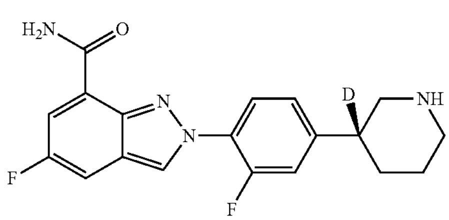 | MS-ESI, m/z: 358.1 [M + 1]⁺ |

Example 22

2-(4-(3-Fluoropiperidin-3-yl) phenyl)-2H-indazole-7-carboxamide

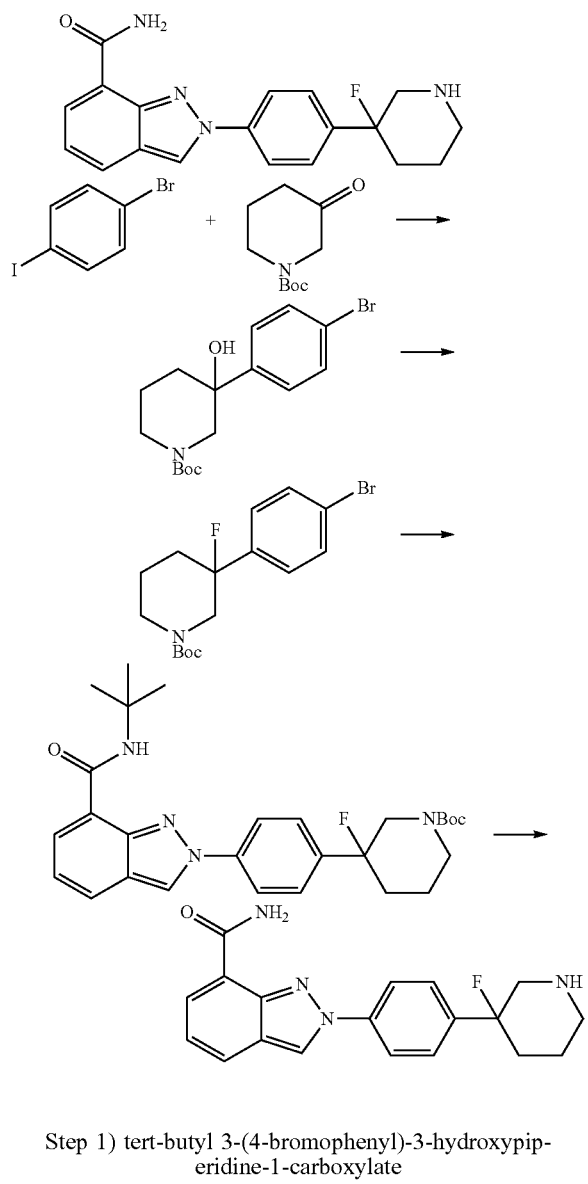

Step 1) tert-butyl 3-(4-bromophenyl)-3-hydroxypiperidine-1-carboxylate

To a solution of 1-bromo-4-iodobenzene (29.0 g, 0.10 mol) in anhydrous tetrahydrofuran (500 mL) was added 2.5 M n-BuLi solution (45 mL) dropwise at −78° C. under nitrogen atmosphere, the temperature was controlled not to exceed −75° C. during the addition, and the mixture was stirred for 15 minutes after the addition. A solution of tert-butyl 3-oxopiperidine-1-carboxylate in tetrahydrofuran (19.5 g, 50 mL THF) was added dropwise into the above mixture, and the temperature was controlled not to exceed −75° C. during the addition and continued to stir for 30 minutes after the addition. TLC showed that the starting material 1-bromo-4-iodobenzene basically disappeared (EA:PE=1:4, UV 254 nm). The reaction system was quenched with 100 mL of ammonium chloride aqueous solution, and extracted with ethyl acetate (300 mL×2). The organic phase was washed with water, concentrated to give 35 g of a crude product, which was purified by column chromatography (eluted from PE to EA:PE=1:4) to give tert-butyl 3-(4-bromophenyl)-3-hydroxypiperidine-1-carboxylate (19.0 g, 51.9% yield).

MS (ESI), m/z, 283.0 [M-72]$^+$.

Step 2) tert-butyl 3-(4-bromophenyl)-3-fluoropiperidine-1-carboxylate

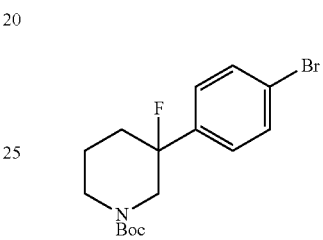

Tert-butyl 3-(4-bromophenyl)-3-hydroxypiperidine-1-carboxylate (26.0 g, 0.074 mol) was dissolved in anhydrous dichloromethane (500 mL) at 20-25° C., and cooled to −78° C. under nitrogen atmosphere, followed by addition of DAST (57.0 g, 0.353 mol), the temperature was controlled not to exceed −75° C. during the addition. After completion of the addition, the mixture was stirred for 2 hours, and LC-MS showed that the starting materials disappeared. The reaction system was quenched with 100 mL of water, and the pH was adjusted to 7-8 with 2 M aq. NaOH. The organic phases were collected, and the aqueous phases were extracted with dichloromethane (300 mL). The combined organic phase was washed with water, concentrated to obtain 21.5 g of crude product, which was purified by column chromatography (eluted from PE to EA:PE=1:10) to give tert-butyl 3-(4-bromophenyl)-3-fluoropiperidine-1-carboxylate (12.5 g, 47.8% yield).

MS (ESI), m/z, 283.0 [M-74]$^+$.

$^1$H NMR (400 MHz, CDCl$_3$) δ (ppm) 7.52 (t, J=10.4 Hz, 2H), 7.32-7.24 (m, 2H), 4.17 (dd, J=23.5, 16.4 Hz, 2H), 3.35-2.69 (m, 2H), 2.27-1.86 (m, 3H), 1.57-1.33 (m, 9H).

Step 3) tert-butyl 3-(4-(7-(tert-butylcarbamoyl)-2H-indazol-2-yl) phenyl)-3-fluoropiperidine-1-carboxylate

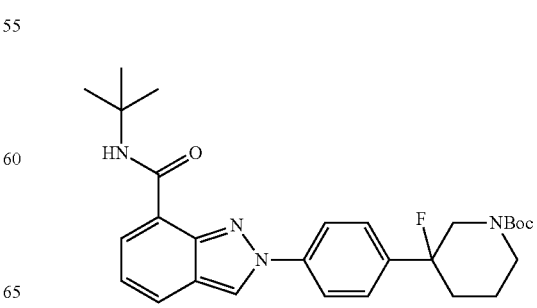

3-(4-Bromophenyl)-3-droperidol-2-one (2.45 g, 6.8 mmol), N-tert-butyl-1H-indazole-7-carboxamide (1.5 g, 6.8 mmol), potassium carbonate (2.95 g, 20.5 mmol), cuprous bromide (0.2 g, 1.5 mmol) and 8-hydroxyquinoline (0.2 g, 1.36 mmol) were mixed in DMAc (60 mL) at 20-25° C., and then the mixture was heated to 110-120° C. and reacted with stirring for 18 hours under nitrogen atmosphere. LCMS showed that part of the starting materials remained. The mixture was cooled to room temperature, quenched with 50 mL of water, and extracted with MTBE (500 mL×2). The combined organic phase was washed with citric acid aqueous solution, dried and concentrated to obtain 3.5 g of crude foamy product, which was purified by column chromatography (eluted from PE to EA:PE=3:2) to give the product tert-butyl 3-(4-(7-(tert-butylcarbamoyl)-2H-indazol-2-yl) phenyl)-3-fluoropiperidine-1-carboxylate (1.56 g).

MS (ESI), m/z, 283.0 [M-43]⁺.

¹H NMR (400 MHz, CDCl₃) δ (ppm) 9.31 (s, 1H), 8.57 (s, 1H), 8.29 (d, J=7.0 Hz, 1H), 7.90 (dd, J=34.5, 8.3 Hz, 3H), 7.64 (d, J=8.5 Hz, 2H), 7.38-7.12 (m, 2H), 4.34 (d, J=58.7 Hz, 2H), 3.46-2.69 (m, 2H), 2.33-1.95 (m, 4H), 1.84-1.37 (m, 21H).

Step 4) 2-(4-(3-fluoropiperidin-3-yl) phenyl)-2H-indazole-7-carboxamide

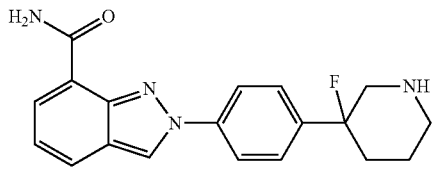 [SMILES: NC(=O)c1cccc2cn(-c3ccc(C4(F)CCCNC4)cc3)nc12]

Tert-butyl 3-(4-(7-(tert-butylcarbamoyl)-2H-indazole-2-yl)phenyl)-3-droperidol-1-carboxylate (0.68 g, 1.4 mmol) was dissolved in toluene (1.5 mL) at 20-25° C., followed by slow addition of methanesulfonic acid (3 mL). After completion of the addition, the reaction mixture was heated to 30-35° C. and reacted with stirring for 30 minutes. The mixture was diluted with water, and pH was neutralized to 8-9 with 2 N NaOH aqueous solution, extracted with ethyl acetate (200 mL×2), dried and concentrated to obtain 600 mg of a crude product 2-(4-(3-fluoropiperidin-3-yl) phenyl)-2H-indazole-7-carboxamide, which was purified with Pre-HPLC to give the trifluoroacetate as the product (370 mg).

Examples 23 & 24

(R or S)-2-(4-(3-fluoropiperidin-3-yl) phenyl)-2H-indazole-7-carboxamide

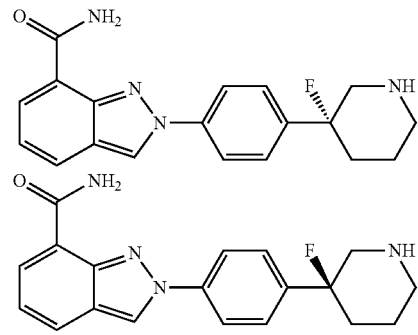

The racemic compound obtained in example 22 was separated by chiral column CHIRALCEL OD-H (10 mm×250 mm, 5 μm) at a column temperature of 40° C. Mobile phase A was 0.1% DEA in hexane (v/v), mobile phase B was ethanol, running time was 35 minutes, gradient mobile was phase A/mobile phase B (60/40, v/v), flow rate was 3.0 mL/min and detection wavelength was UV 210 nm. Two single-configuration compounds were separated and collected at RT of 20.5 minutes (compound of example 23) and 23.8 minutes (compound of example 24), respectively. The compounds were detected by chiral column CHIRALCEL OD-H (4.6 mm×250 mm) at a column temperature of 40° C. Mobile phase A was 0.1% DEA in hexane (v/v), mobile phase B was ethanol, running time was 25 minutes, gradient was mobile phase A/mobile phase B (60/40), flow rate was 0.5 mL/min, and detection wavelength was UV 210 nm. The first single configuration compound was example 23 (RT=15.02 min, 99% ee), and the second single configuration compound was example 24 (RT=16.71 min, 99% ee).

Examples 25-42

The compounds of examples 25-42 in the following table were prepared according to the synthesis methods of examples 22-24 using the corresponding starting materials.

| Example | Structure | Characterization data |
|---|---|---|
| Example 25 | 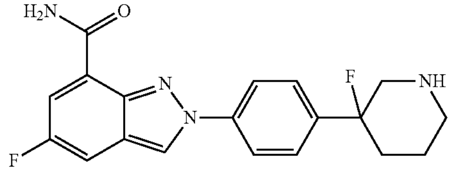 [SMILES: NC(=O)c1cc(F)cc2cn(-c3ccc(C4(F)CCCNC4)cc3)nc12] | MS-ESI, m/z: 357.1 [M + 1]⁺<br>¹H-NMR (400 MHz, MeOD) δ (ppm) 9.05 (s, 1H), 8.21 (dd, J = 15.0, 3.0 Hz, 1H), 7.90-7.71 (m, 3H), 7.27 (dd, J = 8.4, 7.1 Hz, 2H), 3.74-3.40 (m, 3H), 3.23 (td, J = 12.5, 2.6 Hz, 1H), 2.26-1.98 (m, 4H). |
| Example 26 | 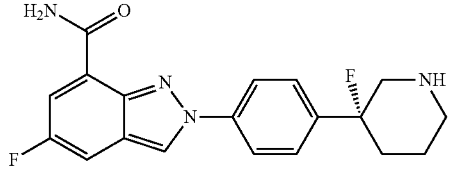 [SMILES: NC(=O)c1cc(F)cc2cn(-c3ccc([C@]4(F)CCCNC4)cc3)nc12] | MS-ESI, m/z: 357.1 [M + 1]⁺<br>The compound was separated with chiral column Chiralpak OD—H, and chiral resolution conditions were the same as in example 23. RT was 22.5 min. |

| Example | Structure | Characterization data |
| --- | --- | --- |
| Example 27 | (5-fluoro-2-(4-(3-fluoropiperidin-3-yl)phenyl)-2H-indazole-7-carboxamide) | MS-ESI, m/z: 357.1 [M + 1]⁺<br>The compound was separated with chiral column Chiralpak OD—H, and chiral resolution conditions were the same as in example 24. RT was 24.5 min. |
| Example 28 | (2-(3-fluoro-4-(3-fluoropiperidin-3-yl)phenyl)-2H-indazole-7-carboxamide) | MS-ESI, m/z: 357.1 [M + 1]⁺ |
| Example 29 | (2-(3-fluoro-4-(3-fluoropiperidin-3-yl)phenyl)-2H-indazole-7-carboxamide, enantiomer) | MS-ESI, m/z: 357.1 [M + 1]⁺ |
| Example 30 | (3-fluoro-2-(4-(3-fluoropiperidin-3-yl)phenyl)-2H-indazole-7-carboxamide) | MS-ESI, m/z: 357.1 [M + 1]⁺ |
| Example 31 | (3-fluoro-2-(4-(3-fluoropiperidin-3-yl)phenyl)-2H-indazole-7-carboxamide) | MS-ESI, m/z: 357.1 [M + 1]⁺<br>$^1$H NMR (400 MHz, MeOD) δ (ppm) 8.45 (dd, J = 7.0, 0.8 Hz, 1H), 8.21 (t, J = 9.1 Hz, 1H), 8.03 (d, J = 8.2 Hz, 1H), 7.78 (d, J = 8.8 Hz, 2H), 7.33 (dd, J = 8.4, 7.1 Hz, 2H), 3.73-3.39 (m, 3H), 3.20 (td, J = 12.5, 2.6 Hz, 1H), 2.25-2.01 (m, 4H). |
| Example 32 | (3-fluoro-2-(4-(3-fluoropiperidin-3-yl)phenyl)-2H-indazole-7-carboxamide) | MS-ESI, m/z: 357.1 [M + 1]⁺<br>The compound was separated with chiral column Chiralpak OD—H, and chiral resolution conditions were the same as in example 23. RT was 24.3 min. |
| Example 33 | (3-fluoro-2-(4-(3-fluoropiperidin-3-yl)phenyl)-2H-indazole-7-carboxamide) | MS-ESI, m/z: 357.1 [M + 1]⁺<br>The compound was separated with chiral column Chiralpak OD—H, and chiral resolution conditions were the same as in example 24. RT was 26.8 min. |

| Example | Structure | Characterization data |
|---|---|---|
| Example 34 | 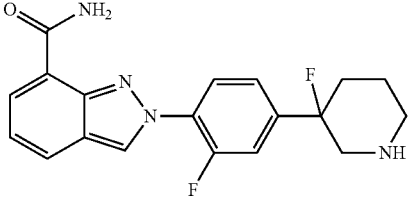 | MS-ESI, m/z: 357.1 [M + 1]⁺<br>$^1$H NMR (400 MHz, MeOD) δ (ppm) 9.03 (s, 1H), 8.15 (dd, J = 7.0, 0.8 Hz, 1H), 8.02 (t, J = 9.1 Hz, 1H), 7.87 (dd, J = 7.0, 0.8 Hz, 1H), 7.51 (dd, J = 15.0, 3.0 Hz, 1H), 7.42 (dd, J = 16.0, 3.0 Hz, 2H), 3.69-3.34 (m, 3H), 3.05 (td, J = 12.5, 2.6 Hz, 1H), 2.19-1.87 (m, 4H). |
| Example 35 | 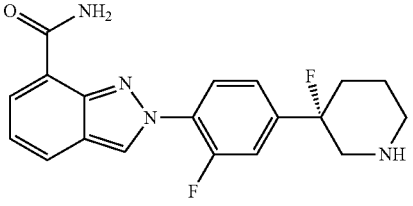 | MS-ESI, m/z: 357.1 [M + 1]⁺<br>The compound was separated with chiral column Chiralpak OD—H, and chiral resolution conditions were the same as in example 23. RT was 21.3 min. |
| Example 36 | 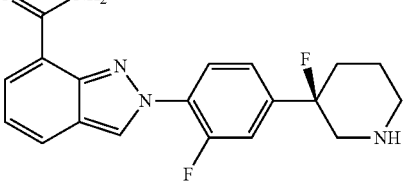 | MS-ESI, m/z: 357.1 [M + 1]⁺<br>The compound was separated with chiral column Chiralpak OD—H, and chiral resolution conditions were the same as in example 24. RT was 23.3 min. |
| Example 37 | 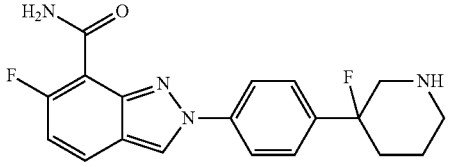 [SMILES: NC(=O)c1c(F)ccc2cn(-c3ccc(C4(F)CCCNC4)cc3)nc12] | MS-ESI, m/z: 357.1 [M + 1]⁺ |
| Example 38 | 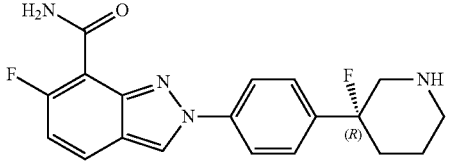 | MS-ESI, m/z: 357.1 [M + 1]⁺ |
| Example 39 | 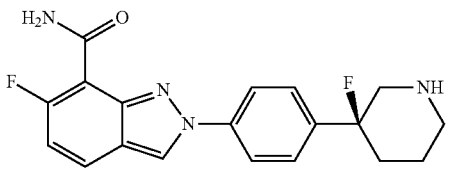 [SMILES: NC(=O)c1c(F)ccc2cn(-c3ccc([C@@]4(F)CCCNC4)cc3)nc12] | MS-ESI, m/z: 357.1 [M + 1]⁺ |
| Example 40 | 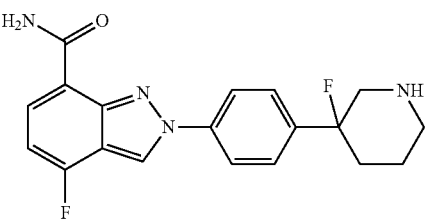 [SMILES: NC(=O)c1ccc(F)c2cn(-c3ccc(C4(F)CCCNC4)cc3)nc12] | MS-ESI, m/z: 357.1 [M + 1]⁺ |

| Example | Structure | Characterization data |
|---|---|---|
| Example 41 | 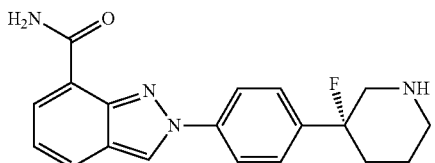 | MS-ESI, m/z: 357.1 [M + 1]⁺ |
| Example 42 | 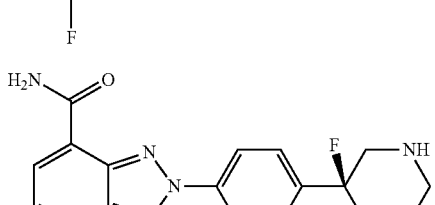 | MS-ESI, m/z: 357.1 [M + 1]⁺ |

Example 43

2-(4-(3-Methylpiperidin-3-yl) phenyl)-2H-indazole-7-carboxamide

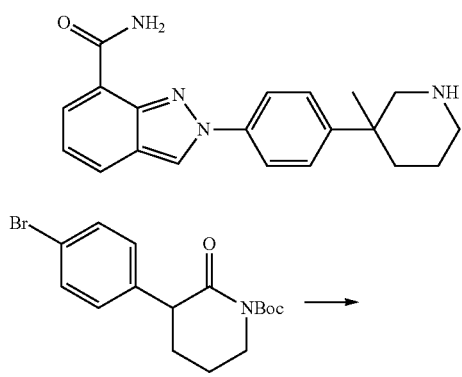

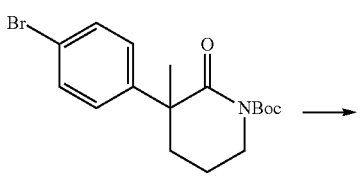

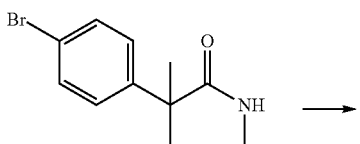

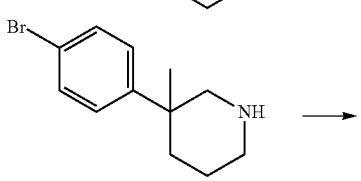

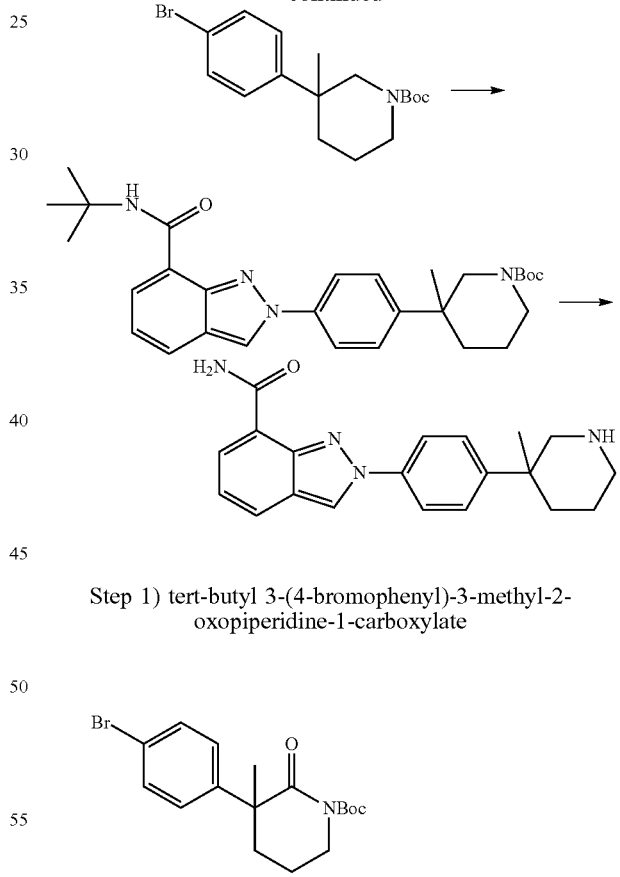

Step 1) tert-butyl 3-(4-bromophenyl)-3-methyl-2-oxopiperidine-1-carboxylate

Tert-butyl 3-(4-bromophenyl)-3-methylpiperidine-1-carboxylate (15.0 g, 42.3 mmol) was dissolved in DMSO (180 mL) at 20-25° C., followed by addition of NaH (60%, 2.2 g, 55.0 mmol). After completion of the addition, the reaction system was heated to 40-45° C. and stirred for 30 minutes. A solution of methyl iodide (6.3 g, 44.4 mmol) in DMSO (20 mL) was added into the above mixture and continued to stir for 30 minutes at 40-45° C. LCMS showed that the raw materials disappeared. The reaction system was quenched with ammonium chloride aqueous solution (150 mL), extracted with ethyl acetate (200 mL×2). The organic phase was washed with water (100 mL×2), dried, and concentrated in vacuo to obtain a crude product 3-(4-bromophenyl)-3-methylpiperidine-2-one (16.0 g, 99% yield).

MS (ESI), m/z, 314.0 [M-55]⁺.

¹H NMR (400 MHz, CDCl₃) δ (ppm) 7.51-7.44 (m, 2H), 7.24-7.18 (m, 2H), 3.71 (ddd, J=12.9, 8.5, 5.7 Hz, 1H), 3.49-3.40 (m, 1H), 2.39 (ddd, J=14.1, 4.8, 4.1 Hz, 1H), 1.96 (ddd, J=14.1, 11.0, 5.1 Hz, 1H), 1.88-1.68 (m, 2H), 1.56 (s, 9H), 1.50 (s, 3H).

Step 2) 3-(4-bromophenyl)-3-methylpiperidin-2-one

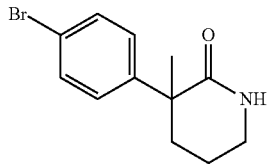

tert-Butyl 3-(4-bromophenyl)-3-methyl-2-oxopiperidine-1-carboxylate (16.0 g, 0.044 mol) was dissolved in ethanol (200 mL) at 20-25° C., followed by slow addition of hydrochloric acid-ethanol solution (200 mL). After completion of the addition, the reaction system was reacted with stirring for 30 minutes, and concentrated to dry. The concentrated residue was basified with aq. NaHCO₃, extracted with ethyl acetate (500 mL×2). The organic phase was dried and concentrated to give the product 3-(4-bromophenyl)-3-methylpiperidine-2-one (11.0 g, 95% yield).

MS (ESI), m/z, 268.0 [M+H]⁺.

Step 3) 3-(4-bromophenyl)-3-methylpiperidine

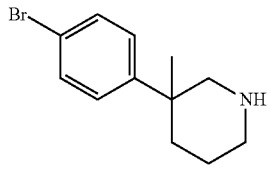

3-(4-Bromophenyl)-3-methylpiperidine-2-one (11.5 g, 43 mmol) was dissolved in tetrahydrofuran (250 mL) at 20-25° C., and cooled to 0-5° C. Then sodium borohydride (4.9 g, 130 mmol) was added in portions and reacted with stirring for 30 minutes, ethanol (6.0 g, 130 mmol) was then added and continued to react with stirring for 30 minutes. Boron trifluoride diethyl ether (19.0 g, 130 mmol) was added dropwise, and after completion of the addition, then the reaction mixture was raised to 20-25° C. and reacted with stirring for 18 hours. 60 mL of concentrated hydrochloric acid was added into the above mixture and stirred for 30 minutes. LCMS showed that the reaction completed. The reaction mixture was quenched with 50 mL of water, the pH was adjusted to 8-9 with 2 M NaOH solution, and extracted with ethyl acetate (500 mL×2). The organic phase was washed with water, dried and concentrated to give a crude 3-(4-bromophenyl)-3-methylpiperidine (10.0 g, 91.7% yield).

MS (ESI), m/z, 254.0 [M+H]⁺.

Step 4) tert-butyl 3-(4-bromophenyl)-3-methylpiperidine-1-carboxylate

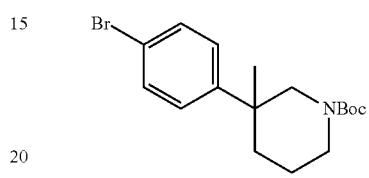

3-(4-Bromophenyl)-3-methylpiperidine (3.0 g, 11.8 mmol) and 1 N NaOH (18 mL) were mixed in MTBE (100 mL) at 20-25° C., followed by addition of (Boc)₂O (2.6 g, 11.9 mmol). After completion of the addition, the reaction solution was stirred for 1 hour, followed by addition of MTBE (100 mL). The organic phases were collected, dried, and concentrated to give a crude tert-butyl 3-(4-bromophenyl)-3-methylpiperidine-1-carboxylate (3.6 g, yield 86.1%).

MS (ESI), m/z, 298.0 [M-55]⁺.

Step 5) tert-butyl 3-(4-(7-(tert-butylcarbamoyl)-2H-indazol-2-yl) phenyl)-3-methylpiperidine-1-carboxylate

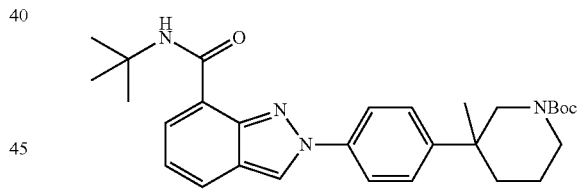

tert-Butyl 3-(4-bromophenyl)-3-methylpiperidine-1-carboxylate (2.56 g, 7.2 mmol), N-tert-butyl-1H-indazole-7-carboxamide (1.56 g, 7.2 mmol), potassium carbonate (3.0 g, 21.7 mmol), cuprous bromide (0.2 g, 1.48 mmol) and 8-hydroxyquinoline (0.2 g, 1.36 mmol) were mixed in DMAc (60 mL) at 20-25° C., and then heated to 110-120° C., and reacted with stirring for 18 hours under nitrogen atmosphere. LCMS showed that some of the starting materials remained and the product was formed. The reaction mixture was cooled to room temperature, quenched with 50 mL of water, and extracted with MTBE (200 mL×2). The organic phase was washed with citric acid aqueous solution, dried and concentrated to give 3.5 g of a crude foamy product. The crude product was purified by column chromatography (eluted from PE to EA/PE=3:2) to give tert-butyl 3-(4-(7-(tert-butylcarbamoyl)-2H-indazol-2-yl) phenyl)-3-methylpiperidine-1-carboxylate (1.8 g, 47% yield).

MS (ESI), m/z, 435.0 [M-100]⁺.

Step 6) 2-(4-(3-methylpiperidin-3-yl) phenyl)-2H-indazole-7-carboxamide

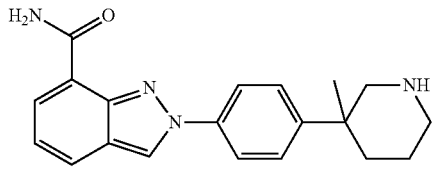 [SMILES: CC1(c2ccc(-n3cc4cccc(C(N)=O)c4n3)cc2)CCCNC1]

tert-Butyl 3-(4-(7-(tert-butylcarbamoyl)-2H-indazol-2-yl) phenyl)-3-methylpiperidine-1-carboxylate (1.0 g, 2 mmol) was mixed with toluene (2 mL) at 20-25° C. Then methanesulfonic acid (4 mL) was slowly added. After completion of the addition, the reaction system was heated to 30-35° C. and reacted with stirring for 30 minutes. LCMS showed that the starting materials disappeared and the product was formed. The reaction mixture was diluted with water, the pH was neutralized 8-9 with aq. NaOH, and extracted with ethyl acetate (100 mL×2), dried and concentrated to give 750 mg of a crude product, which was purified by HPLC to give a trifluoroacetate of 2-(4-(3-methylpiperidin-3-yl) phenyl)-2H-indazole-7-carboxamide as the product (470 mg).

MS (ESI), m/z, 335.2 [M+H]$^+$.

$^1$H-NMR (400 MHz, MeOD) δ (ppm) 8.94 (s, 1H), 8.21-7.96 (m, 4H), 7.69 (d, J=8.8 Hz, 2H), 7.27 (dd, J=8.3, 7.1 Hz, 1H), 3.74 (d, J=13.1 Hz, 1H), 3.53-3.29 (m, 2H), 3.20-3.17 (m, 1H), 2.41 (t, J=13.0 Hz, 1H), 1.94 (d, J=12.1 Hz, 3H), 1.42 (s, 3H).

Examples 44 & 45

(R or S)-2-(4-(3-methylpiperidin-3-yl) phenyl)-2H-indazole-7-carboxamide

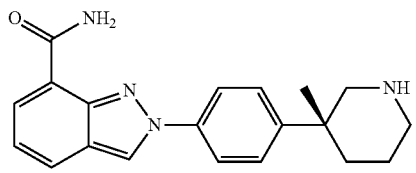

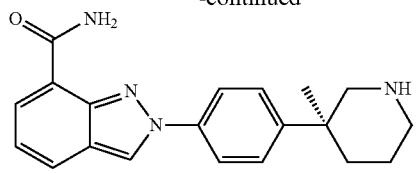

The above-described racemic compound was separated by a chiral column to obtain an R-configuration product (example 44) and an S-configuration product (example 45) in a single configuration.

The racemic compound obtained in example 43 was separated by chiral column Chrialpak AS-H (10 mm×250 mm, 5 μm) at a column temperature of 40° C. Mobile phase A was 0.1% DEA in hexane (v/v), mobile phase B was ethanol, running time was 30 minutes, gradient mobile was phase A/mobile phase B (50/50, v/v), flow rate was 6.0 mL/min and detection wavelength was UV 210 nm. Two single-configuration compounds were separated and collected at RT of 13.6 minutes (compound of example 44) and 15.8 minutes (compound of example 45), respectively. The compounds were detected by chiral column Chrialpak AS-H (4.6 mm×250 mm) at a column temperature of 40° C. Mobile phase A was 0.1% DEA in hexane (v/v), mobile phase B was ethanol, running time was 20 minutes, gradient was mobile phase A/mobile phase B (50/50), flow rate was 1.0 mL/min, and detection wavelength was UV 210 nm. The first single configuration compound was example 44 (RT=8.9 min, 99% ee), and the second single configuration compound was example 45 (RT=11.3 min, 99% ee).

Examples 46-63

The compounds of examples 46-63 in the following table were prepared according to the synthesis methods of examples 43-45 using the corresponding starting materials.

| Example | Structure | Characterization data |
|---|---|---|
| Example 46 | 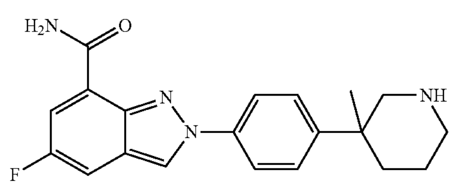 [SMILES: CC1(c2ccc(-n3cc4cc(F)cc(C(N)=O)c4n3)cc2)CCCNC1] | MS-ESI, m/z: 353.1 [M + 1]$^+$ <br> $^1$H-NMR (400 MHz, MeOD) δ (ppm) 9.02 (s, 1H), 8.19 (dd, J = 15.0, 3.0 Hz, 1H), 7.85-7.71 (m, 3H), 7.30 (dd, J = 8.3, 7.1 Hz, 2H), 3.76 (d, J = 13.1 Hz, 1H), 3.56-3.34-3.23 (m, 2H), 3.20-3.17 (m, 1 H), 2.43 (t, J = 13.0 Hz, 1H), 1.94 (d, J = 12.1 Hz, 3H), 1.41 (s, 3H). |
| Example 47 | 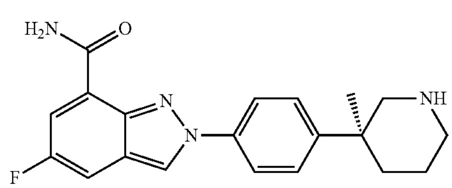 [SMILES: C[C@@]1(c2ccc(-n3cc4cc(F)cc(C(N)=O)c4n3)cc2)CCCNC1] | MS-ESI, m/z: 353.1 [M + 1]$^+$ <br> The compound was separated with chiral column Chiralpak AS—H, and chiral resolution conditions were the same as in example 45. RT was 16.7 min. |

-continued

| Example | Structure | Characterization data |
|---|---|---|
| Example 48 | (5-fluoro-2-(4-(3-methylpiperidin-3-yl)phenyl)-2H-indazole-7-carboxamide) | MS-ESI, m/z: 353.1 [M + 1]⁺<br>The compound was separated with chiral column Chiralpak AS—H, and chiral resolution conditions were the same as in example 44. RT was 14.2 min. |
| Example 49 | (2-(3-fluoro-4-(3-methylpiperidin-3-yl)phenyl)-2H-indazole-7-carboxamide) | MS-ESI, m/z: 353.1 [M + 1]⁺ |
| Example 50 | (2-(3-fluoro-4-((S)-3-methylpiperidin-3-yl)phenyl)-2H-indazole-7-carboxamide) | MS-ESI, m/z: 353.1 [M + 1]⁺ |
| Example 51 | (2-(3-fluoro-4-((R)-3-methylpiperidin-3-yl)phenyl)-2H-indazole-7-carboxamide) | MS-ESI, m/z: 353.1 [M + 1]⁺ |
| Example 52 | (3-fluoro-2-(4-(3-methylpiperidin-3-yl)phenyl)-2H-indazole-7-carboxamide) | MS-ESI, m/z: 353.1 [M + 1]⁺<br>¹H-NMR (400 MHz, MeOD) δ (ppm) 8.39 (dd, J = 7.0, 0.8 Hz, 1H), 8.12 (t, J = 9.1 Hz, 1H), 7.82-7.72 (m, 3H), 7.29 (dd, J = 8.3, 7.1 Hz, 1H), 3.72 (d, J = 13.1 Hz, 1H), 3.56-3.33 (m, 2H), 3.25-3.19 (m, 1H), 2.40 (t, J = 13.0 Hz, 1H), 1.93 (d, J = 12.1 Hz, 3H), 1.39 (s, 3H). |
| Example 53 | (3-fluoro-2-(4-((S)-3-methylpiperidin-3-yl)phenyl)-2H-indazole-7-carboxamide) | MS-ESI, m/z: 353.1 [M + 1]⁺<br>The compound was separated with chiral column Chiralpak AS—H, and chiral resolution conditions were the same as in example 45. RT was 18.7 min. |
| Example 54 | (3-fluoro-2-(4-((R)-3-methylpiperidin-3-yl)phenyl)-2H-indazole-7-carboxamide) | MS-ESI, m/z: 353.1 [M + 1]⁺<br>The compound was separated with chiral column Chiralpak AS—H, and chiral resolution conditions were the same as in example 44. RT was 16.9 min. |

| Example | Structure | Characterization data |
|---|---|---|
| Example 55 | 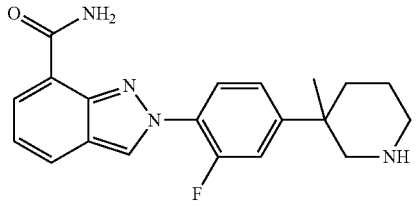 [SMILES: CC1(c2ccc(-n3cc4cccc(C(N)=O)c4n3)c(F)c2)CCCNC1] | MS-ESI, m/z: 353.1 [M + 1]$^+$ |
| Example 56 | 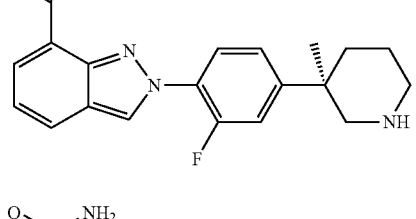 | MS-ESI, m/z: 353.1 [M + 1]$^+$ |
| Example 57 | 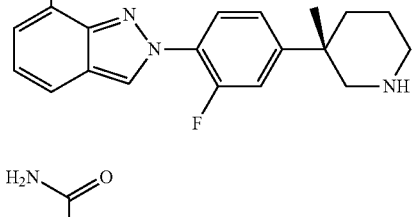 | MS-ESI, m/z: 353.1 [M + 1]$^+$ |
| Example 58 | 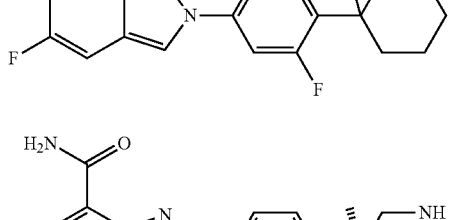 | MS-ESI, m/z: 358.1 [M + 1]$^+$<br>$^1$H-NMR (400 MHz, MeOD) δ (ppm) 9.02 (s, 1H), 8.19 (dd, J = 15.0, 3.0 Hz, 1H), 7.98-7.79 (m, 2H), 7.52-7.61 (m, 2H), 3.68 (d, J = 13.1 Hz, 1H), 3.48-3.25 (m, 2H), 3.18-3.11 (m, 1H), 2.39 (t, J = 13.0 Hz, 1H), 1.99 (d, J = 12.1 Hz, 3H), 1.45 (s, 3H). |
| Example 59 | 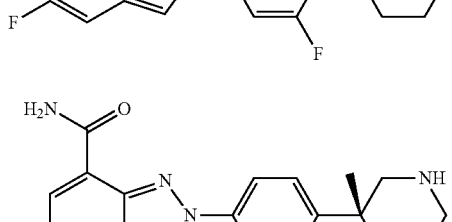 | MS-ESI, m/z: 358.1 [M + 1]$^+$<br>The compound was separated with chiral column Chiralpak AS—H, and chiral resolution conditions were the same as in example 45. RT was 15.8 min. |
| Example 60 | 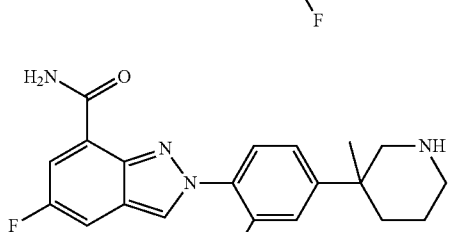 | MS-ESI, m/z: 358.1 [M + 1]$^+$<br>The compound was separated with chiral column Chiralpak AS—H, and chiral resolution conditions were the same as in example 44. RT was 14.2 min. |
| Example 61 | 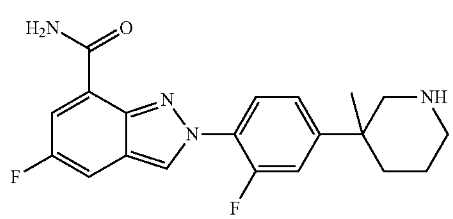 | MS-ESI, m/z: 358.1 [M + 1]$^+$ |

| Example | Structure | Characterization data |
|---|---|---|
| Example 62 | (structure) | MS-ESI, m/z: 358.1 [M + 1]⁺ |
| Example 63 | (structure) | MS-ESI, m/z: 358.1 [M + 1]⁺ |

Biological Test Examples

Biological Example 1: Determination of PARP Kinase Activity

PARP1 kinase activity was tested by the following method:
Materials and instruments used in this experiment:
Multi-Function Microplate Reader: SpectraMax M5 Microplate Reader (Molecular Devices)
PARP1 Colorimetric Assay Kit (BPS, Cat #80580)
PBS (Life Technologies, Cat #003000)
Tween-20 (Sigma, Cat # P9416-100 mL)
$H_2SO_4$ (Sinopharm Chemical Reagent, Cat #10021618)
Experimental method and steps
1. PARP1 Colorimetric Assay
1.1 PARP1 Colorimetric Assay Kit Includes:
PARP1 5 µg
5× histone mixture 1 mL
10× assay mixture containing biotinylated substrate 300 µL
10×PARP assay buffer 1 mL
Blocking buffer 25 mL
Activated DNA 500 µL
Streptavidin-HRP 100 µL
Colorimetric HRP substrate 10 mL
One 96-well plate
1.2 Reagents Preparation:
1×PBS: a pack of PBS powder was took and 1 L deionized water was added to dissolve it completely;
PBST: Tween-20 was added into 1×PBS;
2 M $H_2SO_4$: $H_2SO_4$ was diluted to 2 M with deionized water;
1×PARP assay buffer: 10×PARP assay buffer was diluted with deionized water at a ratio of 1:10 to obtain a 1×PARP assay buffer.
1.3 Compound Dilution
The compound was dissolved in DMSO and diluted to 100 µM for use.
When testing, the 100 µM compound stock solution was diluted to 10 µM with 1×PARP buffer, and then the compound was successively diluted with 1×PARP buffer containing 10% DMSO to obtain a series of concentrations of the compounds for use. 5 µL of diluted compound (total volume 50 µL) was added to each well, that the final concentration of the compound was a series of 3-fold concentrations diluted from 1 µM.
1.4 Reaction Steps
1.4.1 Coating
1) 5× histone mixture was diluted with 1×PBS in a ratio of 1:5 to obtain a 1× coating solution.
2) 50 µL of diluted coating solution was added to each well for overnight at 4° C.
3) The coating solution was discarded, and each well was washed 3 times with 200 µL of PBST buffer.
4) 200 µL of blocking buffer was added to each well and incubated at room temperature for 90 minutes.
5) The blocking buffer was discarded and washed with PBST for 3 times.
1.4.2 PARP1 Reaction Experiment
1) A reaction solution was prepared in a ratio of 2.5 µL of 2.5 µL 10×PARP buffer+2.5 µL 10×PARP Assay mixture+5 µL Activated DNA+15 µL deionized water per well, and 25 µL of the reaction solution was added to each well (see Table 1).
2) 5 µL of diluted compound was added to the sample test well and an equal volume of 1× PARP buffer containing 10% DMSO was added to the control well and blank well.

TABLE 1

|  | Control well | Test well | Blank well |
|---|---|---|---|
| 10x PARP buffer | 2.5 µL | 2.5 µL | 2.5 µL |
| 10x Assay mixture | 2.5 µL | 2.5 µL | 2.5 µL |
| Activated DNA | 5 µL | 5 µL | 5 µL |
| Deionized water | 15 µL | 15 µL | 15 µL |
| Diluted compound to be tested | — | 5 µL | — |
| 1x PARP buffer containing 10% DMSO | 5 µL | — | 5 µL |
| 1x PARP buffer | — | — | 20 µL |
| PARP1 (2.5 ng/µL) | 20 µL | 20 µL | — |
| Total volume | 50 µL | 50 µL | 50 µL |

3) 20 µL of 1×PARP buffer was added to the blank well.
4) PARP1 was thawed on ice and diluted with 1×PARP buffer to 2.5 ng/µL, and 20 µL of diluted PARP1 was added to all reaction wells except blank wells, mixed well, and reacted for 1 hour at room temperature.

5) The reaction solution was discarded and washed 3 times with PBST.

1.4.3 Testing

1) Streptavidin-HRP was diluted with Blocking buffer in a ratio of 1:50, followed by addition of 50 μL of diluted Streptavidin-HRP to all wells and incubated for 30 minutes at room temperature.

3) HRP was discarded and washed 3 times with PBST.

4) 100 μL of colorimetric HRP substrate was added to each well and reacted at room temperature for 20 minutes.

5) 100 μL of 2 M $H_2SO_4$ was added to each well and OD 450 nm was read on a microplate reader.

2. Calculation of the inhibition rate and $IC_{50}$

The inhibition rate was calculated by the following formula:

Inhibition rate=(ODsample−OD0%)/(OD100%−OD0%)×100%

ODsample: the OD value of the sample test well;
OD0%: the OD value of the blank well;
OD100%: OD value of the control well.

The PARP-1 kinase inhibitory activities of the compound of the present disclosure were determined by the above experimental method, and the vitro enzymatic inhibitory activity ($IC_{50}$) results of the compound were shown in Table 2 below: "+" represents 10-100 "++" represents 1-10 μm, "+++" represents 0.5-1 μm, "++++" represents 0.1-0.5 μm, "+++++" represents less than 0.1 μm.

TABLE 2

Inhibition of PARP-1 kinase by the compound of the disclosure

| Example | PARP1 | Example | PARP1 | Example | PARP1 |
|---|---|---|---|---|---|
| 1 | +++++ | 21 | +++++ | 41 | ++++ |
| 2 | +++++ | 22 | +++++ | 42 | ++++ |
| 3 | +++++ | 23 | +++++ | 43 | ++++ |
| 4 | +++++ | 24 | +++++ | 44 | ++++ |
| 5 | +++++ | 25 | +++++ | 45 | ++++ |
| 6 | +++++ | 26 | +++++ | 46 | ++++ |
| 7 | +++++ | 27 | +++++ | 47 | ++++ |
| 8 | +++++ | 28 | +++++ | 48 | ++++ |
| 9 | +++++ | 29 | +++++ | 49 | ++++ |
| 10 | ++++ | 30 | +++++ | 50 | ++++ |
| 11 | ++++ | 31 | ++++ | 51 | ++++ |
| 12 | ++++ | 32 | ++++ | 52 | +++ |
| 13 | ++++ | 33 | ++++ | 53 | +++ |
| 14 | ++++ | 34 | ++++ | 54 | +++ |
| 15 | ++++ | 35 | ++++ | 55 | ++++ |
| 16 | +++++ | 36 | ++++ | 56 | ++++ |
| 17 | +++++ | 37 | ++++ | 57 | ++++ |
| 18 | +++++ | 38 | ++++ | 58 | ++++ |
| 19 | +++++ | 39 | ++++ | 59 | ++++ |
| 20 | +++++ | 40 | ++++ | 60 | ++++ |
| 61 | ++++ | 62 | ++++ | niraparib | +++++ |

Biological Example 2: Pharmacokinetic Study of Compounds of Examples 2, 23 and 24 in Rats 1. Summary of Experiment SD rats were used as test animals, and the drug concentrations in plasma at different times after intravenous and intragastric administration of the compounds of examples were determined by LC/MS/MS method(s) to study the pharmacokinetics of the compound in the present disclosure in rats 2. Experimental Scheme 2.1 Compounds for Tested:

Compounds of Examples 3, 23, and 24 of the present disclosure and Niraparib as the positive control.

2.2 Experimental Animal

Healthy adult male SD (Sprague-Dawley) rats, 3 animals per test compound, 6-9 weeks old, weighing 250±50 g, were purchased from Shanghai SLAC Laboratory Animal Co., Ltd.

2.3 Sample Preparation

The appropriate amount of sample was weighed out, 0.5% Methocel/2% tween 80 was added to the final volume, and 2 mg/mL was prepared for intragastric administration.

2.4 Drug Administration

Each 3 male SD rats of each test compound were taken by intragastric administration at a dosage of 10 mg/kg after fasting overnight.

3. Experimental Operation

Blood samples of each animal were collected at different time points 0.083-24 h from jugular vein puncture after administration, K2-EDTA anticoagulation, centrifugation, and blood plasma were collected, frozen at −70° C. until LC/MS/MS analysis.

4. Pharmacokinetic Results

The rat pharmacokinetic parameters of the compound of the disclosure were shown in Table 3 below.

TABLE 3

Pharmacokinetic parameters of compound of the present disclosure in rats

| | Dose PO (10 mg/kg) | | | | | | |
|---|---|---|---|---|---|---|---|
| Example | $C_{max}$ (ng/mL) | AUC (ng/mL*h) | $T_{1/2}$ (h) | MRT (h) | CL (mL/min/kg) | Vdss (L/kg) | F (%) |
| Example 3 | 549 | 5164 | 3.18 | 7.95 | 24.9 | 6.04 | 62.3 |
| Example 23 | 359 | 3055 | 16.0 | 7.12 | 25.2 | 5.79 | 49.7 |
| Example 24 | 935 | 5021 | 2.64 | 4.63 | 20.3 | 2.68 | 61.3 |
| niraparib | 509 | 4540 | 3.4 | 8.59 | 28.7 | 8.18 | 65.0 |

The results showed that the exposure amounts (AUC) of compounds of example 3 and example 24 were significantly higher than the positive compound (Niraparib), and $T_{1/2}$ of compound of example 23 was significantly higher than Niraparib.

Biological Example 3: Evaluation of Metabolic Stability In Vitro of Compound of Example 23 of the Present Disclosure Evaluation of in vitro liver microsomal stability of the compound of the present disclosure was tested by the following method:

Preparation of test compound stock solution: a certain amount of sample compound powder was accurately weighed, dissolved and diluted to 10 mM with DMSO, respectively.

Buffer: 100 mM potassium phosphate buffer, pH 7.4; 10 nM $MgCl_2$.

NADPH: β-nicotinamide adenine dinucleotide phosphate reduced form, tetrasodium salt, NADPH.4Na, supplier: sigma, catalog number 616.

Liver microsomes: human liver microsomes, Corning Cat No. 452117; Rat liver microsomes, Xenotech Cat No. R1000; Mouse liver microsomes, Xenotech Cat No. M1000; Dog liver microsomes, Xenotech Cat No. D1000; Liver microsomes of cynomolgus monkey, Corning Cat No. 452413, the final concentration was 0.5 mg protein/mL.

Preparation of stop solution: a cold acetonitrile solution containing 100 ng/mL Tolbutamide and 100 ng/mL Labetalol as an internal standard.

Compound Dilution:

1. Intermediate solution: 5 μL of compound or control in stock solution (10 mM) was diluted with 495 μL of methanol (concentration: 100 μM, 99% MeOH).

2. Operating solution: the intermediate solution was diluted to 50 μL with 450 μL 100 mM potassium phosphate buffer (concentration: 10 μM, 9.9% MeOH).

Experimental Steps:

1. 10 μL of compound or control solution per well was added to all plates (T0, T5, T10, T20, T30, T60, NCF60) except matrix blank.

2. Microsome solution was distributed to 96-well plates according to platemap for standby, 680 μL per well, and the mixture of microsome solution and the compound was incubated at 37° C. for about 10 minutes.

3. 100 mM potassium phosphate buffer was added to NCF60, 10 μL per well, and incubated at 37° C., followed by starting the timer.

4. After preheating, NADPH regeneration system was distributed to 96-well plate, 90 μL per well, for standby according to plate map, which was added to each plate to start the reaction, 10 μL per well. The final concentration of each component in the incubation medium includes: 0.5 mg protein/mL microsome, 1 μM test compound, 1 μM ginseng, 0.99% methanol and 0.01% DMSO.

5. Incubated at 37° C., followed by starting the timer.

6. The above-prepared stop solution (4° C. cooling) was added to stop the reaction, 300 μL per well.

7. The sampling plate was shaken for about 10 minutes.

8. The sample was centrifuged at 4,000 rpm for 20 minutes at 4° C.

9. During centrifugation, eight new 96-well plates were loaded with 300 μL of HPLC water, and then 100 μL of supernatant was transferred for mixing, followed by LC/MS/MS detection.

10. Data analysis: The peak area of the corresponding compound and internal standard was detected by LC-MS/MS, and the $T_{1/2}$ of the compound was calculated by the following formula:

$$C_t = C_0 \cdot e^{-k_e \cdot t}$$
$$T_{1/2} = \frac{Ln2}{k_e} = \frac{0.693}{k_e}.$$

Example 23 and Niraparib were analyzed according to the above steps, and the results were shown in Table 4 below.

TABLE 4

Results of metabolic stability in liver microsome in vitro of the compound of example

| Example | Rat $T_{1/2}$ (min) | Mouse $T_{1/2}$ (min) | Dog $T_{1/2}$ (min) | Cynomolgus monkey $T_{1/2}$ (min) | Human $T_{1/2}$ (min) |
|---|---|---|---|---|---|
| Example 23 | 64.2 | 61.3 | 20.3 | 62 | >145 |
| Niraparib | 105.6 | 110.1 | 22.6 | 58 | >145 |

11. Experimental results: As shown in Table 4, compound 23 showed excellent metabolic stability in human liver microsomes, dog liver microsomes, and cynomolgus monkey liver microsomes.

Biological Example 4: Pharmacodynamic Study of Compound of Example 23 of the Present Disclosure on Mouse MDA-MB-436 Model 4.1 Experimental Animals BALB/c nude mice, aged 6-8 weeks old, weighing 18-22 g, female, provided by Shanghai Lab Animal Research Center (Shanghai Xipuer-Beikai) with the animal certificate no: 20130016001914.

4.2 Feeding Conditions

The experiment was started after 3-7 days after the animal arrived. Animals were housed in IVC (independent air supply system) cages (four animals per cage) in SPF grade experimental animal facilities. Each cage animal information card contained the number of animals in the cage, sex, strain, receiving date, dosing schedule, experiment number, group, and start date of the experiment. All cages, bedding and drinking water were sterilized before use and were updated twice a week.

4.3 Tumor Cells Inoculation Method

Human breast cancer MDA-MB-436 cells (ATCC, Manacas, Va., Article number (Art. No.): ATCC-HTB-130) were cultured in vitro in monolayer under the conditions of RPMI1640 medium with 10% fetal bovine serum and 37° C. 5% $CO_2$ incubator. The passage was routinely digested with trypsin-EDTA twice a week. When the cell saturation was up to 80%-90% and reached the requirement, the cells were collected, counted and inoculated. 0.2 mL ($1\times10^7$) MDA-MB-436 cells (added with matrix gel, volume ratio 1:1) were subcutaneously inoculated into the right back of each mouse, and mice were randomly grouped and dosed when the average tumor volume reached 157 $mm^3$.

4.4 Sample Preparation 2.5 g of methylcellulose was slowly added into 80 mL of deionized water in a suitable container under stirring, stirred until uniform, 10 mL of Tween 80 was added to the solution, stirred until uniform, continued to add deionized water to 500 mL, and stirred until uniform to obtain a vehicle solution. Then an appropriate amount of p-toluenesulfonate of example 23 was weighed, and an appropriate amount of the above vehicle solution was added and vortexed until uniform.

4.5 Drug Administration.

Dosage and schedule were showed in Table 5. The subcutaneous tumor volumes of nude mice were measured 2-3 times a week, and the mice were weighed, and the data were recorded.

TABLE 5

| Number | Group | Dose (mg/kg) | Route | Number of animals | Drug delivery cycle |
|---|---|---|---|---|---|
| 1 | Vehicle | — | PO | 6 | PO x 18 days |
| 2 | example 23 | 50 | PO | 6 | PO x 18 days |
| 3 | Niraparib | 50 | PO | 6 | PO x 18 days |

Note:
Dosing volume was 10 mg/mL.

4.6 Analysis and Evaluation

Experimental evaluation index: tumor growth inhibition rate TGI (%) or relative tumor proliferation rate T/C (%) was used for evaluation, wherein T was the experimental group, and C was the control group.

Calculation of relative tumor proliferation rate: If $T>T_0$, T/C (%)=$(T-T_0)/(C-C_0)\times100\%$, if $T<T_0$, T/C (%)=$(T-T_0)/$ $T_0 \times 100\%$, wherein T and C were tumor volumes at the end of the experiment; $T_0$ and $C_0$ were tumor volumes at the beginning of the experiment.

Calculation of tumor growth inhibition rate TGI (%): TGI (%)=(1−T/C)×100%.

Evaluation criteria: T/C (%)>40 (i.e. TGI (%)<60%) means invalid; T/C (%)≤40 (i.e. TGI (%)≥60%) means valid and statistical significance value P<0.05 was effective.

4.7 Results of Pharmacodynamics Experiment

The inhibitory effects of the vehicle, example 23 and Niraparib on tumor volume of MDA-MB-436 cells were shown in FIG. 1 and Table 6.

TABLE 6

Inhibitory effects of compound of example 23 of the present disclosure and Niraparib on tumor volume of MDA-MB-436 cells

| Group | Route | Tumor volume (mm³) (day 0) | Tumor volume (mm³) (day 39) | T/C (%) | TGI (%) | P value |
|---|---|---|---|---|---|---|
| Vehicle | PO | 157 | 2126 | — | — | — |
| Example 23 | PO | 157 | 49 | −68 | 168 | 0.006 |
| Niraparib | PO | 157 | 187 | 1.5 | 98.5 | 0.005 |

The results showed that the compound of example 23 of the present disclosure and Niraparib had a very strong inhibitory effect on the tumor growth in a nude mouse model of the MDA-MB-436 cells at a dose of 50 mg/kg and continuous PO administration for 18 days. Moreover, the anti-tumor activity of compound of example 23 of the present disclosure was stronger than that of the positive control Niraparib. The administration was stopped on the $18^{th}$ day and continued to observe until the $39^{th}$ day, and it was found that compound of example 23 and Niraparib could continue to inhibit the tumor growth. Furthermore, the compound of example 23 of the present disclosure has a significantly stronger tumor inhibition effect than positive control Niraparib in the observation period. In addition, the compound of example 23 of the present disclosure was able to cause complete regression of tumors in some animals, and the rate of test animals in which the tumor completely disappeared was 50% in compound of example 23, while the rate of positive control Niraparib was zero.

Biological Example 5: Evaluation of Inhibitory Effect of Compound of Example 23 of the Present Disclosure on Human Liver Microsomal CYP450 Enzymes The inhibitory effects of the compound of the present disclosure on the CYP450 enzymes of six human subtypes were determined by the following experimental method:

Reference compounds of each subtype: CYP1A2: α-naphthoflavone; CYP2C9: sulfaphenazole; CYP2C19: omeprazole; CYP3A4: ketoconazole; CYP2D6: quinidine.

Substrate concentration: CYP1A2: Phenacetin at 30 µM; CYP2C9: Diclofenac at 10 µM; CYP2C19: S-Mephenytoin at 35 µM; CYP3A4: Midazolam at 5 µM and Testosterone at 80 µM; CYP2D6: Bufuralol at 10 µM.

Experimental Steps:

1. 0.1 M potassium phosphate buffer (K-buffer), pH 7.4, was preheated;

100 mM K-buffer: 9.5 mL of Stock A and 40.5 mL of Stock B were mixed evenly, diluted to 500 mL with Milli-Q ultrapure water, and then the pH of the buffer was adjusted to 7.4 with KOH or $H_3PO_4$.

Stock A (1 M potassium dihydrogen phosphate): 136.5 g of potassium dihydrogen phosphate was dissolved in 1 L Milli-Q ultrapure water;

Stock B (1 M dipotassium hydrogen phosphate): 174.2 g of dipotassium hydrogen phosphate was dissolved in 1 L of Milli-Q ultrapure water.

2. A concentration gradient of the test compound and the reference inhibitor (400×) was prepared in a 96-well plate;

2.1. 8 µL of 10 mM test compound was added into 12 µL of acetonitrile and mixed evenly.

2.2. The standard solution of inhibitors for CYP1A2, CYP2C9, and CYP2D6 was prepared: 12 µL of 1 mM α-naphthoflavone+10 µL of 40 mM sulfamethoxazole+10 µL of 10 mM quinidine+8 µL of DMSO.

2.3. A separate inhibitor standard for CYP3A4 and CYP2C19 was prepared: 8 µL of DMSO+12 µL of CAN.

2.4. A 3-fold gradient dilution was performed in a mixture of DMSO/ACN (v/v: 40:60).

3. 4×NADPH coenzyme (66.7 mg of ANDPH was dissolved in 10 mL of 0.1 MK-buffer, pH=7.4) was prepared.

4. 4× substrate concentration (2 mL for each subtype) was prepared and operated on ice when adding HLM.

5. 0.2 mg/mL of HLM solution (10 µL 20 mg/mL to 990 µL 0.1 M K-buffer) was prepared on ice.

6. 0.2 mg/mL of HLM was added to the test wells, 400 µL per well, and then the gradient diluted 400× test compound was added to the corresponding wells.

7. 0.2 mg/mL of HLM was added to the test wells, 200 µL per well, and then the gradient-diluted reference inhibitor was added to the corresponding wells. Steps 6 and 7 needed to be performed on ice.

8. The 96-well test plate was placed on ice and the following solution (multiple well) was added to the test plate:

8.1. 30 µL of test compound and reference compound were mixed in 0.2 mg/mL of HLM solution (see steps 6 and 7).

8.2. 15 µL of 4× substrate solution (see step 4) was added.

9. The 96-well test plate and NADPH solution were pre-incubated for 5 minutes at 37° C.

10. Preheated 8 mM of NADPH solution was added to the 96-well test plate (see step 3) to initiate the reaction, 15 µL per well.

11. The test plate was incubated at 37° C.: 3A4 for 5 minutes, each of 1A2, 2C9 and 2D6 for 10 minutes, and 2C19 for 45 minutes.

12. ACN containing internal reference was added to stop the reaction, 120 µL per well.

13. After quenching, the plate was shaked with an oscillator (IKA, MTS 2/4) for 10 minutes (600 rpm) and then centrifuged for 15 minutes (Thermo Multifuge×3R).

14. 50 µL of supernatant from each well was transferred to a 96-well sample plate containing 50 µL of ultrapure water (Millipore, ZMQS50F01) for LC/MS analysis.

Data Analysis: Curve fitting was performed using the following formula to calculate the $IC_{50}$ based on data calculation using the GraphPad Prism 5.0 or Xlfit model 205:

$$Y = \text{Bottom} + \frac{\text{Top} - \text{Bottom}}{1 + 10^{(\log EC50 - X) * HillSlope}}$$

X was the logarithm of the concentration. Y was the concentration of the inhibitor in response to high to low.

The $IC_{50}$ of the compound of the present disclosure against various subtypes of human liver microsomal CYP450 enzymes was shown in Table 7 below.

TABLE 7

| | $IC_{50}$ (μM) | | | | | |
|---|---|---|---|---|---|---|
| Example | 1A2 | 2C9 | 2C19 | 2D6 | 3A4 (Midazolam) | 3A4 (Testosterone) |
| Example 23 | >10 | >10 | >10 | >10 | >10 | >10 |
| Niraparib | >10 | >10 | >10 | >10 | >10 | >10 |
| Reference | 0.003 | 0.443 | 3.586 | 0.033 | 0.015 | 0.037 |

The results showed that the inhibition half-life of compound of example 23 of the present disclosure on the six major subtypes of CYP450 was greater than 10 μM, indicating that the compound has good safety in CYP450 enzymes metabolism.

Biological Example 6: Determination of hERG Potassium Ion Channel Inhibitory Activity of Compound of Example 23 of the Present Invention The inhibitory effect of the compound of the present disclosure on the CYP450 enzymes of six human subtypes was determined by the following experimental method:

6.1 Cells Preparation

CHO-hERG cells were cultured in a 175 cm² flask, and when the cell density was increased to 60-80%, the medium was removed and washed with 7 mL of PBS (Phosphate Buffered Saline phosphate buffer), and then digested with 3 mL of Detachin.

After the digestion was completed, 7 mL of the culture solution was added to neutralize and then centrifuged, the supernatant was removed, and 5 mL of the culture solution was resuspended to ensure a cell density of $2\text{-}5\times10^6$/mL.

6.2 Solution Preparation (as Shown in Table 8)

TABLE 8

| Composition of intracellular fluid and external fluid | | |
|---|---|---|
| Reagent | Extracellular fluid (mM) | Intracellular fluid (mM) |
| $CaCl_2$ | 2 | 5.374 |
| $MgCl_2$ | 1 | 1.75 |
| KCl | 4 | 120 |
| NaCl | 145 | — |
| Glucose | 10 | — |
| HEPES | 10 | 10 |
| EGTA | — | 5 |
| $Na_2ATP$ | — | 4 |
| pH | 7.40 (adjusted with NaOH), Osmolarity-305 mOsm | 7.25 (adjusted with KOH), Osmolarity-290 mOsm |

6.3 Electrophysiological Recording Process

The single-cell high impedance sealing and the whole-cell mode formation process were all automatically completed by the Qpatch instrument. After obtaining the whole-cell recording mode, the cells were clamped at −80 mV (millivolt). Before giving a 5-second+40 mV depolarization stimulus, a 50 ms-50 mV pre-voltage was first given, repolarized to −50 mV for 5 seconds, and then returned to −80 mV. This voltage stimulation was applied every 15 seconds. After recording for 2 minutes, extracellular fluid was given for 5 minutes, and then the administration process was started. The compound concentration started from the lowest test concentration, and each test concentration was given for 2.5 minutes. After all concentrations were continuously given, the positive control compound of 3 μM Cisapride was given. At least 3 cells were tested at each concentration (n≥3).

6.4 Preparation of Compound

The 20 mM compound mother solution was diluted with extracellular fluid, and 5 μL of 20 mM compound mother solution was added to 2495 μL of extracellular solution, diluted 500-fold to 40 μM, and then sequentially performed 3-fold continuous dilution in an extracellular fluid containing 0.2% DMSO to obtain the final concentration to be tested. The highest test concentration was 40 μM, which in turn was 6 concentrations of 40, 13.33, 4.44, 1.48, 0.49 and 0.16 μM respectively. The final concentration of DMSO did not exceed 0.2%, which has no effect on the hERG potassium channel.

6.5 Data analysis

The experimental data were analyzed by XLFit software.

6.6 Quality Control

Environment: humidity 20-50%, temperature 22-25° C.;

Reagents: The experimental reagents were purchased from Sigma Company with the purity of >98%;

The experimental data in the report must meet the following standards:

Whole-cell sealing impedance >100 MΩ

Tail current amplitude >400 pA

Pharmacological parameters: The inhibitory effects of Cisapride with multiple concentrations on the hERG channel were set as the positive control.

6.7 Experimental Results

The results of inhibition of hERG by compound of example 23 of the present disclosure were shown in Table 9 below.

TABLE 9

| Example | Maximal inhibitory rate (%) | $IC_{50}$ (μM) |
|---|---|---|
| Example 23 | 29.75 | >40 |
| Niraparib | 50.40 | 39.56 |
| Cisapride | 87.41 | 0.057 |

The results showed that the inhibitory half-life of compound of example 23 of the present disclosure on the hERG potassium ion channel was more than 40 μM, indicating that there was no inhibitory effect.

Although specific embodiments of the present disclosure have been described and illustrated herein, those skilled in the art should understand that these embodiments are merely examples and can be varied or modified without departing from the principles and essence of the present disclosure. Therefore, the scope of the present disclosure is limited only by the appended claims.

What is claimed is:

1. A compound as shown in general formula I, a pharmaceutically acceptable salt thereof, an isomer thereof or a mixture form of the isomers, a solvate thereof, a polymorph thereof, a stable isotope derivative thereof or a prodrug thereof;

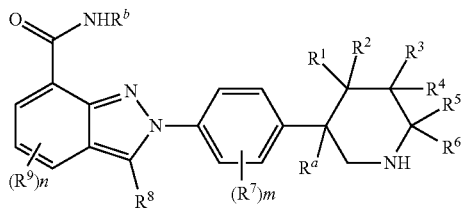

wherein,
- $R^a$ is selected from fluorine, substituted or unsubstituted $C_{1-6}$ alkyl or substituted or unsubstituted cycloalkyl;
- $R^b$ is selected from hydrogen, deuterium, substituted or unsubstituted $C_{1-6}$ alkyl or substituted or unsubstituted cycloalkyl;
- $R^1$, $R^2$, $R^3$, $R^4$, $R^5$, $R^6$, $R^7$, $R^8$ and $R^9$ are each independently selected from hydrogen, deuterium or fluorine
- m is the number of $R^7$ and is 0, 1, 2, 3, or 4; and
- n is the number of $R^9$ and is 0, 1, 2, or 3.

2. The compound as shown in general formula I, the pharmaceutically acceptable salt thereof, the isomer thereof or the mixture form of the isomers, the solvate thereof, the polymorph thereof, the stable isotope derivative thereof or the prodrug thereof as defined in claim 1, wherein, $R^b$ is hydrogen or deuterium.

3. The compound as shown in general formula I, the pharmaceutically acceptable salt thereof, the isomer thereof or the mixture form of the isomers, the solvate thereof, the polymorph thereof, the stable isotope derivative thereof or the prodrug thereof as defined in claim 1, wherein, the compound as shown in general formula I is a compound as shown in formula I-1 as follows,

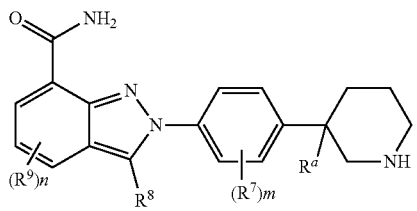

wherein $R^a$ is selected from fluorine or substituted or unsubstituted $C_{1-6}$ alkyl; $R^7$, $R^8$, $R^9$, m and n are as defined in claim 1.

4. The compound as shown in general formula I, the pharmaceutically acceptable salt thereof, the isomer thereof or the mixture form of the isomers, the solvate thereof, the polymorph thereof, the stable isotope derivative thereof or the prodrug thereof as defined in claim 1, wherein, the compound as shown in general formula I is a compound as shown in formula I-3 as follows:

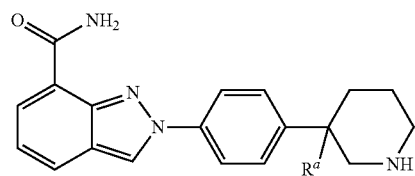

wherein, $R^a$ is selected from fluorine or substituted or unsubstituted $C_{1-6}$ alkyl.

5. The compound as shown in general formula I, the pharmaceutically acceptable salt thereof, the isomer thereof or the mixture form of the isomers, the solvate thereof, the polymorph thereof, the stable isotope derivative thereof or the prodrug thereof as defined in claim 1, wherein, the compound as shown in general formula I is a compound as shown in formula I-4 as follows:

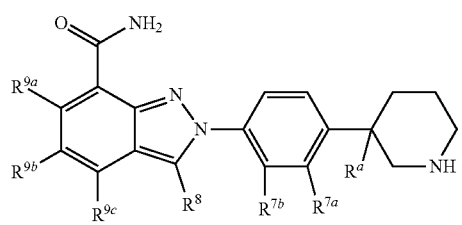

wherein $R^a$ is methyl, or fluorine; and
$R^{7a}$, $R^{7b}$, $R^8$, $R^{9a}$, $R^{9b}$, and $R^{9c}$ are each independently hydrogen or fluorine.

6. The compound as shown in general formula I, the pharmaceutically acceptable salt thereof, the isomer thereof or the mixture form of the isomers, the solvate thereof, the polymorph thereof, the stable isotope derivative thereof or the prodrug thereof as defined in claim 5, wherein, the $R^a$ is fluorine;
and/or, the $R^{7b}$ is hydrogen;
and/or, the $R^8$ is hydrogen;
and/or, the $R^{9a}$ is hydrogen;
and/or, the $R^{9c}$ is hydrogen.

7. The compound as shown in general formula I, the pharmaceutically acceptable salt thereof, the isomer thereof or the mixture form of the isomers, the solvate thereof, the polymorph thereof, the stable isotope derivative thereof or the prodrug thereof as defined in claim 1, wherein, the compound as shown in general formula I is selected from any of the following compounds:

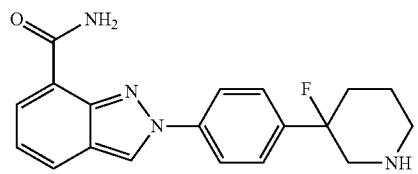

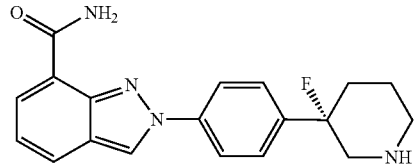

-continued
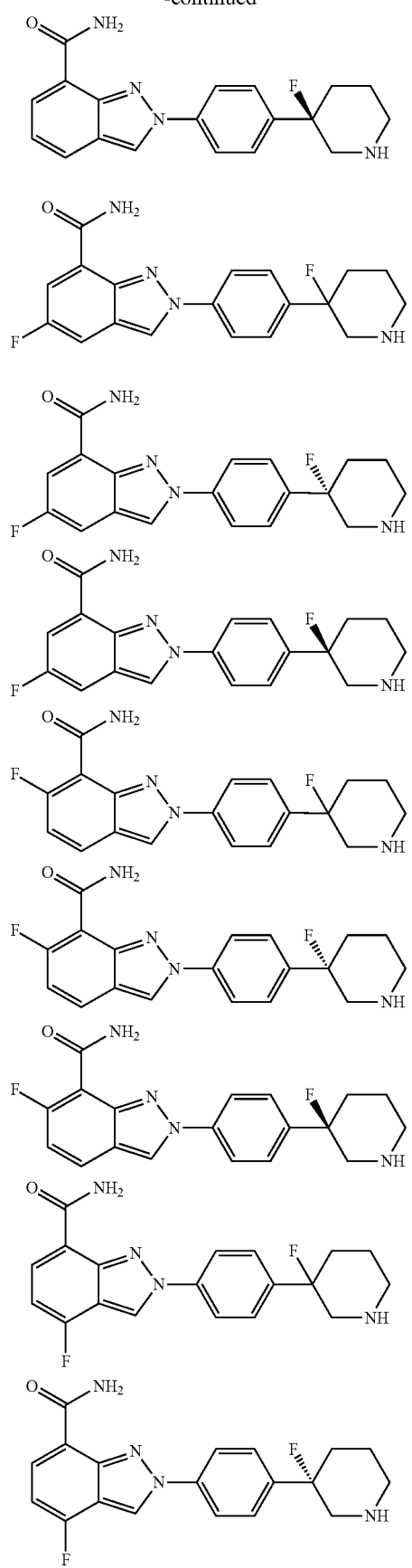
-continued
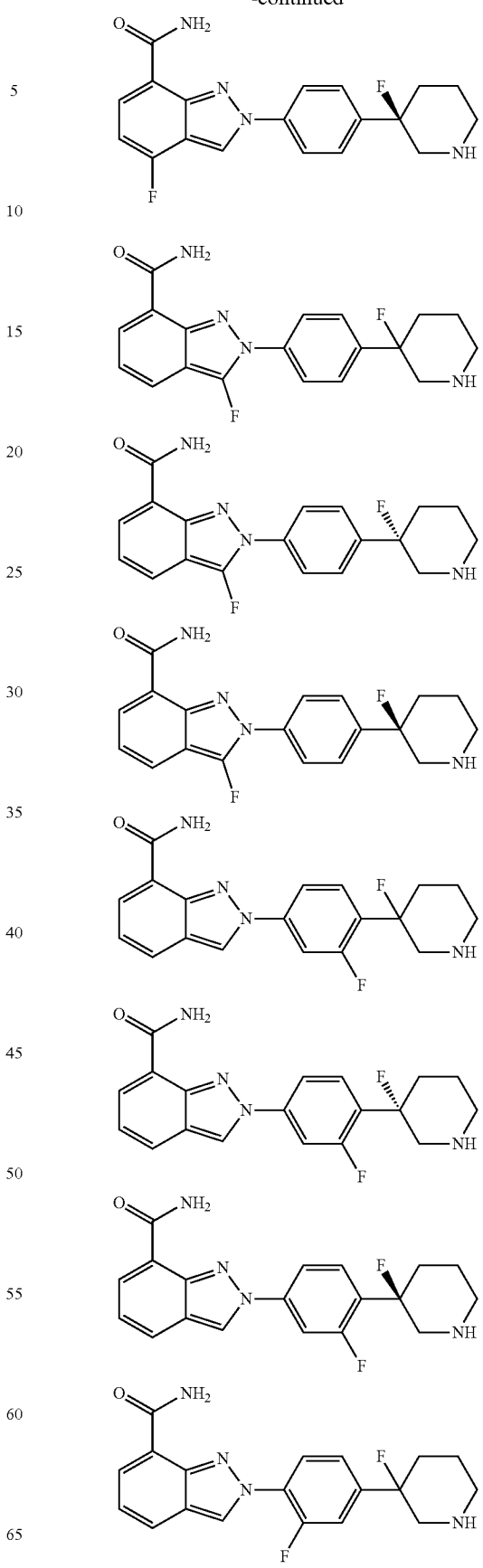

-continued
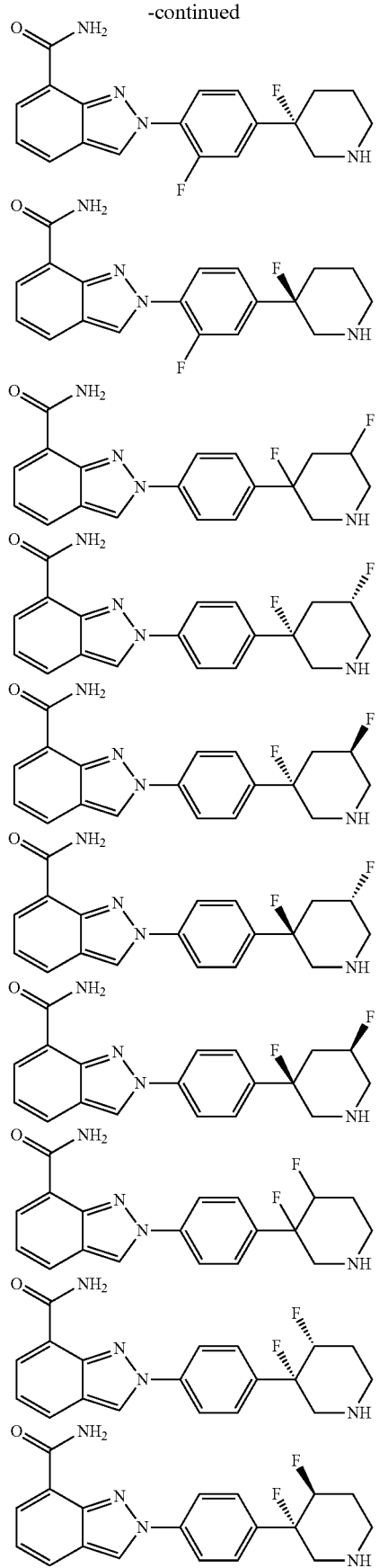
-continued
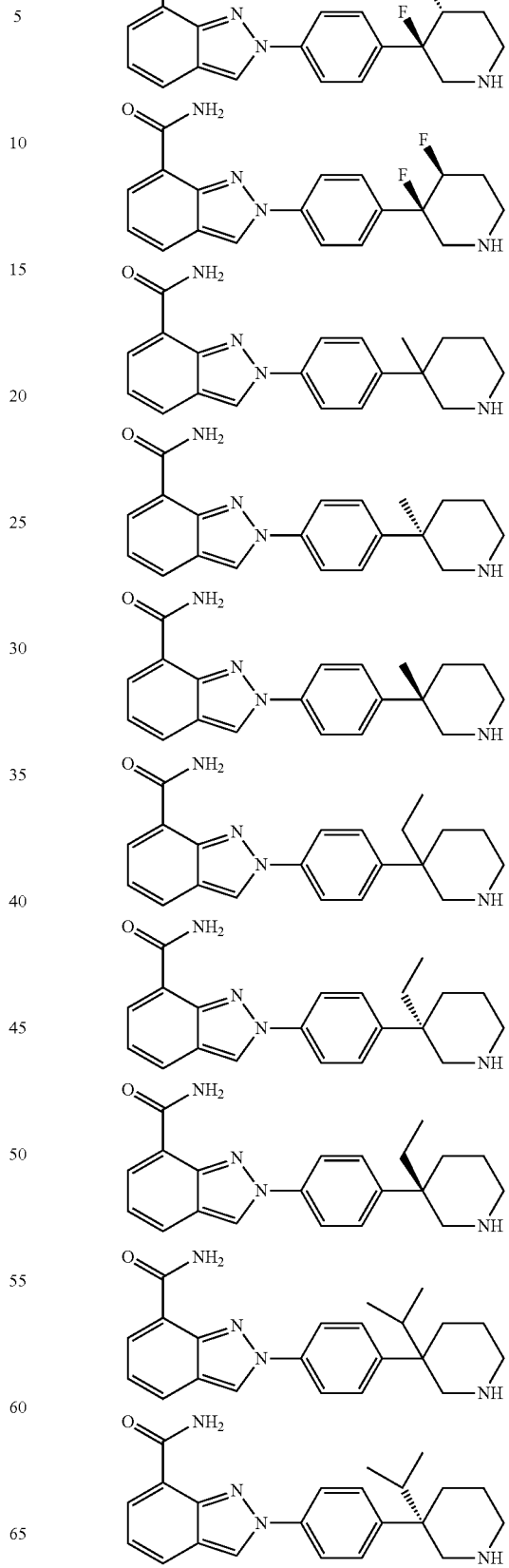

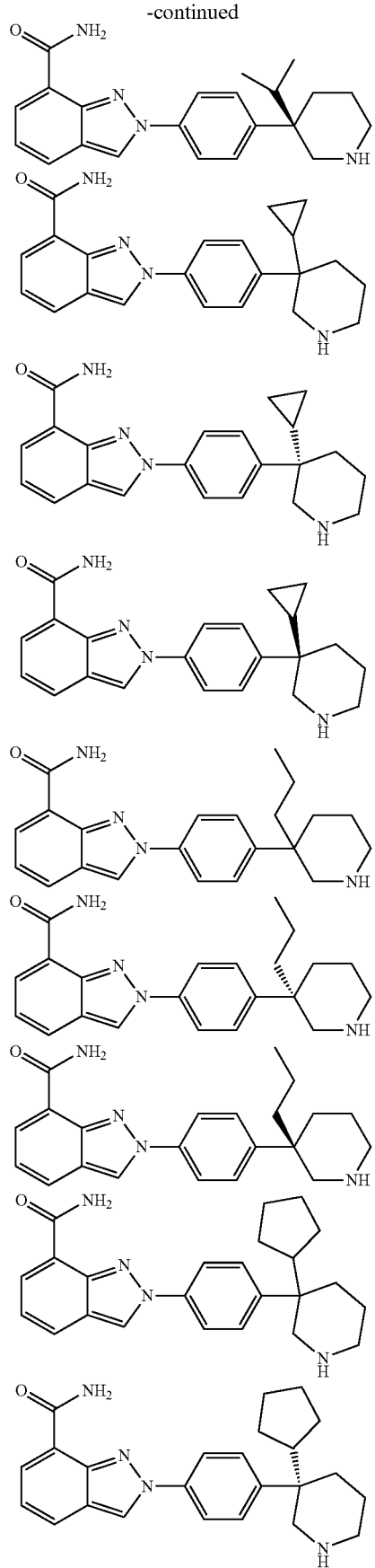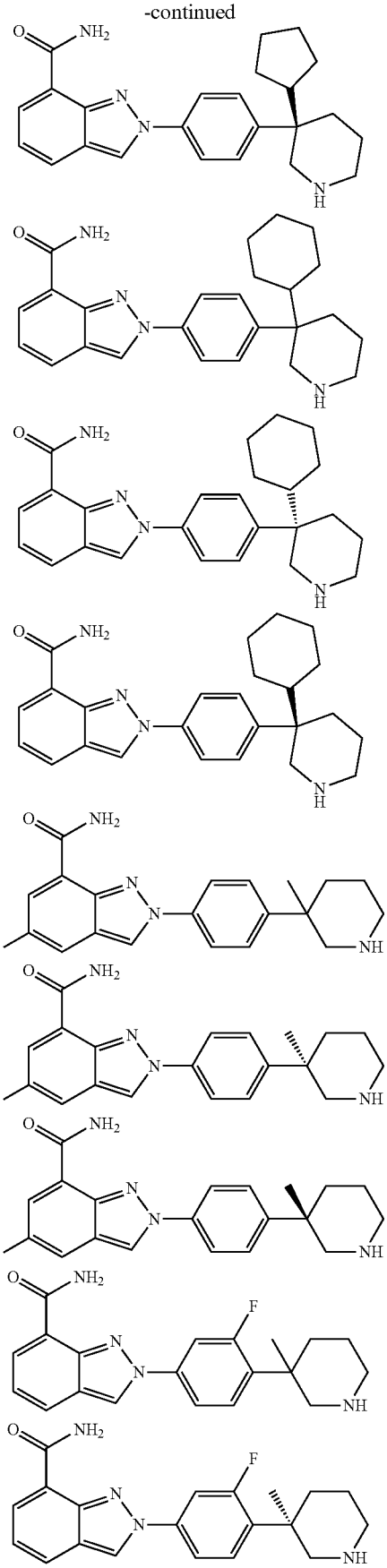

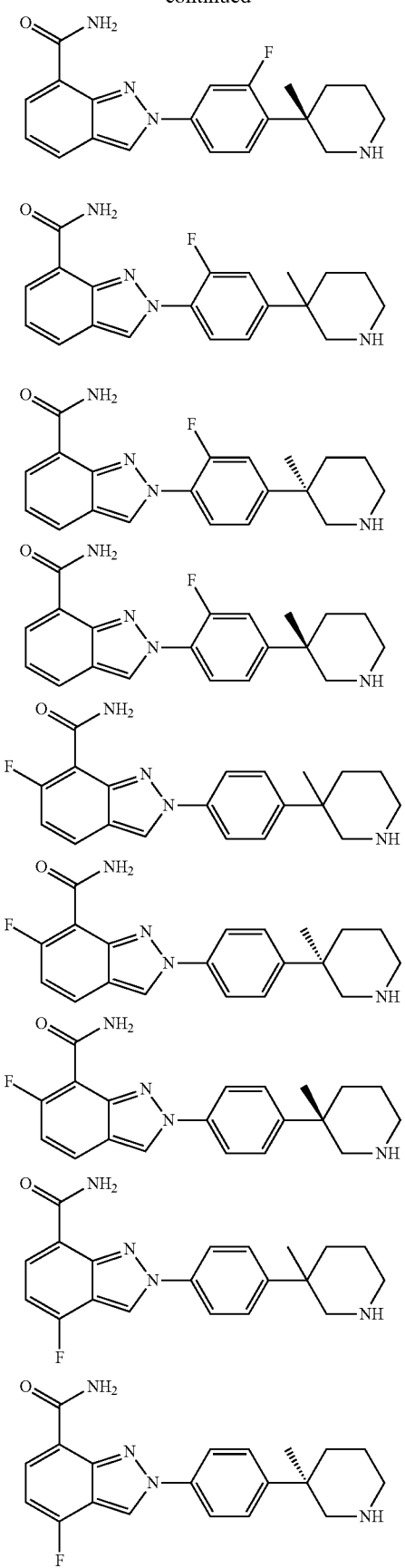
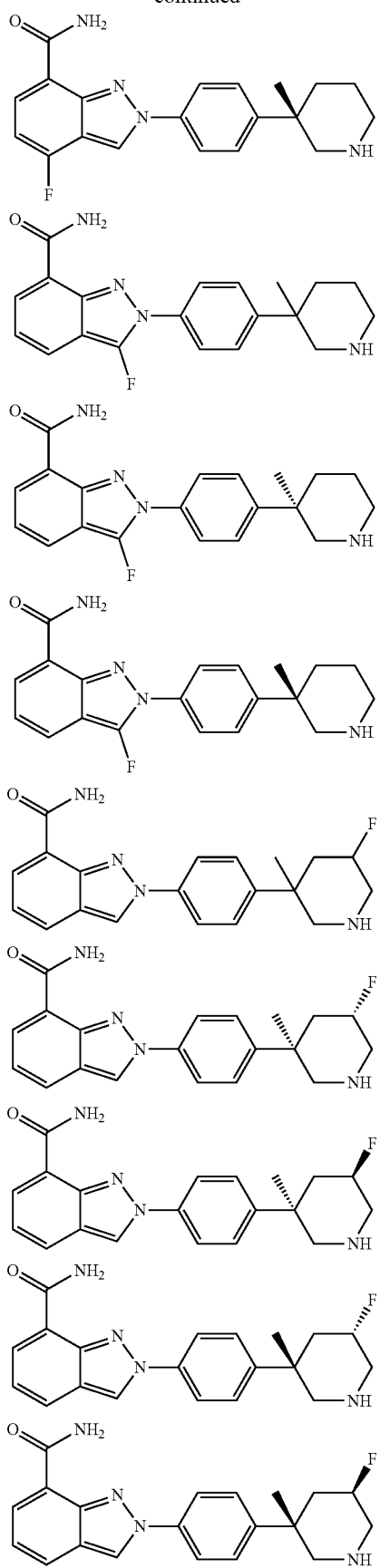

-continued

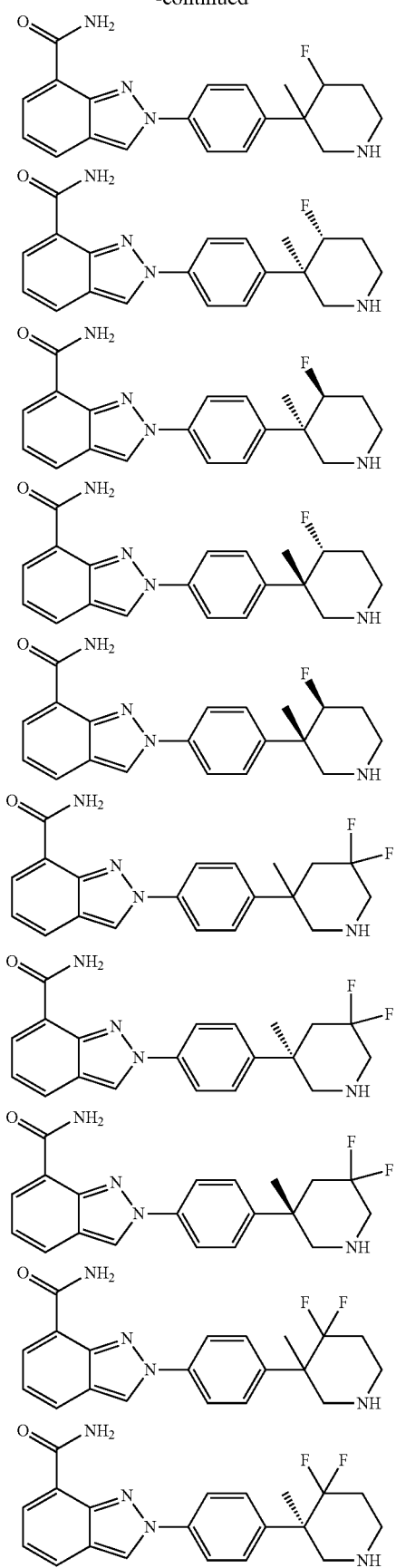

-continued

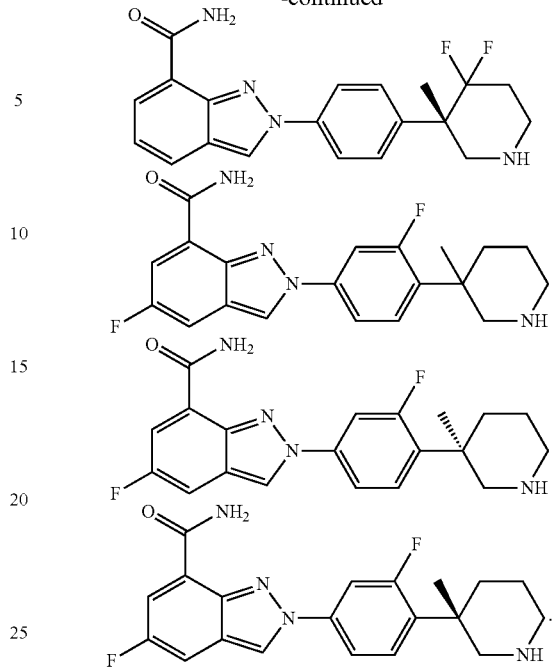

8. The compound as shown in general formula I, the pharmaceutically acceptable salt thereof, the isomer thereof or the mixture form of the isomers, the solvate thereof, the polymorph thereof, the stable isotope derivative thereof or the prodrug thereof as defined in claim 1, wherein, the compound as shown in general formula I is obtained from compound 105 by respectively collecting at RT of 20.5 minutes or 23.8 minutes under chiral resolution condition 2;

Compound 105

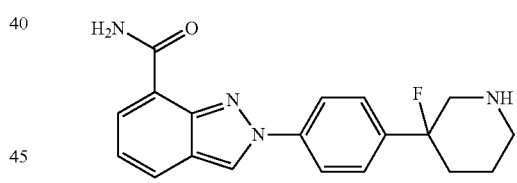

the compound as shown in general formula I is obtained from compound 106 by respectively collecting at RT of 22.5 minutes or 24.5 minutes under the chiral resolution condition 2;

Compound 106

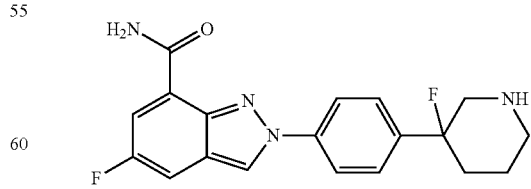

or, the compound as shown in general formula I is obtained from compound 107 by respectively collecting at RT of 24.3 minutes or 26.8 minutes under the chiral resolution condition 2;

Compound 107

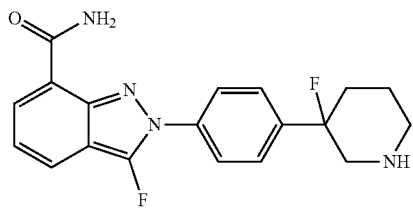

or, the compound as shown in general formula I is obtained from compound 108 by respectively collecting at RT of 21.3 minutes or 23.3 minutes under the chiral resolution condition 2;

Compound 108

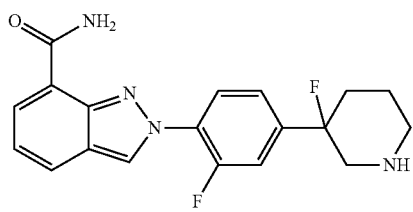

or, the compound as shown in general formula I is obtained from compound 109 by respectively collecting at RT of 13.6 minutes or 15.8 minutes under the chiral resolution condition 1;

Compound 109

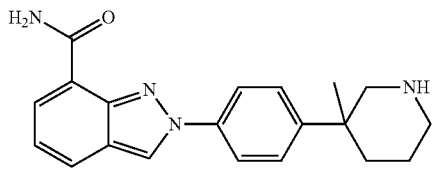

or, the compound as shown in general formula I is obtained from compound 110 by respectively collecting at RT of 16.7 minutes or 14.2 minutes under the chiral resolution condition 1;

Compound 110

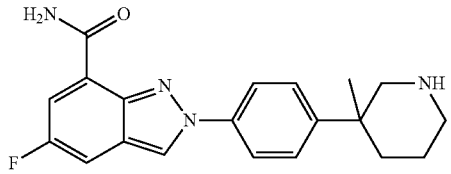

or, the compound as shown in general formula I is obtained from compound 111 by respectively collecting at RT of 18.7 minutes or 16.9 minutes under the chiral resolution condition 1;

Compound 111

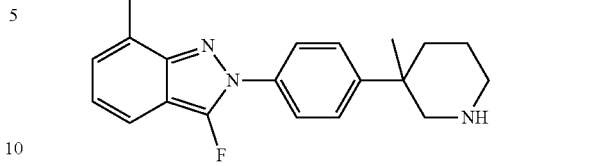

or, the compound as shown in general formula I is obtained from compound 112 by respectively collecting at RT of 15.8 minutes or 14.2 minutes under the chiral resolution condition 1;

Compound 112

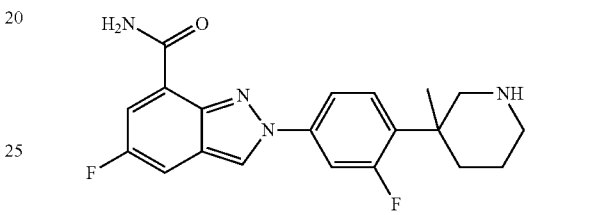

the chiral resolution condition 1 includes:
chiral column is Chrialpak AS-H 10 mm×250 mm, 5 μm;
column temperature is 40° C.;
mobile phase A is 0.1% DEA in hexane, and the percentage is the volume percentage;
mobile phase B is ethanol;
gradient is mobile phase A/mobile phase B=50/50, and the ratio is volume ratio;
flow rate is 6.0 mL/min;
detection wavelength is UV 210 nm;
the chiral resolution condition 2 includes:
chiral column is CHIRALCEL OD-H 10 mm×250 mm, 5 μm;
column temperature is 40° C.;
mobile phase A is 0.1% DEA in hexane, and the percentage is the volume percentage;
mobile phase B is ethanol;
gradient is mobile phase A/mobile phase B=60/40, and the ratio is volume ratio;
flow rate is 3.0 mL/min; and
detection wavelength is UV 210 nm.

9. A process for preparing the compound as shown in general formula I, comprising the following steps:

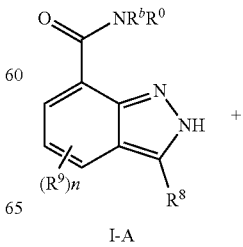

I-A

-continued

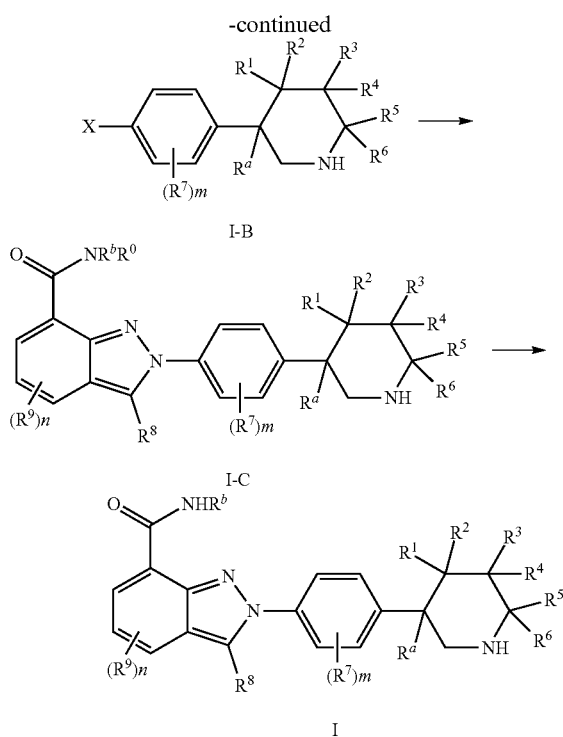

a1) coupling the compound of the formula I-A with the compound of the formula I-B under basic condition in presence of a metal catalyst to give the compound of general formula I-C;

b1) removing the protecting group of the compound of general formula I-C under acidic condition to give the compound as shown in general formula I;

wherein X is halogen, $R^0$ is an amino protecting group, and $R^a$, $R^b$, $R^1$, $R^2$, $R^3$, $R^4$, $R^5$, $R^6$, $R^7$, $R^8$, $R^9$, m and n are as defined in claim 1.

10. A pharmaceutical composition comprising a therapeutically effective amount of the compound as shown in general formula I, the pharmaceutically acceptable salt thereof, the isomer thereof or the mixture form of the isomers, the solvate thereof, the polymorph thereof, the stable isotope derivative thereof or the prodrug thereof as defined in claim 1, and a pharmaceutically acceptable carrier, diluent or excipient.

11. A method for, relieving and/or treating diseases which are alleviated by PARP inhibitors, comprising administering a therapeutically effective amount of the compound as shown in general formula I, the pharmaceutically acceptable salt thereof, the isomer thereof or the mixture form of the isomers, the solvate thereof, the polymorph thereof, the stable isotope derivative thereof or the prodrug thereof as defined in claim 1.

12. A method for relieving and/or treating cancers, inflammatory diseases, vascular diseases, stroke, renal failure, diabetes, Parkinson's disease, septic shock, neurotoxicity, ischemic shock or injury, transplant rejection, reperfusion injury, retinal injury, UV-induced skin damage, viral infection or multiple sclerosis, comprising administering a therapeutically effective amount of the compound as shown in general formula I, the pharmaceutically acceptable salt thereof, the isomer thereof or the mixture form of the isomers, the solvate thereof, the polymorph thereof, the stable isotope derivative thereof or the prodrug thereof as defined in claim 1.

13. A method for treating cancers or strengthening radiotherapy and/or chemotherapy on cancers treatment, comprising administering a therapeutically effective amount of the compound as shown in general formula I, the pharmaceutically acceptable salt thereof, the isomer thereof or the mixture form of the isomers, the solvate thereof, the polymorph thereof, the stable isotope derivative thereof or the prodrug thereof as defined in claim 1.

14. The method as defined in claim 13, wherein the cancers are selected from a solid tumor, acute or chronic leukemia, lymphoma, central nervous system cancer, brain cancer, hematogenous cancer, peritoneal cancer, gastric cancer, lung cancer, cancer lacking homologous recombination-dependent DNA double-strand break repair activity, and cancer with defective or mutant phenotype on BRCA-1 or BRCA2.

15. The method as defined in claim 14, wherein, the compound as shown in general formula I, the pharmaceutically acceptable salt thereof, the isomer thereof or the mixture form of the isomers, the solvate thereof, the polymorph thereof, the stable isotope derivative thereof or the prodrug thereof is used in combination with one or more than one other anticancer agents; the anticancer agents are selected from alkylating agents, platinum drugs, topoisomerase inhibitors, metabolic antagonists, alkaloids, antibody drugs, hormone anticancer agents, proteasome inhibitors, HDAC inhibitors, CDK inhibitors, VEGFR or EGFR inhibitors, m-TOR inhibitors, PI3K inhibitors, B-Raf inhibitors, PARP inhibitors, c-Met kinase inhibitors, ALK inhibitors, AKT inhibitors, ABL inhibitors, FLT3 inhibitors, PD-1 monoclonal antibodies or PD-L1 monoclonal antibodies.

16. A method for relieving and/or treating diseases which are alleviated by PARP inhibitors, comprising administering a therapeutically effective amount of the pharmaceutical composition as defined in claim 10.

17. A method for relieving and/or treating cancers, inflammatory diseases, vascular diseases, stroke, renal failure, diabetes, Parkinson's disease, septic shock, neurotoxicity, ischemic shock or injury, transplant rejection, reperfusion injury, retinal injury, UV-induced skin damage, viral infection or multiple sclerosis, comprising administering a therapeutically effective amount of the pharmaceutical composition as defined in claim 10.

18. A method for treating cancers or strengthening radiotherapy and/or chemotherapy on cancers treatment, comprising administering a therapeutically effective amount of the pharmaceutical composition as defined in claim 10.

19. The method as defined in claim 18, wherein the cancers are selected from a solid tumor, acute or chronic leukemia, lymphoma, central nervous system cancer, brain cancer, hematogenous cancer, peritoneal cancer, gastric cancer, lung cancer, cancer lacking homologous recombination-dependent DNA double-strand break repair activity, and cancer with defective or mutant phenotype on BRCA-1 or BRCA2.

20. The method as defined in claim 18, wherein the pharmaceutical composition is used in combination with one or more than one other anticancer agents; the anticancer agents are selected from alkylating agents, platinum drugs, topoisomerase inhibitors, metabolic antagonists, alkaloids, antibody drugs, hormone anticancer agents, proteasome inhibitors, HDAC inhibitors, CDK inhibitors, VEGFR or EGFR inhibitors, m-TOR inhibitors, PI3K inhibitors, B-Raf inhibitors, PARP inhibitors, c-Met kinase inhibitors, ALK inhibitors, AKT inhibitors, ABL inhibitors, FLT3 inhibitors, PD-1 monoclonal antibodies or PD-L1 monoclonal antibodies.

* * * * *